(12) United States Patent
Deutsch et al.

(10) Patent No.: US 11,918,740 B2
(45) Date of Patent: Mar. 5, 2024

(54) SYSTEM AND METHOD FOR CONTROLLING AND MONITORING FLOW IN AN ENDOTRACHEAL TUBE

(71) Applicant: Hospitech Respiration Ltd., Kfar-Saba (IL)

(72) Inventors: Israel Deutsch, Petach-Tikva (IL); Shai Efrati, Rechovot (IL); Yoav Venkert, Zikhron-Yaakov (IL); Moshe Azizi, Yakir (IL); Yizhaq Vakrat, Moshav Zuriel (IL); Vitali Gelberg, Lod (IL)

(73) Assignee: Hospitech Respiration Ltd., Kfar-Saba (IL)

( * ) Notice: Subject to any disclaimer, the term of this patent is extended or adjusted under 35 U.S.C. 154(b) by 578 days.

(21) Appl. No.: 17/069,912

(22) Filed: Oct. 14, 2020

(65) Prior Publication Data

US 2021/0038843 A1 Feb. 11, 2021

Related U.S. Application Data

(62) Division of application No. 14/370,077, filed as application No. PCT/IL2013/050015 on Jan. 3, 2013, now Pat. No. 10,806,882.

(Continued)

(51) Int. Cl.
*A61M 16/04* (2006.01)
*A61B 5/00* (2006.01)
(Continued)

(52) U.S. Cl.
CPC ..... *A61M 16/0463* (2013.01); *A61B 5/02108* (2013.01); *A61B 5/02141* (2013.01);
(Continued)

(58) Field of Classification Search
CPC .......... A61M 16/0463; A61M 16/0402; A61M 16/0479; A61M 16/0486; A61M 16/044;
(Continued)

(56) References Cited

U.S. PATENT DOCUMENTS 3,931,822 A * 1/1976 Marici .............. A61M 16/0459
128/207.15
4,260,077 A  4/1981 Schroeder
(Continued)

FOREIGN PATENT DOCUMENTS

EP   1547641   6/2005
EP   2305343   4/2011
(Continued)

OTHER PUBLICATIONS

Communication Pursuant to Article 94(3) EPC dated Jul. 8, 2019 From the European Patent Office Re. Application No. 17165876.8. (6 Pages).

(Continued)

*Primary Examiner* — Elliot S Ruddie

(57) ABSTRACT

A system for controlling and monitoring flow in a cuffed endotracheal tube device is disclosed. The system comprises: a connector panel having at least three connectors adapted for establishing fluid communication with proximal ends of at least a first fluid line, a second fluid line and a cuff inflation line of the endotracheal tube device. The system can further comprise a processing unit and a control unit, wherein the processing unit is configured to instruct the control unit to execute various operations, including at least a rinsing procedure, a suctioning procedure, a cuff inflation procedure, a leak detection procedure and a venting procedure, and to select any of the first and the second fluid lines for any of the rinsing, suctioning, leak detection and venting (Continued)

procedures. In some embodiments, the system exploits the cuff as sensor to sense pulmonary data.

20 Claims, 26 Drawing Sheets

Related U.S. Application Data

(60) Provisional application No. 61/582,498, filed on Jan. 3, 2012.

(51) Int. Cl.
*A61B 5/021* (2006.01)
*A61B 5/0215* (2006.01)
*A61B 5/022* (2006.01)
*A61M 16/00* (2006.01)

(52) U.S. Cl.
CPC ............ *A61B 5/0215* (2013.01); *A61B 5/022* (2013.01); *A61B 5/6853* (2013.01); *A61B 5/7278* (2013.01); *A61M 16/044* (2013.01); *A61M 16/0479* (2014.02); *A61M 16/0486* (2014.02); *A61M 2016/0027* (2013.01); *A61M 2016/0413* (2013.01); *A61M 2202/025* (2013.01); *A61M 2202/0258* (2013.01); *A61M 2205/15* (2013.01); *A61M 2205/584* (2013.01); *A61M 2230/30* (2013.01)

(58) Field of Classification Search
CPC .... A61M 2016/0027; A61M 2202/025; A61M 2202/0258; A61M 2205/15; A61M 2205/3331; A61M 2205/3379; A61M 2230/30; A61M 16/0484; A61M 16/0434; A61M 2016/0036; A61M 2016/041; A61M 2016/0413; A61M 2205/584; A61B 5/02108; A61B 5/02141; A61B 5/0215; A61B 5/022; A61B 5/6853; A61B 5/7278
USPC .......................... 128/202.13, 207.14, 207.15
See application file for complete search history.

(56) References Cited

U.S. PATENT DOCUMENTS

| | | | |
|---|---|---|---|
| 4,457,747 | A | 7/1984 | Tu |
| 4,630,606 | A | 12/1986 | Weerda et al. |
| 4,857,056 | A | 8/1989 | Talonn |
| 4,909,783 | A | 3/1990 | Morrison |
| 5,050,297 | A | 9/1991 | Metzger |
| 5,235,973 | A | 8/1993 | Levinson |
| 5,254,086 | A | 10/1993 | Palmer et al. |
| 5,361,753 | A * | 11/1994 | Pothmann ............ A61M 16/021 128/207.15 |
| 5,429,610 | A | 7/1995 | Vaillancourt |
| 5,655,518 | A | 8/1997 | Burden |
| 5,743,886 | A | 4/1998 | Lynn et al. |
| 5,808,203 | A | 9/1998 | Nolan, Jr. et al. |
| 5,819,723 | A | 10/1998 | Joseph |
| 5,890,488 | A | 4/1999 | Burden |
| 5,957,883 | A | 9/1999 | Lin |
| 6,168,568 | B1 | 1/2001 | Gavriely |
| 6,261,238 | B1 | 7/2001 | Gavriely |
| 6,383,142 | B1 | 5/2002 | Gavriely |
| 6,390,091 | B1 | 5/2002 | Banner et al. |
| 6,450,164 | B1 | 9/2002 | Banner et al. |
| 6,571,796 | B2 | 6/2003 | Banner et al. |
| 6,621,278 | B2 | 9/2003 | Ariav |
| 6,641,394 | B2 | 11/2003 | Garman |
| 6,723,053 | B2 | 4/2004 | Ackerman et al. |
| 6,820,618 | B2 | 11/2004 | Banner et al. |
| 6,843,250 | B2 | 1/2005 | Efrati |
| 6,856,141 | B2 | 2/2005 | Ariav |
| 7,674,247 | B2 | 3/2010 | Fojtik |
| 10,806,882 | B2 * | 10/2020 | Deutsch ............ A61B 5/02141 |
| 2001/0021821 | A1 | 9/2001 | Wang et al. |
| 2002/0105340 | A1 | 8/2002 | Ariav |
| 2003/0069549 | A1 | 4/2003 | MacMahon et al. |
| 2004/0104733 | A1 | 6/2004 | Ariav |
| 2004/0123867 | A1 | 7/2004 | Efrati |
| 2004/0207409 | A1 | 10/2004 | Ariav et al. |
| 2005/0027206 | A1 | 2/2005 | Ariav |
| 2005/0027250 | A1 | 2/2005 | Suresh et al. |
| 2005/0277891 | A1 | 12/2005 | Sibbitt |
| 2007/0089748 | A1 | 4/2007 | Madsen et al. |
| 2008/0269625 | A1 * | 10/2008 | Halperin ................ A61B 5/746 600/534 |
| 2008/0283052 | A1 | 11/2008 | Young |
| 2009/0038620 | A1 | 2/2009 | Efrati |
| 2009/0229605 | A1 | 9/2009 | Efrati et al. |
| 2010/0147303 | A1 * | 6/2010 | Jafari ................ A61M 16/0051 128/204.23 |
| 2010/0210907 | A2 | 8/2010 | Schramm |
| 2010/0319702 | A1 | 12/2010 | Wood et al. |
| 2010/0326446 | A1 | 12/2010 | Behlmeier |
| 2011/0023884 | A1 | 2/2011 | Cuevas et al. |
| 2011/0023889 | A1 | 2/2011 | Lin et al. |
| 2011/0046464 | A1 | 2/2011 | Debreczeny et al. |
| 2011/0046653 | A1 * | 2/2011 | Addington ........... A61B 5/6853 606/196 |
| 2011/0073115 | A1 | 3/2011 | Wood et al. |
| 2011/0146690 | A1 | 6/2011 | Wood et al. |
| 2012/0090620 | A1 | 4/2012 | Deutsch |
| 2014/0366874 | A1 | 12/2014 | Deutsch et al. |

FOREIGN PATENT DOCUMENTS

| | | |
|---|---|---|
| GB | 2452776 | 3/2009 |
| JP | 10-502262 | 3/1998 |
| JP | 2004-535246 | 11/2004 |
| JP | 04-116069 | 7/2008 |
| WO | WO 91/12044 | 8/1991 |
| WO | WO 92/07602 | 5/1992 |
| WO | WO 95/28199 | 10/1995 |
| WO | WO 00/67013 | 11/2000 |
| WO | WO 01/00267 | 1/2001 |
| WO | WO 03/007797 | 1/2003 |
| WO | WO 03/036321 | 5/2003 |
| WO | WO 03/048688 | 6/2003 |
| WO | WO 2004/072658 | 8/2004 |
| WO | WO 2005/062719 | 3/2005 |
| WO | WO 2005/076727 | 8/2005 |
| WO | WO 2007/023492 | 3/2007 |
| WO | WO 2009/004483 | 1/2009 |
| WO | WO 2010/046874 | 4/2010 |
| WO | WO-2010046874 A2 * | 4/2010 ............ A61B 5/085 |
| WO | WO 2012/001691 | 1/2012 |
| WO | WO 2013/102905 | 7/2013 |

OTHER PUBLICATIONS

Communication Pursuant to Article 94(3) EPC dated Nov. 28, 2013 From the European Patent Office Re. Application No. 11743640.2.
European Search Report and the European Search Opinion dated Jul. 27, 2017 From the European Patent Office Re. Application No. 17165876.8. (18 Pages).
International Preliminary Report on Patentability dated Jan. 17, 2013 From the International Bureau of WIPO Re. Application No. PCT/IL2011/000520.
International Preliminary Report on Patentability dated Jul. 17, 2014 From the International Bureau of WIPO Re. Application No. PCT/IL2013/050015.
International Search Report and the Written Opinion dated Apr. 30, 2013 From the International Searching Authority Re. Application No. PCT/IL2013/050015.
International Search Report and the Written Opinion dated Nov. 30, 2011 From the International Searching Authority Re. Application No. PCT/IL2011/000520.

(56) References Cited

OTHER PUBLICATIONS

Invitation Pursuant to Article 94(3) and Rule 71(1) EPC dated Jan. 20, 2015 From the European Patent Office Re. Application No. 11743640.2.
Notice of Allowance dated Jun. 17, 2020 from the US Patent and Trademark Office Re. U.S. Appl. No. 14/370,077. (12 pages).
Notice of Reason for Rejection dated Mar. 13, 2015 From the Japanese Patent Office Re. Application No. 2013-517672 and Its Translation Into English.
Notification of Office Action dated May 6, 2014 From The State Intellectual Property Office of the People's Republic of China Re. Application No. 201180042161.1 and Its Translation Into English.
Notification of Office Action dated Jul. 15, 2015 From the State Intellectual Property Office of the People's Republic of China Re. Application No. 201180042161.1 and Its Summary and Translation of Claims in English.
Office Action dated Dec. 17, 2015 From the Israel Patent Office Re. Application No. 223985 and Its Translation Into English.
Official Action dated Oct. 7, 2013 From the US Patent and Trademark Office Re. U.S. Appl. No. 13/342,125.
Official Action dated Jan. 18, 2019 From the US Patent and Trademark Office Re. U.S. Appl. No. 14/370,077. (15 Pages).
Official Action dated Feb. 24, 2017 From the US Patent and Trademark Office Re. U.S. Appl. No. 14/370,077. (32 Pages).
Official Action dated Sep. 26, 2012 From the US Patent and Trademark Office Re. U.S. Appl. No. 13/342,125.
Official Action dated Mar. 29, 2013 From the US Patent and Trademark Office Re. U.S. Appl. No. 13/342,125.
Official Action dated Nov. 30, 2017 From the US Patent and Trademark Office Re. U.S. Appl. No. 14/370,077. (20 pages).
Official Action dated Oct. 31, 2019 From the US Patent and Trademark Office Re. U.S. Appl. No. 14/370,077. (20 Pages).
Official Copy of Decision of Rejection dated Dec. 25, 2015 From the Japanese Patent Office Re. Application No. 2013-517672 and Its Translation Into English.
Restriction Official Action dated Sep. 8, 2016 From the US Patent and Trademark Office Re. U.S. Appl. No. 14/370,077.
Restriction Official Action dated Jul. 31, 2012 From the US Patent and Trademark Office Re. U.S. Appl. No. 13/342,125.
Search Report dated May 6, 2014 From The State Intellectual Property Office of the People's Republic of China Re. Application No. 201180042161.1 and Its Translation Into English.
Supplementary European Search Report and the European Search Opinion dated Aug. 17, 2015 From the European Patent Office Re. Application No. 13733827.3.
Qosina "Male Luer Lock Alternating Procedure Syringe, 10ml, Transparent Blue", Component Information, Qosina 2012 Print Catalog, p. 390, 2012.
Wilder et al. "Clinical Evaluation of Tracheal Pressure Estimation From the Endotracheal Tube Cuff Pressure", Journal of Clinical Monitoring and Computing, 14(1): 29-34, 1998.

* cited by examiner

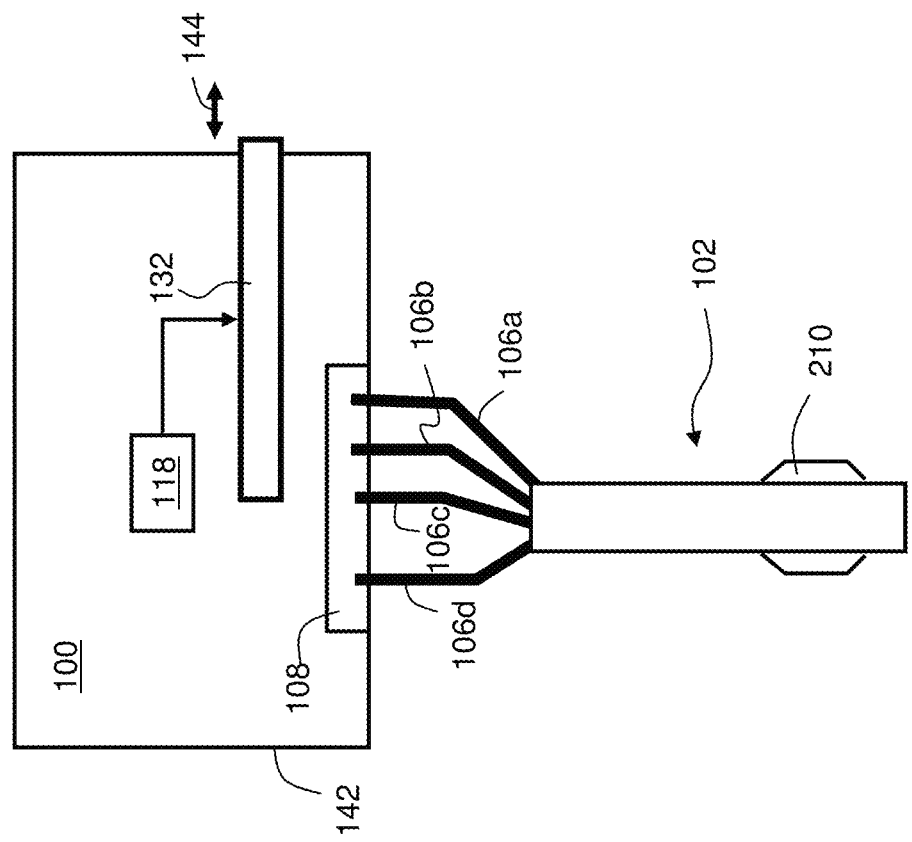

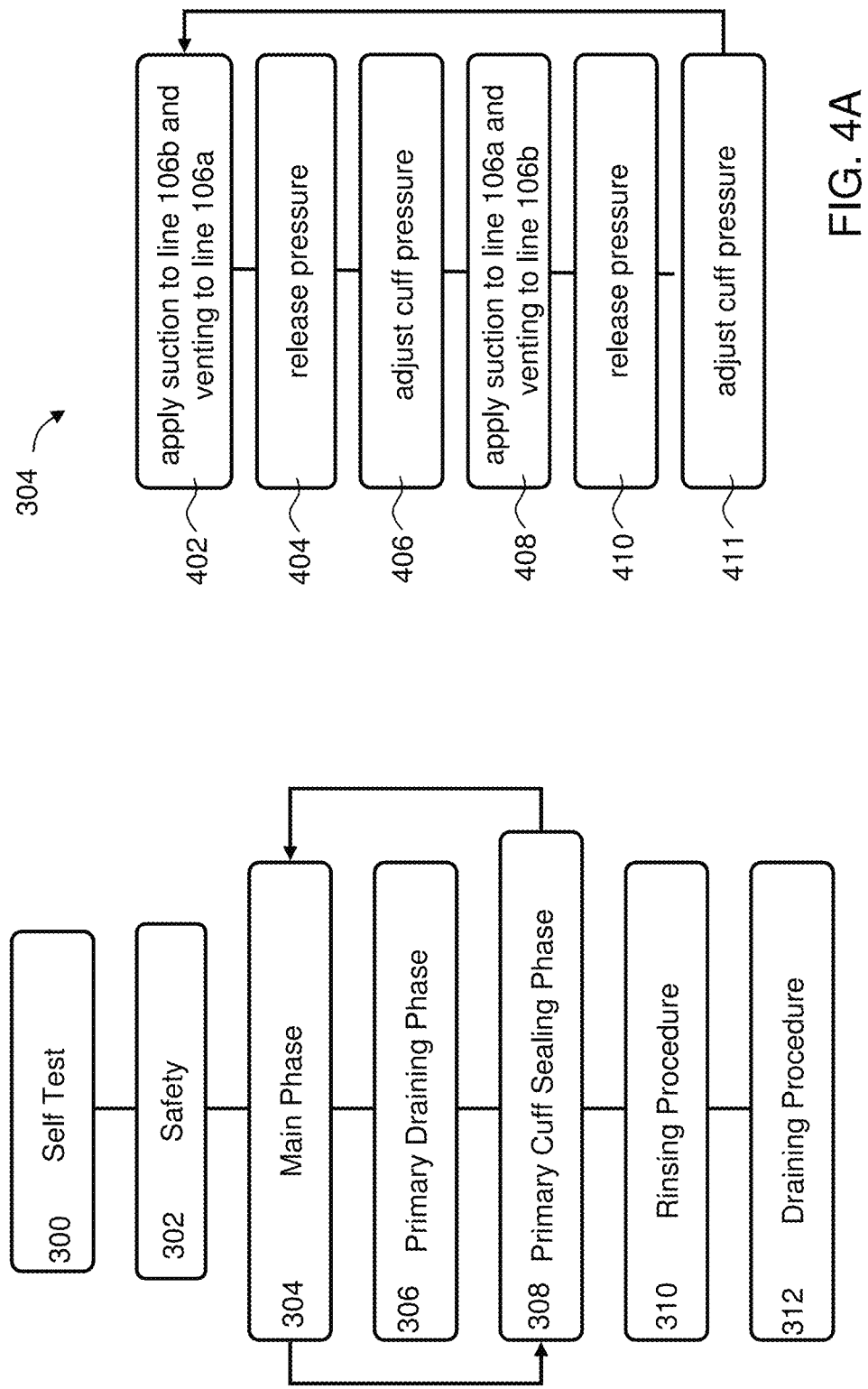

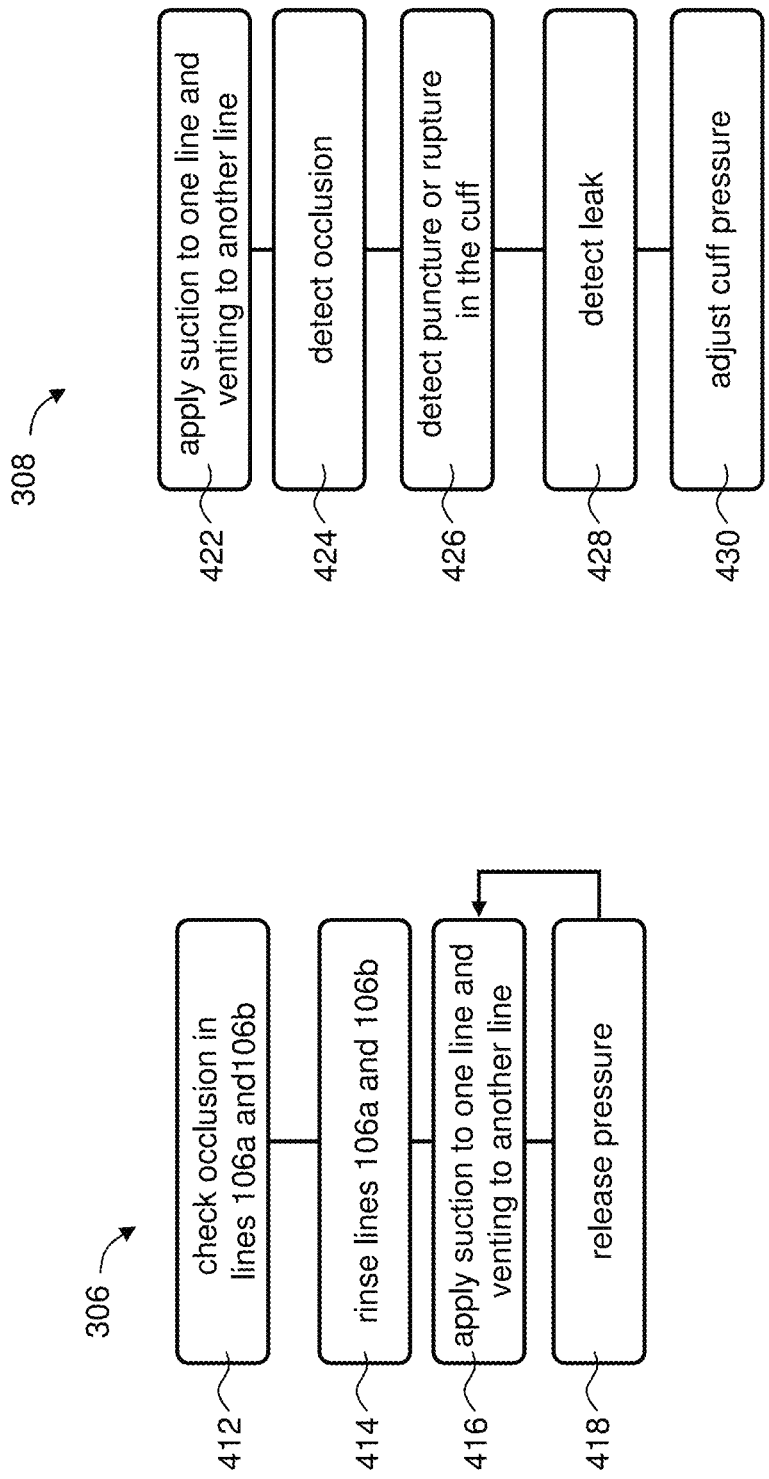

SYSTEM AND METHOD FOR CONTROLLING AND MONITORING FLOW IN AN ENDOTRACHEAL TUBE

RELATED APPLICATION

This application is a division of U.S. patent application Ser. No. 14/370,077 filed on Jul. 1, 2014, which is a National Phase of PCT Patent Application No. PCT/IL2013/050015 having International Filing Date of Jan. 3, 2013, which claims the benefit of priority of U.S. Provisional Patent Application No. 61/582,498 filed Jan. 3, 2012. The contents of the above applications are all incorporated herein by reference in their entirety.

FIELD AND BACKGROUND OF THE INVENTION

The present invention, in some embodiments thereof, relates to intubation and, more particularly, but not exclusively, to a system and method for controlling and monitoring flow in an endotracheal tube.

Mechanical ventilation is necessary to assist patients having difficulties in breathing spontaneously. In the medical treatment of patients requiring breathing assistance, it is common to insert an endotracheal tube into the trachea of the patient, by way of the mouth, nose or any other surgically created opening, including tracheostomy. One end of the endotracheal tube is connected to a ventilator which periodically forces air into the lungs through the tube. The distal end of the tube is typically provided with an inflatable cuff which is inflated by conventional means subsequently to the insertion of the tube into the trachea. The inflated cuff is supposed to provide a seal against the interior wall of the trachea.

In order to ventilate a patient, air is forced into the patient's lungs by a mechanical ventilation system. The forced air is transferred into the lungs from the ventilator via an endotracheal tube connected at its proximal side to the ventilator pipe, and its distal ends within the trachea above the carina. During exhalation, air flows back from the lungs trough the tube. The endotracheal tube is inserted into the trachea in order to maintain an open air passage or to deliver oxygen and permit the suctioning of mucus from the lungs.

The length of the endotracheal tube is designed such that the proximal end of the tube is connected to a pipe attached to the ventilator, while the distal end of the tube is located within patient's trachea, past the vocal cords above the carina.

The outer diameter of the tube is designed so it is smaller than the trachea inner diameter. This is done to facilitate insertion, and to prevent damage due to mechanical force on the trachea tissue. Therefore the tube is supplied in different outer diameters to fit different trachea sizes.

Recently, the mechanical ventilation industry and the endotracheal tube industry have independently introduced new brands having advanced features that improve the treatment of intubated patients.

The ventilation industry adopted the patient assist ventilation procedures aimed to augment patient spontaneous breathing efforts. These systems implement various methods to reduce Work Of Breathing (WOB) by synchronizing and matching ventilation flow and pressure to patient's pulmonary potential. Representative examples of systems developed by the mechanical ventilation industry include systems disclosed in U.S. Published Application Nos. 201010326446 and 2011000046464, and U.S. Pat. Nos. 6,820,618, 6,390,091 and 6,571,796.

The endotracheal tube industry provided improved endotracheal tubes having various features, such as high volume low pressure and thin walled cuffs for better sealing at lower intra cuff pressures to prevent secretions leakage into lungs preventing Ventilator Associated Pneumonia (VAP) and to reduce tracheal intubation associated complications, sensors for determining the location of the tube, special anchoring means and the like. Representative examples of recent developments in endotracheal tubes include, U.S. Published Application Nos. 20110146690, 20110073115, 20100319702 and 20110023889.

Additional background art includes International Publication Nos. WO2007/023492, WO2010/046874, both assigned to the same assignee as the present application and being incorporated by reference by its entirety.

International Publication No. WO2007/023492 (hereinafter the '492 Application) discloses a technique which can be efficiently used in intubation procedures. One or more measures being indicative of secretion leakage past the cuff are measured as compared to one or more optimal values. The cuff filling is adjusted based on the said comparison. The measures include carbon dioxide concentration, a proxy measure from which such concentration can be inferred, or the level of one or more additives delivered to a subject during intubation so as to identify formation of leakage duct on cuff circumference, by measuring its additive residuals above the cuff.

International Publication No. WO2010/046874 (hereinafter the '874 Application), discloses a technique for monitoring tracheal pressure of a ventilated subject. The sealing of the trachea by the cuff is monitored using a close loop control, and the cuff pressure is used as a proxy sensor for the tracheal pressure. The '874 application also discloses suctioning secretions from above cuff, from the endotracheal tube or/and lungs in synchronization with variations in the monitored tracheal pressure and/or the monitored cuff intra pressure and/or the exhale period of the subject.

Additional background art includes Wilder et al., Journal of Clinical Monitoring and Computing Vol. 14 No. 1 (1998), 29.

SUMMARY OF THE INVENTION

According to an aspect of some embodiments of the present invention there is provided a system for controlling and monitoring flow in a cuffed endotracheal tube device. The system comprises: a connector panel having at least three connectors adapted for establishing fluid communication with proximal ends of at least a first fluid line, a second fluid line and a cuff inflation line of the endotracheal tube device. The system further comprises a processing unit and a control unit, wherein the processing unit is configured to instruct the control unit to execute various operations, including at least a rinsing procedure, a suctioning procedure, a cuff inflation procedure, a leak detection procedure and a venting procedure, and to select any of the first and the second fluid lines for any of the rinsing, suctioning, leak detection and venting procedures.

According to an aspect of some embodiments of the present invention there is provided a ventilation system. The system comprises a ventilation machine and the system described herein.

According to an aspect of some embodiments of the present invention there is provided a method of ventilating a subject. The method comprises: intubating the subject with a cuffed endotracheal tube device having at least a main tube, a cuff inflation line, a first fluid line and a second fluid line; connecting the main tube to a ventilation machine; and connecting the cuff inflation line, the first fluid line and the second fluid line to the system described herein.

According to an aspect of some embodiments of the present invention there is provided a method of determining cuff rupture in a cuffed endotracheal tube device introduced into the trachea of a subject. The method comprises: monitoring cuff pressure in the cuff; searching for a statistically significant frequency of pressure spikes in the monitored cuff pressure; and if the statistically significant frequency is found, determining that the cuff is ruptured.

According to an aspect of some embodiments of the present invention there is provided a system for controlling and monitoring flow in a cuffed endotracheal tube device. The system comprises: a connector panel having at least three connectors adapted for establishing fluid communication with proximal ends of at least a first fluid line, a second fluid line and a cuff inflation line of the endotracheal tube device. The system further comprises a processing unit and a control unit, wherein the processing unit is configured to instruct the control unit to execute operations including at least a rinsing procedure, a suctioning procedure, a cuff inflation procedure, a leak detection procedure and a venting procedure. According to some embodiments of the invention the rinsing procedure is, at least partially, a staggered procedure, with controlled gaps between sequential rinse stages.

According to an aspect of some embodiments of the present invention there is provided a system for controlling and monitoring flow in a cuffed endotracheal tube device. The system comprises: a connector panel having at least three connectors adapted for establishing fluid communication with proximal ends of at least a first fluid line, a second fluid line and a cuff inflation line of the endotracheal tube device. The system further comprises a processing unit and a control unit, wherein the processing unit is configured to instruct the control unit to execute operations including at least a rinsing procedure, a suctioning procedure, a cuff inflation procedure, a leak detection procedure and a venting procedure. According to some embodiments of the invention the control unit comprises a flow measuring device configured for measuring flow rate at least in the first and the second fluid lines, wherein the control unit is configured for identifying occlusion in a respective fluid line based on the flow rate, and for executing the procedures based, at least in part, on the monitored flow rate.

According to an aspect of some embodiments of the present invention there is provided a system for controlling and monitoring flow in a cuffed endotracheal tube device. The system comprises: a connector panel having at least three connectors adapted for establishing fluid communication with proximal ends of at least a first fluid line, a second fluid line and a cuff inflation line of the endotracheal tube device. The system further comprises a processing unit and a control unit, wherein the processing unit is configured to instruct the control unit to execute operations including at least a rinsing procedure, a suctioning procedure, a cuff inflation procedure, a leak detection procedure and a venting procedure. According to some embodiments of the invention the control unit comprises a cuff inflation and deflation module configured to measure a cuff pressure within the cuff inflation line, to identify cuff pressure variations, and to control the pressure responsively to the identified variations.

According to some embodiments of the invention the connector panel comprises a drain vacuum connector adapted for establishing fluid communication with a proximal draining line of a drain collection container having an under-pressure therein, wherein the control unit is configured for directing to the draining line both tracheal secretions and lung secretions collected during the suctioning procedure.

According to some embodiments of the invention the suctioning procedure is a periodic procedure, wherein each period comprises a suctioning operation followed by a pressure release operation.

According to some embodiments of the invention the rinsing procedure is, at least partially, a staggered procedure, with controlled gaps between sequential rinse stages.

According to some embodiments of the invention the control unit is configured for introducing a first amount of the rinsing fluid in a staggered manner, and a second amount of the rinsing fluid in a continuous manner. According to some embodiments of the invention the first amount of the rinsing fluid generally equals a fluid capacity of the respective line.

According to some embodiments of the invention the control unit is configured for pausing a flow of the rinsing fluid between the introduction of the first and second amounts.

According to some embodiments of the invention the control unit is configured to deliver rinsing fluid into one of the fluid lines at a first volumetric flow rate, and to simultaneously withdraw fluid from another of the fluid lines at a second volumetric flow rate, wherein there is a linear relation between the first and the second volumetric flow rates.

According to some embodiments of the invention the control unit is configured to deliver the first amount of the rinsing fluid to the respective fluid line and also to deliver a third amount of the rinsing fluid into the other fluid line, prior to the simultaneous delivery and withdrawal.

According to some embodiments of the invention the control unit is configured to automatically increase pressure in the cuff inflation line, immediately prior to the execution of the rinsing procedure.

According to some embodiments of the invention the control unit comprises an adjustable pressure regulator being connectable to a vacuum source and configured for regulating a suction vacuum during the suctioning procedure based, so as to ensure that the suction vacuum is within a predetermined range. According to some embodiments of the invention the pressure regulator comprises capacitance circuitry configured for reduce spiking pressures.

According to some embodiments of the invention the control unit comprises flow measuring device configured for measuring flow rate at least in the first and the second fluid lines, wherein the processing unit is configured for identifying occlusion in a respective fluid line based on the flow rate. According to some embodiments of the invention the control unit is configured for executing the procedures based, at least in part, on the monitored flow rate.

According to some embodiments of the invention the control unit is configured for executing the leak detection procedure via the first fluid line if the first fluid line is not occluded, and via the second fluid line otherwise.

According to some embodiments of the invention the control unit is configured for executing the leak detection procedure via the first fluid line if the first fluid line is not occluded, executing the leak detection procedure via the second fluid line if the second fluid line is not occluded, and skipping the leak detection procedure if both the first and the second fluid lines are occluded.

According to some embodiments of the invention the control unit is configured for executing the suctioning procedure via a respective fluid line following identification of occlusion in the fluid line, wherein a vacuum level of the suctioning procedure is at least temporarily altered so as to unocclude the line. According to some embodiments of the invention the vacuum level is updated gradually, wherein the flow rate is measured for the identification of the occlusion following each update. According to some embodiments of the invention a pressure characterizing the vacuum level is maintained at a value above −120 mmHg at all times.

According to some embodiments of the invention the control unit is configured for executing the suctioning procedure and the venting simultaneously via two different fluid lines.

According to some embodiments of the invention the processing unit is configured for identifying occlusion in the cuff inflation line, wherein the control unit is configured to execute a venting operation through the cuff inflation line, responsively to the identification of the occlusion.

According to some embodiments of the invention the processing unit is configured to analyze variations in cuff pressure within the cuff inflation line and to identify the occlusion based on the analysis.

According to some embodiments of the invention the operations comprise a sequential and periodic transition between a main phase, a primary draining phase and a primary cuff sealing phase.

According to some embodiments of the invention the main phase is executed for a predetermined time period (e.g., from about 15 to about 25 minutes), the primary draining phase is executed following every execution of the main phase, and the primary cuff sealing phase is executed following every execution of the primary draining phase.

According to some embodiments of the invention the main phase comprises a leak detection procedure via the first line followed by a leak detection procedure via the second line, wherein the control unit is configured to cease the main phase and switch to the primary cuff sealing phase if a leak above a predetermined level is detected.

According to some embodiments of the invention the main phase comprises an occlusion detection procedure via the first and the second lines, wherein the control unit is configured to execute the rinsing and the venting procedure in the fluid lines if an occlusion is detected.

According to some embodiments of the invention the primary cuff sealing phase comprises a leak detection procedure, wherein the control unit is configured to increase pressure in the cuff inflation line, if a leak above a predetermine level is detected, and to reduce pressure in the cuff inflation line otherwise. According to some embodiments of the invention the rate characterizing the pressure increment is higher than rate characterizing the pressure reduction.

According to some embodiments of the invention the control unit comprises a cuff inflation and deflation module configured to measure a cuff pressure within the cuff inflation line, to identify cuff pressure variations, and to control the pressure responsively to the identified variations in closed loop control.

According to some embodiments of the invention the processing unit is configured for comparing the identified variations to a characteristic breathing pattern of a subject being intubated by the endotracheal tube, wherein the cuff inflation and deflation module is configured to control the cuff pressure responsively to the comparison.

According to some embodiments of the invention the cuff inflation and deflation module is configured for changing the pressure if a deviation of the identified variations from the characteristic breathing pattern is above a predetermined threshold.

According to some embodiments of the invention the cuff inflation and deflation module is configured for gradually decreasing the pressure if the measured pressure is above a predetermined pressure threshold for a predetermined period of time.

According to some embodiments of the invention the processing unit is configured for determining cuff rupture, and issuing an alert signal if cuff rupture is determined.

According to some embodiments of the invention the processing unit is configured for identifying coughing events based on the pressure. According to some embodiments of the invention the processing unit is configured for monitoring the coughing events over a time period and issuing a statistical analysis report pertaining to the monitored coughing events.

According to some embodiments of the invention the processing unit is configured to search for a statistically significant frequency of pressure spikes, and to determine cuff puncture existence if the statistically significant frequency is found.

According to some embodiments of the invention the processing unit is configured to determine cuff rupture existence if the cuff pressure is below a predetermined threshold or if an abrupt drop in the cuff pressure is identified.

According to some embodiments of the invention the control unit is configured to temporarily cease the closed loop control when the cuff pressure variations are above a predetermined threshold.

According to some embodiments of the invention the control unit is configured to maintain a generally constant cuff pressure.

According to some embodiments of the invention the control unit is configured to cease the maintenance of the generally constant cuff pressure for a predetermined time-interval.

According to some embodiments of the invention the processing unit is configured to analyze variations in cuff pressure within the cuff inflation line during the predetermined time-interval and to identify, based on the analysis, at least one event selected from the group consisting of: occlusion in the cuff inflation line, puncture in a wall of the cuff, rupture in a wall of the cuff and patient coughing.

According to some embodiments of the invention the processing unit is configured to analyze variations in cuff pressure within the cuff inflation line during the predetermined time-interval and to calculate, based on the analysis, at least one quantity selected from the group consisting of: tracheal pressure, breathing frequency, blood pulse wave frequency, obstruction level of a main lumen of the endotracheal tube device and resistance of the main lumen to flow.

According to some embodiments of the invention the processing unit is configured for providing an estimated prediction of the subject's spontaneous initiation of inhale and exhale and the subject's pulmonary power as function of time.

According to some embodiments of the invention the system comprises at least one of a display and memory medium, wherein the processing unit is configured for transmitting to the display and/or memory medium history of at least one parameter selected from the group consisting of cuff pressure, cuff leak, occlusion of the first and/or second fluid lines, and lung compliance and/or resistance of a subject being intubated by the endotracheal tube.

According to some embodiments of the invention the connector panel comprises at least four connectors, wherein one of the connectors is adapted for establishing fluid communication with a suction line for suctioning secretions from below the cuff, wherein the control unit comprises a cuff inflation and deflation module configured to measure a cuff pressure within the cuff inflation line and to identify cuff pressure variations, and wherein the control unit is configured for executing a suctioning procedure also via the suction line, in synchronization with the variations.

According to some embodiments of the invention the suctioning via the suction line is at a suctioning pressure being adapted responsively to the cuff pressure.

According to some embodiments of the invention the processing unit is configured for identifying exhale period, wherein the control unit is configured for synchronizing the suctioning via the suction line with the exhale period.

According to some embodiments of the invention the suction line is an extension of a suction lumen, embedded in a wall of the endotracheal tube device and having an opening at or near a distal end of the endotracheal tube device, below the cuff.

According to some embodiments of the invention the suction line is a separate and retractable catheter introducible into a main lumen of the endotracheal tube device and having a distal opening at or beyond a distal end of the endotracheal tube device, below the cuff.

According to some embodiments of the invention the system comprises a user interface, wherein the control unit is configured to receive signals from the user interface and to vary or bypass at least one operation responsively to the signals.

According to some embodiments of the invention the system comprises a housing and a disposable pneumatic module, wherein the housing is configured for receiving the disposable pneumatic module and the control unit is configured for operating the disposable pneumatic module.

According to some embodiments of the invention the operations comprise a weaning phase in which at least two of the rinsing procedure, the suctioning procedure, the leak detection procedure and the venting procedure are disabled.

According to some embodiments of the invention the rinsing fluid comprises at least one substance selected from the group consisting of an antiseptic substance, a biomarker substance, a local analgesic substance and a secretion diluting substance.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system.

In an exemplary embodiment of the invention, one or more tasks according to exemplary embodiments of method and/or system as described herein are performed by a data processor, such as a computing platform for executing a plurality of instructions.

Optionally, the data processor includes a volatile memory for storing instructions and/or data and/or a non-volatile storage, for example, a magnetic hard-disk and/or removable media, for storing instructions and/or data.

Optionally, a network connection is provided as well. A display and/or a user input device such as onboard buttons, jug wheel, keyboard, touch screen or mouse are optionally provided as well.

BRIEF DESCRIPTION OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A and 1B are schematic illustrations of a system suitable for controlling and monitoring flow in a cuffed endotracheal tube device, according to some embodiments of the present invention;

FIG. 3 is a flowchart diagram describing operations that can be executed by the system according to some embodiments of the present invention;

FIG. 4A is a flowchart diagram general illustrating a main phase, in operations performed by a system according to some embodiments of the present invention;

FIG. 4B is a flowchart diagram general illustrating a primary draining phase, in operations performed by a system according to some embodiments of the present invention;

FIG. 4C is a flowchart diagram general illustrating a primary cuff sealing phase, in operations performed by a system according to some embodiments of the present invention;

DESCRIPTION OF SPECIFIC EMBODIMENTS OF THE INVENTION

Figure 1A:
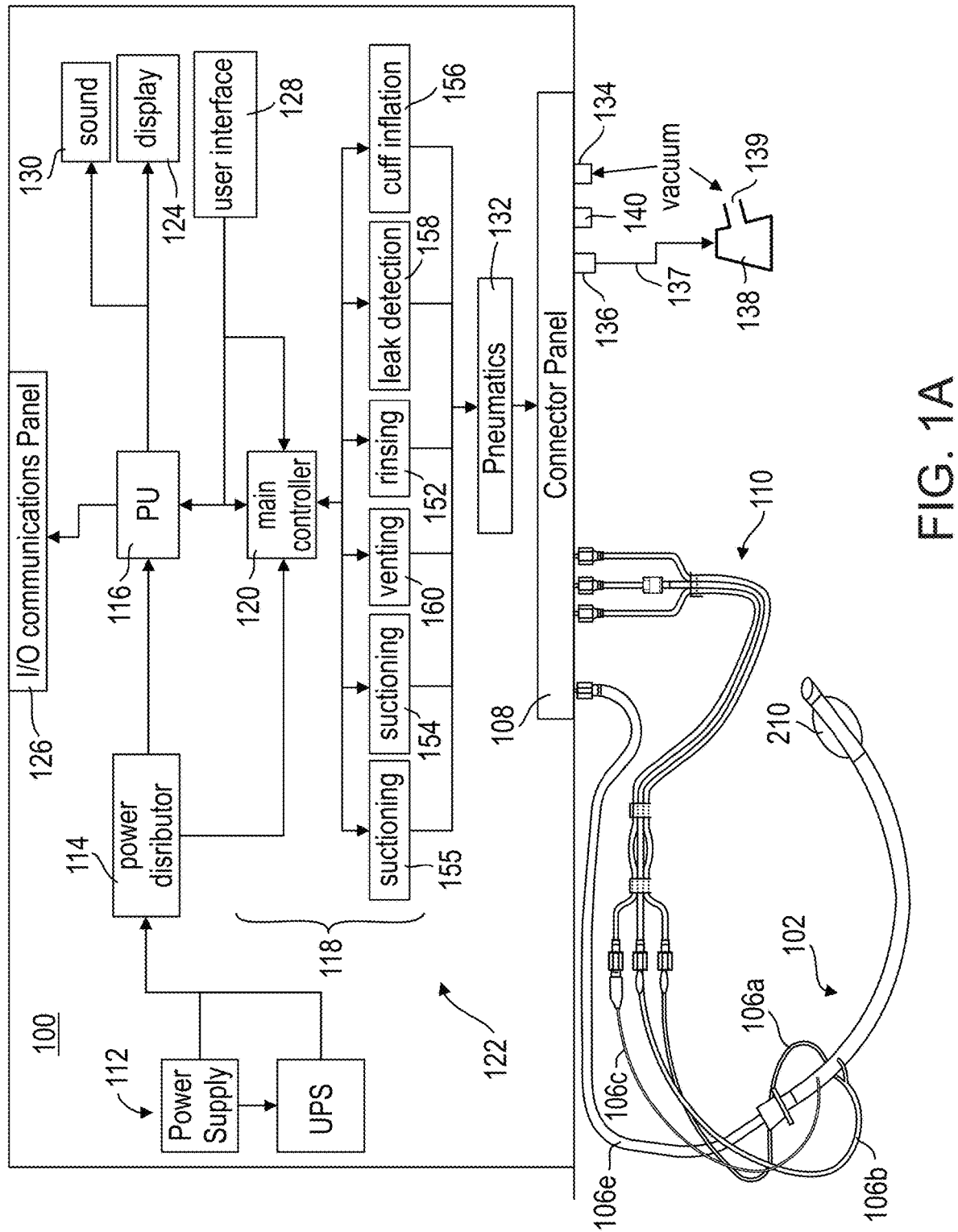

The present invention, in some embodiments thereof, relates to intubation and, more particularly, but not exclusively, to a system and method for controlling and monitoring flow in an endotracheal tube.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present embodiments comprise a system that can be used for providing a measure to determine the cuff pressure which is required for sealing the trachea, preferably at the lowest possible pressure. In some embodiments of the present invention the system performs an adjustable evacuation/suction of tracheal secretions from the subglottal region in the trachea above the cuff. In order to dilute and clear the secretions, and to relieve the bacterial burden, the system can also perform controlled rinsing of the subglottal volume with a suitable rinsing fluid. By providing effective sealing and aspiration of secretions, the system of the present embodiments can help in reducing complications related to prolonged intubation.

System Overview

A system 100 suitable for some embodiments of the present invention is schematically illustrated in FIGS. 1A and 1B. System 100 is particularly useful for controlling and monitoring flow in a cuffed endotracheal tube device 102 having, in addition to its main lumen 202, at least a first fluid line 106a, a second fluid line 106b and a cuff inflation line 106c. System 100 is suitable for use in conjugation with device 102 during any intubation procedure, including, without limitation, oral, nasal endotracheal intubation and tracheotomy. Optionally, device 102 also comprises an additional fluid line 106d (not shown, see FIG. 2B). An endotracheal tube device suitable for the present embodiments is described hereinunder with reference to FIGS. 2A-2D.

Optionally and preferably, system 100 comprises a power supply 112 which can be a medical grade isolated power supply. Alternatively, system 100 can be connected to an external power supply unit (not shown). The power is preferably distributed to the components of the system via a power distributor board 114, which provide each component with the appropriate voltage. In some embodiments of the present invention system 100 comprises an Uninterruptible Power Supply (UPS) for ensuring continuous operation of system 100, e.g., when there is a need to disconnect the system from the main power supply for short periods or there is a shutdown of the main power. Any type of UPS can be used, for example, one or more series of Li-Ion cells, or the like.

System 100 comprises a connector panel 108 having three or more connectors adapted for establishing fluid communications with the respective proximal ends of lines 106a-c. Optionally, panel 108 also includes at least one additional connector for establishing fluid communications with the proximal end of (i) an external fluid line 106e, such as, but not limited to, an external suction catheter that can be introduced in to the main lumen of the endotracheal tube during the intubation of the subject, and/or (ii) an additional fluid line 106d embedded in the wall of device 102 (not shown, see FIG. 2B). Lines 106a-c, and optionally lines 106d and/or 106e, can be connected to panel 108 either directly or, as illustrated in FIG. 1A, via a harness 110 of fluid lines each connected on its one end to a respective connector of panel 108 and on its other end to a respective fluid line.

Connector panel 108 can also include further additional connectors, for other operations, typically, but not exclusively, those performed using an under-pressure, such as, but not limited to, teeth brushing used for antiseptic and for evacuation of secretions from the oropharynx.

One or more of the connectors in panel 108 and the connectors at the proximal ends of the lines to be connected to panel 108 are of the present embodiments provided with matching colors for preventing misconnections.

Connector panel 108 can optionally include a vacuum connector 134 for connecting system 100 to an external under pressure line or a vacuum pump, for example, via the vacuum network of a hospital or the like. Alternatively, system 100 can include a pump for providing vacuum conditions.

The vacuum level is typically expressed in units of pressure, wherein lower pressure corresponds to higher vacuum level, and higher pressure corresponds to lower vacuum level.

In various exemplary embodiments of the invention panel 108 also includes a drain vacuum connector 136 adapted for establishing fluid communication with a proximal draining line of a drain collection container 138, such as a trap bottle, having an under-pressure therein. The under-pressure in container 138 may be maintained by connecting an outlet 139 of container 138 to a vacuum source. Outlet 139 may be provided with a mechanism, such as floating member (not shown) for blocks fluid from flooding outlet 139, as known in the art.

Panel 108 can optionally and preferably comprise additional connectors for connecting various filters, including, without limitation, an antibacterial filter and a humidity filter. These connectors are collectively shown at 140. One or more of the connectors on panel 108 are optionally and preferably controlled by an electro-optical switch (not shown), which can be configured to alert in case of disconnection.

System 100 preferably comprises a processing unit 116 and control unit 118 having a main controller 120 and one or more operational modules 122, wherein controller 120 controls operational modules 122 responsively to signals received from processing unit 116. Unit 116, 118 and 120 can be provided as separate units, as illustrated in FIG. 1A, or two or more of these units can be united to a single unit. Thus, for example, main controller 120 of unit 118 can have also processing capabilities, in which case unit 118 also functions as unit 116, and system 100 does not include a separate processing unit. Below, a reference to processing unit 116 encompasses both embodiments in which unit 116 is a separate unit and embodiments in which unit 118 serves also as a processing unit.

Processing unit 116 can be a general purpose processor or a dedicated circuitry, and is configured to instruct the control unit to execute various operations described herein. The operations are based on an algorithm which can be supplemented to processing unit 116. For example, the algorithm can be written onto a tangible computer readable medium, such as optical, magnetic or non-volatile electronic memory accessible by processing unit 116. Processing unit 116 can also receive signals from unit 118. In these embodiments, processing unit 116 analyzes the signals conveyed by unit 118 in order to extract information from the signal. Based on the extracted information, unit 118 carries on the operations. The extracted information can also be displayed on a display device 124 or transmitted via an I/O communication panel 126.

Panel 126 can include one or more communication ports, such as Universal Serial Bus (USB) ports to allow connection of system 100 to an external device such as an external computer, an external hard drive, an external memory medium, an external monitor, an external personal device (e.g., personal digital assistance (PDA), smart phone, etc.) or any other device capable of communicating via a communication port such as a USB port. Panel 126 can include an RS232 connection for connecting to an external monitor. Other types of connectors, such as PS2 ports and LAN ports, are also contemplated. Panel 126 serves for allowing the respective external device to download or upload data from and to system 100. Representative examples for data which can be uploaded to system 100 include, without limitation, software updates for processing unit 116 and history data of a particular subject. Representative examples for data which can be downloaded from system 100 include, without limitation, parameters detected and/or calculated by processing unit 116.

Thus, processing unit 116 is optionally and preferably configured for communicating with other processing units or computers. Such communication can be wired communication, e.g., via USB ports or the like, and/or it can be wireless communication, e.g., a Bluetooth® or a WiFi communication that can establish connection between unit 116 and a remote location, for example, via the Internet. When the communication is wireless, panel 126 comprises a suitable wireless communication device for establishing such communication.

Unit 116 can also be configured for communicating (via wired or wireless communication) with systems which are capable of receiving and processing data but may also have other functions. Representative examples include, without limitation, a cellular telephone with data processing functionality, a personal digital assistant (PDA) with data processing functionality, a portable email device with data processing functionality (e.g., a BlackBerry® device), a portable media player with data processing functionality (e.g., an Apple iPod®), a portable gaming device with data processing functionality (e.g., a Gameboy®), and a tablet or touch screen display device with data processing functionality (e.g., an Apple iPad®). Unit 116 can be configured to receive data from and transmit data to any of these systems.

Unit 116 can monitor and operate controller 120, display data via display 124, handle a Graphic User Interface (GUI) displayed on display 124, log the operations and alerts of system 100, and/or transmit and receive data from external devices via I/O communication panel 126. The data can be displayed on display 124 graphically and/or in an alphanumeric presentation. Unit 116 is preferably configured to display visual messages, such as warning messages and system status messages via display 124. In some embodiments of the present invention system 100 includes an electroacoustic device 130, such as a loudspeaker or buzzer, for generating acoustic signals responsively to electrical signals from processing unit 116. For example, unit 116 can be configured to accompany a warning message by an alarm signal.

Controller 120 and/or unit 116 can optionally and preferably receive input also from a user interface unit 128. Unit 128 can include operational buttons and/or touch screen for allowing the operator to insert subject details, select operations profiles, select display modes, change profiles parameters, and react to alerts and the like. Unit 128 is preferably configured to allow the operator to force procedures and/or to bypass procedures dictated by unit 116. In various exemplary embodiments of the invention display 124 can be provided as a touch screen so as to allow display 124 also to serve as a user interface unit, either in addition to or as an alternative to operational buttons that unit 128 may or may not include.

System 100 preferably also includes a pneumatic module 132 which may include an arrangement of valves (e.g., three-way valves) controlled by the controller 120. The valves allow selective fluid communication between modules 122 and the connectors on panel 108 in accordance with the procedures performed by controller 120. In various exemplary embodiments of the invention module 132 comprises seven valves, but other arrangements are not excluded from the scope of the present invention.

Also contemplated are configurations in which external pinch valves and a peristaltic pump are employed, e.g., instead of embedded valves and fluid pump. The external valves and pump optionally and preferably accommodate a disposable unit. The advantage of these embodiments is that they avoid the need to disinfect the inner pneumatics, since the disposable unit can replace the pipes that require disinfection. A representative example of system 100 in embodiments of the invention in which pneumatic module 132 is disposable is schematically illustrated in FIG. 1B, showing a housing 142 configured for receiving disposable pneumatic module 132. Module 132 is made detachable from housing 142, e.g., by sliding module 132 inwardly or outwardly from housing 142 along direction 144. Control unit 118 is configured to control module 132 to perform the pneumatic operations described herein. For clarity of presentation, several features of system 100 that are illustrated in FIG. 1A have been omitted from FIG. 1B.

Exemplary Endotracheal Tube Device

Figure 2A:
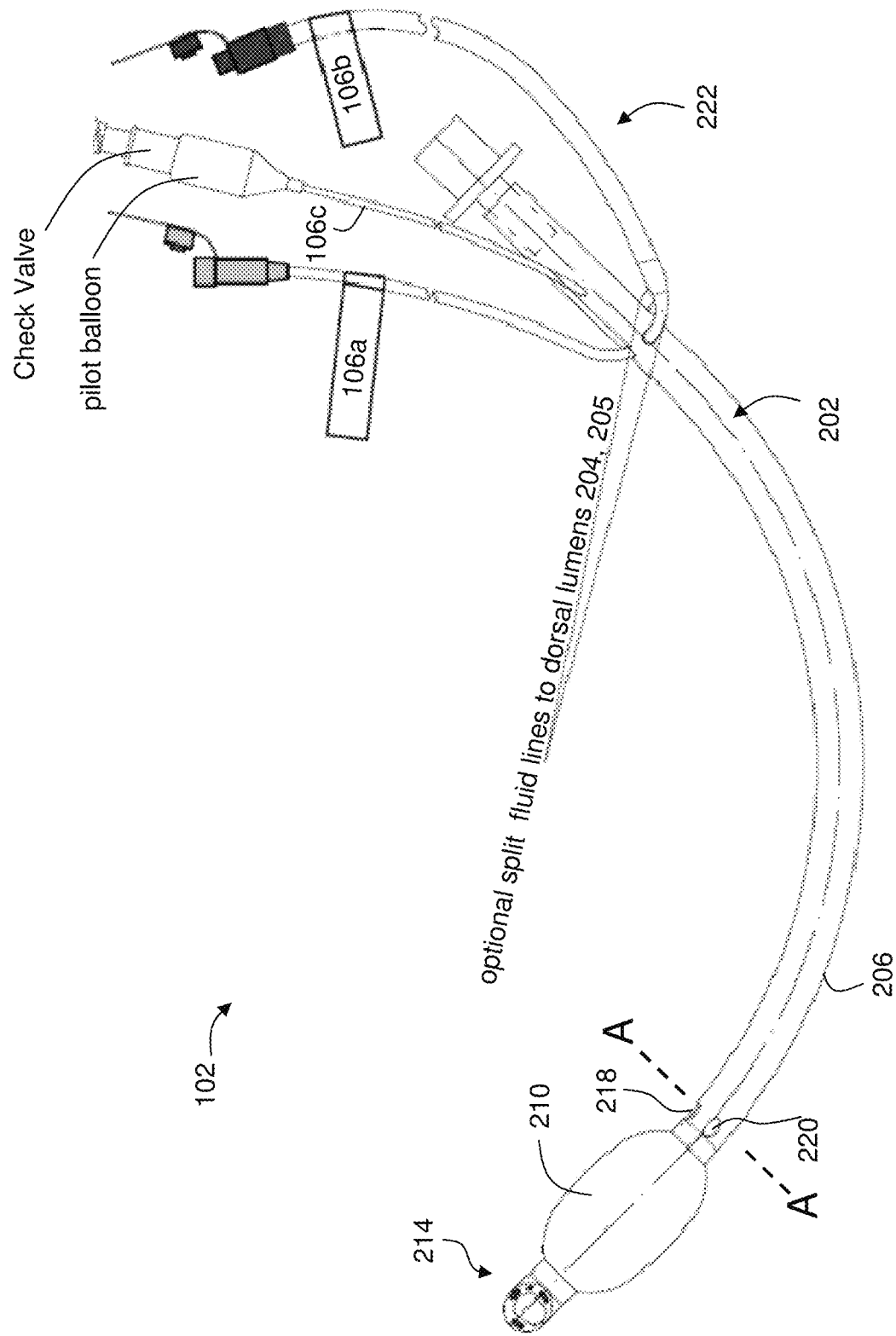
FIGS. 2A-2D are schematic illustrations of a cuffed endotracheal tube device, according to some embodiments of the present invention.
Figure 2B:
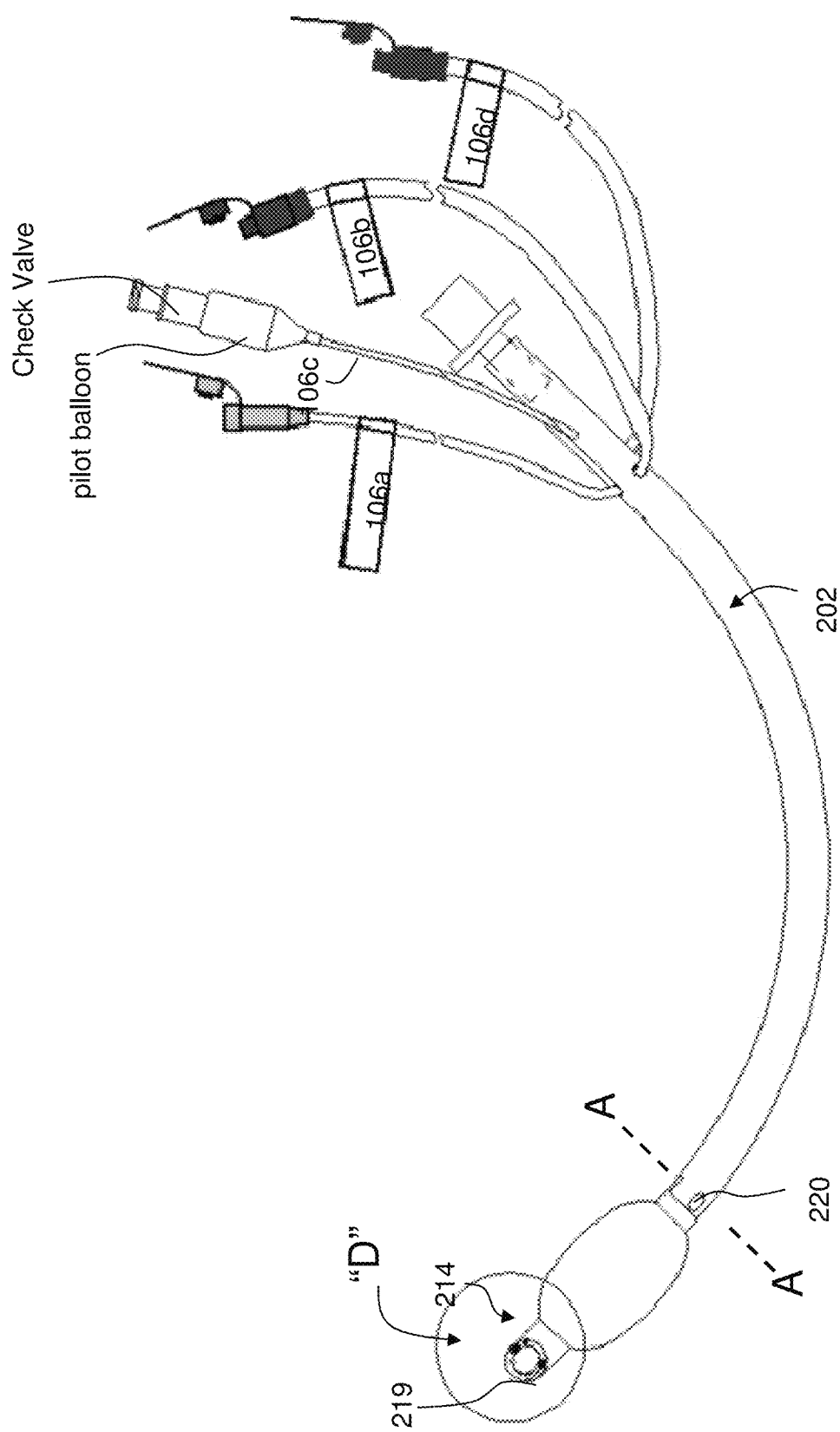
Figure 2D:
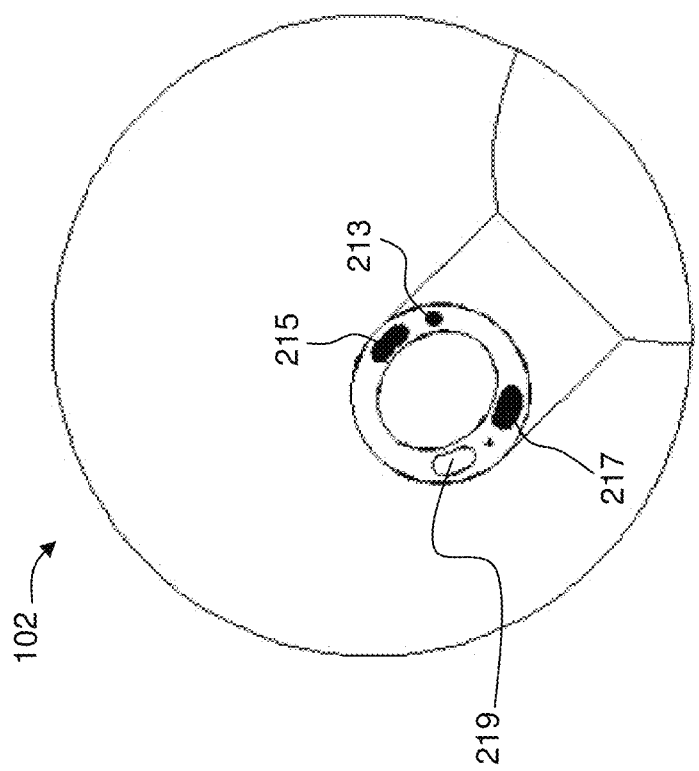
Figure 2C:
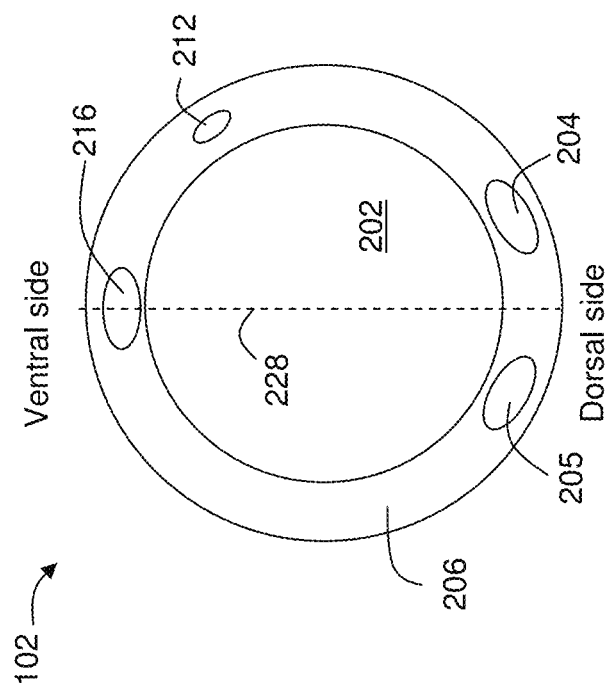

FIGS. 2A-2D are schematic illustrations of an exemplary endotracheal tube device 102 according to some embodiments of the present invention. Endotracheal tube device 102 can be adapted for use during oral, nasal endotracheal intubation or tracheotomy. FIG. 2A shows an external planar view of device 102 according to some embodiments of the present invention, FIG. 2B shows an external planar view of device 102 according to other embodiments of the present invention, FIG. 2C shows a cross-section in a plan along line A-A of FIGS. 2A and 2B, and FIG. 2D is a magnification of the section "D" in FIG. 2C.

Tube device 102 can comprise a tubular wall 206 defining a main lumen 202, and an inflatable cuff 210 disposed circumferentially around wall 206 near the distal end 214 of device 102. Wall 206 has a dorsal side and a ventral side. In use, device 102 is introduced into the subject's trachea (not shown) such that the dorsal and ventral sides of wall 206 respectively face the dorsal and ventral sides of the trachea.

Embedded in wall 206 are two dorsal lumens 204 and 205 at the dorsal side, a ventral lumen 216 at the ventral side, and a cuff inflation lumen 212 (FIG. 2C). Lumen 212 can be formed at any location on the perimeter of wall 206. For example, in the illustration of FIG. 2B lumen 212 is between the ventral and dorsal sides of wall 206. In some embodiments of the present invention lumens 204 and 205 are disposed symmetrically at both sides of the sagittal plane 228, passing through lumen 216 at a cross-section perpendicular to the longitudinal axis of main lumen.

In the embodiment illustrated in FIG. 2A each of dorsal lumens 204, 205 and ventral lumen 216 has a distal opening above cuff 210. Lumens 204, 205 and 216 can terminate above the cuff 210 or they can extend until the distal end 214. In the latter embodiment, lumens 204, 205 and 216 are closed (e.g., welded) at distal end 214. The distal opening of ventral lumen 216 is shown at 218 (FIG. 2A). The distal opening of dorsal lumen 204 is indicated by reference numeral 220. The ordinarily skilled person, provided with the details described herein would know how to locate the distal openings of dorsal lumen 205. Typically, in embodiments in which both dorsal lumens 204 and 205 have a distal opening above cuff 210, their distal openings are at opposite sides of sagittal plane of the tube. In some embodiments, inserts are introduced into one or more of openings 218, 220 and/or the opening of lumen 205 in the direction of distal end 214, so as to close the respective lumen(s) also immediately below these openings.

Alternatively, one of the lumens (e.g., lumen 205) can have an opening below cuff 210, e.g., at the distal end 214 of the tube.

FIG. 2B illustrates an embodiment in which one of lumens 204, 205 and 216 (lumen 205, in the present example) has an opening 219 below cuff 210. The opening 219 is shown at distal end 214 (see FIG. 2D). Also shown in FIG. 2D are the closed ends 213, 215 and 217 of lumens 212, 216 and 204, respectively, below the cuff. While FIG. 2D illustrates an embodiment in which lumen 205 has an opening 219 below the cuff, this is not necessarily be the case since in some embodiments, other lumens can have an opening below the cuff. Specifically, in some embodiments, lumens 205 and 216 are closed below the cuff while lumen 204 has an opening below the cuff at 217, and in some embodiments lumens 204 and 205 are closed below the cuff while lumen 216 has an opening below the cuff at 215.

Each of the lumens is in fluid communication with one of the fluid lines.

In the representative example illustrated in FIG. 2A, ventral lumen 216 extends into line 106a, cuff inflation lumen 212 extends into line 106c and both dorsal lumens 204 and 205 extend into line 106b such that they are unified within line 106b. As shown, line 106b is split into two fluid lines each leading to one of lumens 204 and 205.

In the representative example illustrated in FIG. 2B, ventral lumen 216 extends into line 106a and cuff inflation lumen 212 extends into line 106c, lumen 204 extends into line 106b, and lumen 205 extends into line 106d, such that there is no direct fluid communication between lines 106b and 106d within device 102.

Device 102 can also comprise a pilot balloon and check valve mounted on line 106c. The pilot balloon can be used by the physician as first quick check of cuff inflation. In situations in which, for example, the cuff pressure is reduced, the physician can press the pilot balloon between the two fingers and feel the response. The physician can also use the pilot balloon and check valve for manually inflating the cuff. In this scenario, the physician repeatedly presses the pilot balloon to create local vacuum within the pilot balloon and to drive the check valve piston inwardly and pumping air inside the balloon. Such operation increases the volume of air encapsulated within the enclosure created by cuff, its embedded lumen, and the external line up to check valve. The rise of volume of air pumped into this enclosure increasing the intra cuff pressure.

As will be explained below, in some embodiments of the present invention each of the dorsal 204 and 205 and ventral 216 lumens can serve for any procedure selected from the group consisting of rinsing, suctioning, leak detection and venting, depending on the operation of control unit 218.

Exemplary Control Unit

In some embodiments of the present invention (FIG. 1A) the control unit 118 execute, based on the algorithm, operations including at least a rinsing procedure, a suctioning procedure, a cuff inflation procedure, a leak detection procedure and a venting procedure. This can be achieved by providing unit 118 with a rinsing module 152 for executing the rinsing operation, a suctioning module 154 for executing the suctioning operation, a cuff inflation module 156 for executing the cuff inflation operation, a leak detection module 158 for executing the leak detection operation and a venting module 160 for executing the venting operation.

For any of the rinsing operation, the suctioning operation, the leak detection operation and the venting operation, unit 118 is optionally and preferably automatically selects a fluid line from lines 106a and 106b and performs the respective operation through the selected line.

Optionally, suctioning module 154 performs suction operation also below the cuff for evacuating secretions as further detailed hereinbelow.

Optionally, suctioning module 154 is also operated manually, for example, for oropharynx evacuation of secretions using either a separate suction catheter introduced externally to main lumen of device 102 and/or for supplying an under-pressure for a teeth brushing device for teeth brushing while evacuating secretions from the oropharynx.

Rinsing module 152 preferably comprises a pump and is configured to introduce a rinsing fluid into one of lines 106a and 106b. Rinsing module 152 is controlled by controller 120 which establishes a fluid communication between rinsing module 152 and one of lines 106a and 106b (for example, by signaling the valves in pneumatic module 132) and thereafter signals rinsing module 152 to pump the rinsing fluid. Controller 120 can select any of lines 106a and 106b for the rinsing operation. During the ventilation of a subject, there is preferably at least one time period at which controller 120 selects line 106a and at least one time period at which controller 120 selects line 106b for the rinsing operation. Preferred criteria for the selection are provided in the Examples section that follows.

The rinsing fluid can be of any type, including, without limitation, a liquid which comprises an antiseptic substance, a biomarker substance, a local analgesic substance, and/or a secretion diluting substance.

In various exemplary embodiments of the invention controller 120 signals rinsing module 152 to generate staggered delivery of the rinsing fluid, for at least part of the rinsing procedure.

As used herein "staggered flow" refers to a flow of liquid which with controlled gaps between sequential flow stages. A staggered flow can be punctuated, wherein the delivery is smooth and continuous except for short controlled intervals. In some embodiments of the present invention the staggered flow is pulsatile, wherein the delivery part is controlled. In some embodiments of the present invention the staggered flow is both punctuated and pulsatile, wherein both the delivery part and the intervals are controlled.

A representative example of a staggered flow suitable for the present embodiments is a flow in which two successive rinsing fluid deliveries of 1 second each, are separated a gap of 3 seconds in which the delivery is temporarily ceased.

The advantage of the staggered delivery is that it reduces or generally prevents formation of bubbles in the oropharynx thus eliminating bubbles from external view. It was found by the present inventors that the formation of bubbles during rinsing may be erroneously considered by the medical personnel as originating from the lungs, and it is therefore desired to reduce or prevent such bubbles from being formed.

In various exemplary embodiments of the invention controller 120 signals module 152 to introduce a first amount of the rinsing fluid in a staggered manner, and a second amount of the rinsing fluid in a continuous manner. Typically, the first amount generally equals the fluid capacity of the respective line. In other words, controller 120 preferably signals module 152 to introduce the rinsing fluid in a staggered manner into the respective line until the line is filled. Thereafter, controller 120 preferably signals module 152 to introduce the rinsing fluid in a continuous manner, so as to rinse the subglottal cavity of the subject. In various exemplary embodiments of the invention the flow is paused for several seconds between the staggered and continuous stages.

Figure 8:
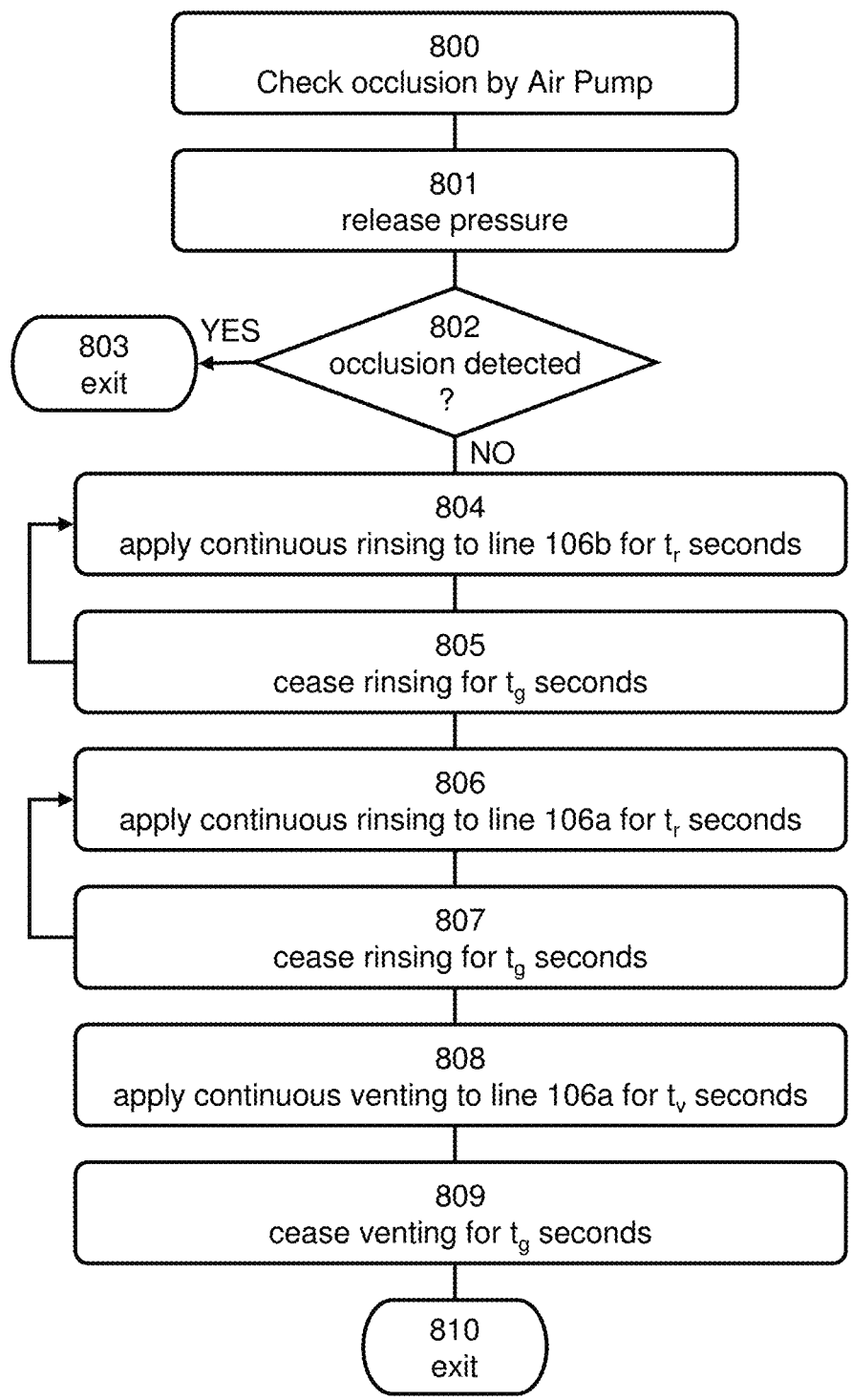
FIG. 8 is a flowchart diagram describing a staggered rinsing procedure, according to some embodiments of the present invention.

A description of a preferred staggered rinsing procedure is provided in the Examples section that follows (see FIG. 8).

Suctioning module 154 is preferably in fluid communication with vacuum connector 134 so that the suctioning operation is facilitated by the under pressure at connector 134. Controller 120 optionally and preferably signals module 154 to begin a continuous suctioning operation generally simultaneously (e.g., within a few milliseconds) with the continuous stage of the rinsing operation performed by module 152.

In various exemplary embodiments of the invention suctioning module 154 comprises an adjustable pressure regulator and/or a flow meter (not shown). The pressure regulator controls the suctioning vacuum applied by module 154, and the flow meter measures the flow generated by the suctioning operation. Regulating the suctioning vacuum is advantageous since it allows suctioning secretions at improved efficiency with reduced risk of tissue damage. Measuring the flow is advantageous since it allows determining whether or not the respective fluid line is occluded and optionally the level (e.g., percentage) of occlusion. This is preferably performed by processing unit 116 which receives, via controller 120, flow rate data from module 154 and determines, base on the flow rate data, whether or not there is an occlusion and optionally also the level of occlusion. Such determination can include thresholding. A preferred procedure for determining occlusion is provided in the Examples section that follows.

In various exemplary embodiments of the invention control unit 118 is configured to deliver rinsing fluid into one of the fluid lines at a first volumetric flow rate $Q_1$, and to simultaneously withdraw fluid from another fluid line at a second volumetric flow rate $Q_2$, wherein there is a linear relation between the first and second volumetric flow rates. For example, $Q_2=Q_1$, or $Q_2=aQ_1$ or $Q_2=aQ_1+b$, where a and b are constants. In some embodiments of the present invention b=0.

Linear relation between $Q_1$ and $Q_2$ can be achieved by configuring controller 120 to control the rinsing 152 and suctioning 154 modules to operate in synchronization.

Optionally and preferably control unit 118 is also configured to enable a priming operation in which a predetermined volume of fluid is first delivered into one of the lines without simultaneous withdrawal of fluid from the other line. Such a priming stage fills the respective fluid line, and optionally partially fills the subglottal volume so as to establish a fluid continuum between system 100 (particularly the rinsing module 152 within system 100) and the subglottal volume and prevents compressible gas voids within the fluid line. The priming operation can be executed for any of fluid lines 106a and 106b. Preferably, the priming operation is executed for both fluid lines 106a and 106b. Specifically, the present embodiments contemplate execution of the priming operation immediately prior to the execution of the aforementioned synchronized operation for both the fluid line that is used synchronized operation for rinsing and the fluid line that is used synchronized operation suctioning.

This feature is advantageous since air filled fluid lines can collapse due to tissue occlusion of suction ports. Under suction pressure, tissue sucked into a suction port can cause a suction line to collapse. If the suction line is filled with a liquid (which unlike air is not compressible) the continuum of liquid within the line prevents the collapse of the suction line and reduces the risk of occlusion in it.

In some embodiments of the invention, controller 120 is configured to operate the rinsing and suctioning module using the following protocol. The following description is for a situation in which line 106b is used for suctioning and line 106a is used for rinsing, but the ordinarily skilled person, provided with the details described herein would know how to adjust the protocol for an opposite situation in which line 106a is used for suctioning and line 106b is used for rinsing.

Hence, rinsing fluid is delivered by the rinsing module to line 106a and also to line 106b. Preferably, for at least part of the time the rinsing fluid is delivered in a staggered manner as further detailed hereinabove. The rinsing fluid is delivered to line 106b until line 106b is entirely filled. Line 106a can be only partially filled. For example, about 3 ml of fluid can be delivered to line 106a.

Thereafter, the suctioning module withdraws fluid from the line 106b and venting module 160 simultaneously performs a venting operation in which air or other gas is forced into line 106a. The gas preferably drives all the fluid in line 106a into the trachea. A typical gas pressure during the venting operation is from about 220 mmHg to about 280 mmHg, e.g., 250 mmHg. The venting module 160 typically comprises a gas pump controllable by control 120.

Following is a description of modules 156 and 158 which are respectively configured for cuff inflation and leak detection.

Cuff inflation module 156 can comprise one or more pressure sensors (not shown) which monitor the pressure within cuff inflation line 106c (hence also within the cuff). Optionally and preferably there is more than one pressure sensor for safety and for increasing the accuracy of measurement. For example, module 156 can include two sensors and processing unit 116 can compare the pressure values measured by the two sensors and issue an alert when the values are not consistent (e.g., deviate from each other by 10% or more). Module 156 also comprises a miniature pump which forces filling fluid (typically air) into the cuff inflation line 106c, and one or more valves which control the amount and rate of fluid delivery into line 106c or deflate the cuff at a controlled rate. Controller 120 operates module 156 routinely as further described below.

Leak detection module 158 aids in assessing the level of sealing provided by the cuff.

This can be done in more than one way, e.g., as described in U.S. Pat. No. 6,843,250 and U.S. Published Application No. 20090229605, both assigned to the same assignee as the present application and being incorporated by reference in their entirety as if fully set forth herein. Some preferred operation principles of module 158 will now be explained.

In some embodiments of the present invention module 158 comprises a carbon dioxide ($CO_2$) monitor which monitors $CO_2$ concentration in any one of lines 106a and 106b, the distal end of which is opened into the airway of the intubated subject, above the cuff. The monitoring of $CO_2$ concentration provides an indication of the sealing of airway by the cuff thereby increases the respiration efficiency and reduces pressure related damage to the airway. Thus, the $CO_2$ serves as an indicator for the leakage of secretions into the lungs, wherein presence of $CO_2$ above the cuff is used as an indicator for secretions leakage into the lungs. The signals regarding presence of $CO_2$ can be transmitted from module 158, optionally and preferably via controller 120, to processing unit 116 which analyses the data and determines the existence or absence of leakage.

Optionally and preferably module 158 also measures ambient $CO_2$ partial pressure. The ambient $CO_2$ partial pressure can be utilized for setting a reference value for the measurement of $CO_2$ partial pressure in lines 106a or 106b. The ambient $CO_2$ partial pressure measurement can be performed once, before or after the insertion of the endotracheal tube into the airway, or in a continuous or alternate manner throughout the procedure. The measurement is preferably not affected by environmental $CO_2$ partial pressure.

In some embodiments, module 158 is configured to receive acoustical data indicative of leakage near the cuff outside the endotracheal tube. The acoustical data can be collected using an acoustical measuring device (not shown), which can be positioned, for example, above and/or below the cuff adjacent to the leaking duct. Acoustical measuring devices suitable to be introduced into the trachea are known in the art and found, e.g., in U.S. Pat. Nos. 5,655,518, 5,890,488, 6,168,568, 6,261,238 and 6,383,142, the contents of which are hereby incorporated by reference.

The ability to identify the formation of a leaking duct along cuff circumference using acoustical device is attributed to the unidirectional flow of air through the duct. The airflow through the leaking duct is unidirectional from the following reason. During the breathing cycle, the air pressure within the lungs is changed periodically. In the inhalation stage, the breathing machine increases the air pressure in the lungs and a pressure drop of about 10-20 mm Hg is built between the lungs and the subglottis. This pressure drop results in airflow from the lungs to the subglottis through the leaking duct. On the exit from duct the air expands with the volume of the subglottis. This expansion continues throughout the inhaling stage.

The magnitude of the air flow through the duct varies from zero (when the air pressure in the lungs equals the ambient air pressure) to a maximal value (when the air pressure in the lungs is maximal, e.g., about 20 mm Hg above ambient air pressure). The maximal magnitude of flow depends on the cross-sectional area of the duct.

The measurement of acoustical data is preferably performed such that background noise is filtered out. The background noise can include all acoustical data associated with phenomena other than leakage of fluid through the leaking duct. Most of the background noise is generated by the breathing machine. During the exhalation stage of the machine (inhalation stage of the subject), the flow in a direction which is opposite to the unidirectional flow through the leaking duct. This is because the air expands, between the cuff and the lungs, from the low diameter of endotracheal tube to the larger diameter of the trachea. During the inhalation stage of the machine (exhalation stage of the subject), the air is compressed again. Thus, the background noise is characterized by oscillatory behavior (from compression to expansion and vise verse) whereas the flow through the leaking duct is unidirectional.

The filtering of the background noise can be done by spectral analysis of the collected acoustical data. Generally, acoustical data characterized by frequencies of from about 1200 Hz to about 2500 Hz, can be identified as proxy to the leakage. Other acoustical data can be associated with breathing, breathing disorders, hoarseness and motion of muscles, such as the heart and lungs. Although acoustical data associated with breathing typically includes low frequencies (below 300 Hz), intermediate frequencies (between 300 and 600 Hz) and high frequencies (between 600 and 1200 Hz), most of the breathing energy is at the range of 60-600 Hz. Acoustical data associated with motion of the heart and lungs is typically in the low frequencies. Acoustical data associated with breathing disorders or hoarseness are typically above the 2000 Hz.

The identification of acoustical data to be excluded can also be performed by performing a calibration step in which the acoustical measurements are performed sufficiently far from the leaking duct so as to define the background noise. Once the background noise is defined it can be subtracted from data collected near the cuff.

In an additional embodiment, the leakage-indicating measure comprises pressure data being indicative of fluid flow near the cuff outside endotracheal tube. Pressure data can be measured using a pressure measuring device (not shown), which preferably has a dynamic range of about 0-2 mm Hg and resolution of 0.01 mm Hg.

The stagnation pressure in the lung during the inhalation stage is about 780 mm Hg, which is about 20 mm Hg above the ambient pressure. When a leaking duct is formed, the air flowing through the duct enters the subglottis in turbulent flow. By the time the air reaches the end of the subglottis the flow becomes laminar. Thus, according to some embodiment of the present invention the pressure is measured at a pressure measuring location within the subglottis, preferably near the vocal cords, where the airflow is substantially laminar.

Miniature sensitive pressure measuring devices are known in the art. Representative example of suitable pressure measuring devices include the pressure sensors of Nexense™, Israel, described, e.g., in U.S. Pat. Nos. 6,621,278 and 6,856,141, International Publication Nos. WO 00/67013, WO 03/036321, WO 03/048688, WO 2004/072658, WO 2005/062719, and WO2005/076727, and U.S. Patent Application Nos. 20050027206, 20040207409, 20040104733, and 20020105340, the contents of which are hereby incorporated by reference.

In an additional embodiment, the leakage-indicating measure comprises flow data being indicative of fluid flow near the cuff outside endotracheal tube. Flow data can be measured using a flow measuring device, such as a flow meter. The flow measuring device is preferably located near the cuff within the subglottis, such that when air flows from the lungs through the leakage duct, the flow measuring device measures the flow. According to a preferred embodiment of the present invention the flow measuring device is characterized by a dynamic range of about 1-3 m/s and resolution of about 10%. Miniature sensitive flow measuring devices are manufactured by Nexense™, Israel, and described in the aforementioned patents and patent applications.

In still another embodiment, the leakage-indicating measure comprises optical data being indicative of presence of secretions near the cuff outside endotracheal tube. In this embodiment, the measuring device comprises one or more miniature cameras located below the cuff, between the cuff and the distal end of the tube. The cameras capture images, preferably video images, which can be analyzed to identify leakage of secretions through the leaking duct in the direction of the lungs. Mature cameras which can be mounted on an endotracheal tube are known in the art, (see, e.g., MedGadget Journal, March 2005 issue, www(dot)medgadget (dot)com/archives/2005/03/etview_ett(dot)html)

In yet another embodiment, the leakage-indicating measure comprises difference between inhaled and exhaled air volumes passing through the endotracheal tube. In this embodiment, the measurement can be performed at the inlet of the breathing machine. The amount of inhaled and exhaled air volume is recorded and the difference therebetween is calculated. Based on this difference, the identification of leakage is achieved.

In a further embodiment, the leakage-indicating measure comprises electrical characteristics of fluid above the cuff outside endotracheal tube. In this embodiment, the fluid above the cuff is transferred into a chamber where it is being heated. When the air contains $CO_2$ it becomes electrically conductive at high temperatures. The electrical conductivity thus serves as a proxy measure to the concentration of $CO_2$ above the cuff. According to a preferred embodiment of the present invention a leakage is identified whenever the electrical conductivity of the air above the cuff exceeds an optimal level. The optimal level can correspond to the aforementioned partial $CO_2$ pressure levels.

In some embodiments of the present invention, one or more identifiable additives are delivered through the main lumen of the endotracheal tube, together with the breathing gas, and module 158 is configured for monitoring the level of this additive within lines 106a and/or 106b. Since the distal ends of these lines is above the cuff and between the outer wall of the tube and the inner wall of the trachea, a level of the additive which is above a predetermined threshold is indicative of leakage.

The identifiable additive is preferably in a gaseous form and it can be either mixed with the breathing gas prior to the delivery or it can be delivered from a different container. Being designed to enter the body of the subject, the identifiable additive is preferably of low toxicity or, more preferably nontoxic.

The delivery of the additive is preferably performed so as to allow the additive to enter the lungs of the subject. During the breathing cycle, additive remnants pass through the lungs and, together with the carbon dioxide waste, are expelled from the lungs by the breathing machine.

Many types of identifiable additives are contemplated. Broadly speaking, for the additive to be identifiable, it should have at least one measurable property which can be used for distinguishing the additive from the breathing gas or other materials in the environment. Thus, the additive is preferably absent from the environment or present in environment in low and known concentrations. When the additive is already present in the environment, it is preferably delivered at a sufficiently higher concentration so as to allow identifying the additive by its concentration level. The distinguishing property of the additive can be, for example, atomic mass, molecular mass and/or one or more other distinguishable properties, including optical, fluorescent and radiative properties. Additionally or alternatively, the additive can have specific electric and/or magnetic properties which can be used to identify the additive.

Representative examples of identifiable additives suitable for the present embodiments include, without limitation, inert gases such as helium, krypton, etc.; radioisotopes, preferably low-radiation radioisotopes with sufficiently short half lives (several seconds to several days) such as technetium radioisotope (e.g., Tc-99), xenon radioisotope (e.g., Xe-133), krypton radioisotope (e.g., Kr-81); colored gases, preferably non-toxic colored gases; and various fluorescent materials, preferably non-toxic fluorescent materials.

The amount of additive which is delivered is preferably selected sufficiently high to allow its identification and sufficiently low so as not to interfere with the breathing of the subject or cause damage to living tissue. The amount can be selected in accordance with the FDA regulations of the specific type of additive used. The optimal amount thus depends on the type of additive and the measuring device which identifies it. It was found by the present inventors that additives suitable for the present embodiments can be identified with an accuracy of from about $7.5 \times 10^{-12}$ (e.g., via mass spectrometry) to about 0.001 (e.g., via radiation detection). Thus, the ratio between the volume of additive to the volume of inhaled air is preferably less than R, where R is a number from about $7.5 \times 10^{-12}$ to about 0.001, where the lower limit is applicable to detection via mass spectrometry.

Module 158 optionally and preferably comprises a mass spectrometer or a gas analyzer, which can provide information regarding the composition and abundance of the atoms present between the airway's wall and the endotracheal tube, thereby to identify additive and to measure its level. For example, when the additive comprises an inert gas (e.g., helium, krypton) the mass spectrometer can identify presence of the atoms of the inert gas (e.g., He, Kr) and optionally measure their concentration level.

Other gaseous materials can also be identified using mass spectrometer. Module 158 can comprise a radiation detecting device. This embodiment is preferred when the additive has specific radiative properties. For example, when the additive comprises radioisotope (e.g., Tc-99, Xe-133, Kr-81), the radiation detecting device can detect radiation emitted by the radioisotope and the presence and/or concentration level of the radioisotope in the between the airway's wall and the endotracheal tube can thus be determined. This can be achieved by sampling fluids (gas or liquid) from the monitoring location and delivering the sample to the radiation detecting device.

In some embodiments the additive has a distinguishing optical property, and module 158 comprises an optical device capable of measuring the optical property. For example, the optical property of the additive can be a distinct color (such as, for example, in the case of colored gas), in which case the optical device can include a miniature camera or an optical waveguide coupled to an external camera, as further detailed hereinabove. Images captured by the camera can be processed to detect the presence of the additive and optionally determine its concentration level above the cuff.

The optical property of the additive can also be fluorescence, in which case the optical device can be a fluorescence camera for detecting fluorescent emissions from the additive, thereby enabling the presence detection and/or concentration level measurement of the additive. When the additive is delivered to a location above the cuff, images are preferably captured below the cuff so as to identify leakage once the additive passes the cuff downstream to the lungs. In this embodiment, the additive can also be selected such that its passing through the leaking duct is accompanied by the formation of colored or colorless bubbles which can be detected by the camera. Bubbles can be also detected by a miniature ultrasound device. In some embodiments, the additive has a distinguishing electrical and/or magnetic property, and module 158 comprises a device capable of measuring electrical and/or magnetic properties, such as conduction, resistance and magnetization.

Irrespectively of the technique employed by module to detect leakage, main controller 120 preferably receives leak detection data from module 158 and operates cuff inflation module 156 responsively to the data. For example, controller 120 can instruct module 156 to increase the pressure in the cuff when the data from module 158 indicates that a leaking duct has been formed, and to reduce the pressure in the cuff when the data indicates that the cuff provides adequate sealing. A preferred procedure for the operation of module 156 responsively to data from module 158 is provided hereinunder.

In some embodiments of the present invention controller 120 monitors variations in the cuff pressure and operate cuff inflation module 156 responsively to the monitored pressure. It was found by the present inventor that the subject's breathing may affect the intra cuff pressure. Therefore, the pressure variation pattern can be analyzed in terms of the periodicity and/or amplitude in order to maintain adequate sealing without over-inflating the cuff. According to some embodiments of the present invention when the amplitude of the cuff pressure variation is above a predetermined pressure threshold (typically from about 14 mmHg to about 16 mmHg, e.g., about 15 mmHg) for a time period which is above a predetermined time threshold (typically from about 15 minutes to about 25 minutes, e.g., about 20 minutes), controller 120 instructs models 156 to reduce the cuff pressure, preferably gradually.

The correlation between the variations in cuff pressure and breathing cycle of the subject is optionally and preferably utilized for detecting occlusion also in the cuff inflation line. In these embodiments, controller 120 provides processing unit 116 with monitoring data pertaining to the cuff pressure as a function of time. Unit 116 analyzes the data and extracts respiratory features from the data as further detailed hereinunder.

In was found by the present inventor that lack of correlation between the cuff pressure variation and the respiratory rate, indicates that the cuff inflation line is occluded. Thus, according to some embodiments of the present invention when the unit 116 is unable to extract respiratory feature from the cuff pressure data, or when the extracted features do not correlate with a respiratory rate within a predetermined threshold (e.g., from 4 to 60, or from 10 to 20 breaths per minute for adult, and from 20 to 40 breaths per minute for a child or infant), controller 120 signals venting module 160 to force air or other gas into cuff inflation line 106c, so as to clear the occlusion.

In some embodiments of the present invention air is forced into the cuff inflation line 106c at a series of time points as a prevention procedure for preventing occlusion in line 106c. The series of time points can be predetermined or adapted during the operation of the system. For example, after detection of occlusion in line 106c, the rate at which the prevention procedure is executed can be increased. Typically, the prevention procedure is executed at least every 2 hours. A representative example for this procedure is provided in the Examples section that follows.

In some embodiments of the present invention at least one of the profile, amplitude, and frequency characterizing air forced into the cuff inflation line 106c is selected by the operator. The amplitude can be selected from the range of atmospheric pressure to about 80 $cmH_2O$; the profile can be selected from several types of profiles, including, without limitation, a ramp, a step function and random; and the frequency can be selected from a range of from about 1 to about 5 Hz. For example, the maximal pressure can be about 60 cm $H_2O$ of a step function at frequency of about 3 Hz.

In experiments performed by the present Inventors, it was found that large-amplitude variations in the cuff pressure may produce temporal wrinkles or folds on the outer wall of the cuff, and that such wrinkles or folds can be temporarily occupied by secretions, which may move along the wall towards the lungs. The present inventors also found that when the variations in cuff pressure are sufficiently small, formation of wrinkles or folds on the outer wall of the cuff is reduced or even prevented. Thus, in some embodiments of the present invention controller 120 operates cuff inflation module 156 such as to maintain a generally constant (e.g., within +/−1 mmHg) cuff pressure as a function of the time. In predetermined time intervals, controller 120 interrupts the maintenance of constant cuff pressure so as to allow for larger variations in the cuff pressure to occur. In these intervals, cuff pressure data can be used by unit 116 for the purpose of calculating various quantities, such as tracheal pressure, breathing frequency, obstruction level of main lumen 202 of device 102 and resistance of main lumen 202 to flow, and/or for detecting various events such as, but not limited to, occlusions in the cuff inflation line, puncture or rupture in the wall of the cuff, patient coughing, patient's pulmonary reflex events detected in assist ventilation and the like. Unit 116 can also provide, e.g., via display 124, an estimated prediction of the subject's spontaneous initiation of inhale and exhale events, and/or the subject's pulmonary power as function of time. Procedure for such calculations and detection are described hereinbelow.

In some embodiments of the present invention system 100 comprises an additional suctioning module 155 which generally serves for automatically removing lung secretions from the lower part of the trachea near or at the lungs, and is preferably in fluid communication with vacuum connector 134 so that the suctioning operation is facilitated by the under pressure at connector 134. It is to be understood that although modules 154 and 155 are shown as separate modules, this need not necessarily be the case, since, for some applications, it may not be necessary for the suction operations above and below the cuff to be perfumed by separate modules. Thus, in some embodiments, module 154 performs also the operations described herein with respect to module 155. In these embodiments, system 100 optionally includes only one suctioning module 154.

Module 155 can comprise a pressure regulator and/or a flow meter (not shown). The pressure regulator controls the suctioning vacuum applied by module 155, and the flow meter measures the flow generated by the suctioning operation.

A patient connected to a ventilator requires periodic removal of fluid from the trachea. The traditional practice in hospitals is to disconnect the ventilator from the patient, and to insert through the main lumen of the endotracheal tube a separate, small-diameter suctioning tube 106e (e.g., a catheter) which is used to remove the fluids from the trachea.

The medical literature distinguishes between two types of suctioning operations from the lower part of the trachea. "Deep suctioning" in which the suctioning operation is performed directly from the bronchi, and "shallow suctioning" in which the suctioning operation is performed at or immediately below the distal end of the endotracheal tube.

The present Inventors contemplate both embodiments in which the lung secretions are evacuated from the lower part of the trachea near or at the lung by deep suctioning, and embodiments in which the lung secretions are evacuated from the lower part of the trachea by shallow suctioning. Deep suctioning is typically executed using a separate external suction catheter 106e introduced into main lumen 202 of device 102. Shallow suctioning can be executed using embedded suctioning line 106d without the need to manually introduce an additional suctioning catheter each time a suction operation is executed. Optionally and preferably, the shallow suctioning is executed without ceasing the ventilation.

In various exemplary embodiments of the invention suctioning module 155 is employed for a shallow suctioning operation, for example, through lumen 205 and line 106d wherein the lung secretions enter lumen 205 through opening 219 which is in close proximity to the distal end of endotracheal tube device 102.

Traditionally, shallow suctioning has been less preferred over deep suctioning due to the insufficient efficiency of the shallow suctioning, wherein inadequate removal of lung secretions resulted in frequent tube blockage.

In various exemplary embodiments of the invention main controller 120 synchronizes the shallow suction operation with the breathing cycle of the subject and/or the tracheal pressure. In these embodiments, controller 120 receives from unit 116 data indicative of the breathing cycle and/or tracheal pressure, and signals module 155 to perform the suctioning operation based on the data. Preferably, controller 120 signals module 155 to perform the suctioning operation during the exhale phase of the breathing cycle, e.g., from the onset of the exhale period to the end of the exhale period. The suctioning can be performed for each exhale period or once every several (e.g., 3, 4 or 5) exhale periods as desired.

Unit 116 can identify the exhale period by receiving from controller 120 monitoring data pertaining to the cuff pressure as a function of time and analyzing the data so as to extract respiratory features, for example, exhale and/or inhale periods. Representative processing techniques useful for extracting respiratory features and calculating tracheal pressure are provided hereinunder, and experimental examples are provided in the Examples section that follows. The onset of the exhale phase typically occurs immediately after the cuff or tracheal pressures reach a local maximum (reflecting lungs maximal pressure when there is no flow is the same like ventilator pressure).

The advantage of synchronizing the suctioning operation with the exhale phase is that there are two contributions to the suction force, an artificial contribution from the under-pressure generated by module 155, and a natural contribution from the work done by the lungs during exhale, not exercising contradictory pressures to patient pulmonary reflexes.

In some embodiments of the present invention the under-pressure applied by module 155 is dynamically adapted, responsively to the cuff pressure drop during exhale.

Preferably, the adaptation of under-pressure is such that the resulting suctioning force is maintained generally constant (e.g., within 20%) throughout the shallow suction operation. Thus, when the natural contribution to the suctioning is increased, the artificial contribution is reduced and vice versa. Since the tracheal pressure varies during exhale, the present embodiments contemplate variation of the applied under-pressure during the suctioning. It is recognized by the present inventors that the use of high vacuum adapted pressure to exhaled pressure throughout the exhale period does not affect alveoli, since it has only a local effect on exhaled air near the distal end of tube due to the small aperture of the aspiration opening and the low regulated vacuum pressure levels used compared to deep suction (e.g., −150 mmHg compared to −300 mmHg).

Preferably, the under-pressure applied for suctioning is adapted such that the effective under-pressure at the distal end of the endotracheal tube (namely the combined effect of lungs work and artificial suction) is from about 0 mmHg to about −250 mmHg during the entire suctioning phase.

In some embodiments of the present invention, at the end of the exhale phase, and before next inhale phase of the breathing cycle, the applied under-pressure is selected so as to trigger a cough effect. This can be done by applying pulsating high vacuum levels. This operation can be repeated every several (e.g., 3, 4 or 5) breathing cycles.

In embodiments in which deep suction is employed, a separate external fluid line 106e is introduced into the main lumen 202 of device 102, such that its distal end is positioned beyond the distal end 214 of device 102 toward the lungs (according standard of care 1-2 cm above the carina). The proximal end of line 106e is connected to panel 108 as illustrated in FIG. 1. Optionally and preferably, main controller 120 operates module 155 similarly as described above with respect to the shallow suction operation. Thus, for example, main controller 120 can synchronize the deep suction operation with the breathing cycle of the subject and/or the tracheal pressure, wherein module 155 performs the deep suctioning operation through line 106e based on data indicative of the breathing cycle and/or tracheal pressure, as further detailed hereinabove. Main controller 120 can signal module 155 to perform the deep suctioning operation during the exhale phase of the breathing cycle. Main controller 120 can dynamically update the under-pressure applied by module 155, responsively to the cuff pressure drop during exhale. In an embodiment of the invention, main controller 120 adapts the under-pressure such that the resulting suctioning force is maintained generally constant (e.g., within 20%) throughout the deep suction operation. Main controller 120 can adapt the under-pressure such that the effective under-pressure at the distal end of line 106e is from about 0 mmHg to about 300 mmHg during the entire suctioning phase. This can be done by applying pulsating high vacuum levels, for example, every several breathing cycles.

Exemplary Processing Unit

Processing unit 116 is configured to instruct control unit 118 to execute operations, via main controller 120, including, e.g., one or more of the operations described above, according to program instructions corresponding to a dedicated algorithm devised by the inventors of the present invention. Processing unit 116 is preferably also configured for recording on a memory medium data calculated by unit 116 or received from controller 120 or from an external source (via panel 126).

Representative of parameters that can be recorded by unit 116 including, without limitation, events chronology, cuff pressure, cuff leak, occlusion of one or more of the fluid lines, lung compliance, lung resistance, alerts, and one or more statistical analysis reports in the frequency or time domains pertaining to monitored cuff pressure control, coughing and other events.

The recorded data can be displayed on display device 124, for example, upon a specific request by the operator. The recorded data can also be transmitted or downloaded to an external system having processing capabilities. The recorded data can also be used by unit 116 or the physician observing the data in various calculations or estimations that may require use of pre-recorded data. For example, the recorded data can be used for analyzing trends of lungs compliance and resistance, thereby reducing the risk of abnormal lung conditions (e.g., acute respiratory distress syndrome, acute lung injury, ventilator-associated lung injury). Such analysis can include calculation of the resistance to flow in the main lumen of device 102 based on the history of tracheal and ventilator pressures. The resistance to flow is typically expressed in pressure units which describe the pressure drop along the length of the main lumen device 102. The resistance to flow history can be used, to calculate lungs compliance in order to alert development of Ventilator Associated Lung Injuries.

In various exemplary embodiments of the invention control unit 118 executes operations, which comprise a sequential and periodic transition between three or more phases, as will now be described with reference to a flowchart diagram illustrated in FIG. 3.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

In various exemplary embodiments of the invention processing unit 116 begins by performing a self test 300, in which the operability of the various components of system 100 is verified. When unit 116 identifies malfunction in one or more of the components, unit 116 issues an alert signal, e.g., via display 124 and/or electroacoustic device 130. Depending on the type of malfunction, unit 116 may, in some embodiments, stop all operations of system 100. Preferably, unit 116 performs the self test whenever system 100 is powered on.

Optionally and preferably unit 116 also executes a safety procedure 302 at which unit 116 verifies that the cuff provide adequate sealing and that the fluid lines are clear. Unit 116 can execute the safety procedure upon manual intervention by the operator and also responsively to situations that may be identified during other phases of the operations, as further detailed hereinunder.

In various exemplary embodiments of the invention unit 116 execute, in a sequential and periodic manner, a main phase 304, a primary draining phase 306 and a primary cuff sealing phase 308. Typically, but not necessarily, the main phase is executed for a period of from about 15 to about 25 minutes, the primary draining phase is executed following every execution of the main phase, and the primary cuff sealing phase is executed following every execution of the primary draining phase. Other time periods and orders of execution are not excluded from the scope of the present invention.

The main phase 304 generally sustains the operation of the system during the ventilation of the subject. Hence, the main phase can include suctioning of tracheal secretions from the subglottal region in the trachea, and venting of fluid lines. The main phase preferably also includes adjustment of cuff pressure. For example, during the main phase 304, control unit 118 can perform a suctioning operation at predetermined time intervals (e.g., about every 2 minutes) through one of fluid lines 106a and 106b. Control unit 118 can also perform suctioning and venting operations for predetermined time periods.

In between consecutive Main Phase processes there are times that optionally are used for lungs shallow or deep suction processes alternately with suction processes as performed in the Main Phase. Since these periods are characterized by no operations that can create noisy reflections of the cuff, they are used to derive data of cuff pressure analyzed for calculating tracheal pressure and ETT occlusion parameters, and to detect cuff inflate line occlusion as well.

A general description of main phase 304, according to some embodiments of the present invention, is illustrated in FIG. 4A. As illustrated at 402, a suctioning operation through fluid line 106b can accompany, preferably in a simultaneous manner, a venting operation through fluid line 106a for a predetermined time period (e.g., 15-25 seconds). Thereafter (404), a pressure release stage can be employed for a predetermined time period (e.g., 5-10 seconds) so as to allow for tissue relaxation. A first cuff pressure adjustment 406 can then be employed. A complementary operation 408 can then be similarly executed (suctioning operation through fluid line 106a accompanying a venting operation through fluid line 106b) with a pressure release stage 410 thereafter. Following these operations, a second cuff pressure adjustment 411 can then be employed.

The first 406 and second 411 cuff pressure adjustments preferably include a leak detection procedure. In these embodiments, unit 116 can instruct control unit 118 to perform the leak detection procedure, for a predetermined time period (e.g., 15-25 seconds), through any of lines 106a and 106b, for example, by monitoring the level of the leakage-indicating measure (e.g., $CO_2$) in the respective line 106a. Preferably, the leak detection procedure is performed through both lines 106a and 106b in a sequential manner. For example, in some embodiments of the invention the adjustment 406 is responsive to leak detection procedure performed through line 106a for, and the adjustment 411 is responsive to leak detection procedure performed through line 106b. If a leak above a predetermined level is detected, control unit 118 preferably ceases the main phase 304 and switches directly to the primary cuff sealing phase 308.

Any of operations 402 and 406 optionally comprises an occlusion detection procedure. Generally, occlusion can be detected by operating suctioning module 154 to apply vacuum to the respective fluid line and measures the resulting flow wherein a flow level which is below a predetermined threshold (e.g., 15%-25% of the full flow capacity) indicates the existence of occlusion. The occlusion detection procedure can be executed through any of lines 106*a* and 106*b*. Preferably, the procedure through both these lines in a sequential manner. If an occlusion is detected, suctioning module 154 iteratively and gradually increases the suction force applied to the occluded line, wherein after each increment module 154 detects whether or not the line is still occluded. The iterative process continues until a stop criterion is met. For example, the iterative procedure can continue until the line is cleared, or until the level of occlusion is reduced, or until the under-pressure applied for suctioning reaches a predetermined threshold. Once the occlusion is reduced or cleared, control unit 118 optionally and preferably executes a rinsing and venting procedure through the previously occluded line.

The main stage 304 can be repeated several times. For example, as illustrated in FIG. 4A, the main stage 304 can loop back to 402 after the completion of cuff pressure adjustment 411. Typically, main stage 304 is repeated every 1-5 minutes or about 3-6 times over a period of 15-25 minutes. A more detailed description of a main phase suitable for the present embodiments is provided in the Examples section that follows (see FIGS. 5A and 5B).

The primary draining phase 306 serves for draining, rinsing and clearing the fluid lines following the completion of one or more cycles of the main phase. A general description of phase 306 is illustrated in FIG. 4B. Broadly speaking, the primary draining phase 306 can comprise an occlusion detection procedure 412 through each of lines 106*a* and 106*b*, as further detailed hereinbelow. Following the occlusion detection procedure 412, the lines are rinsed 414 in a staggered manner by rinsing fluid. The rinsing is followed by a simultaneous suctioning and venting operation 416. This is preferably performed several times. In various exemplary embodiments of the invention the suctioning operation is performed intermittently with controlled pressure release periods 418 between successive suction stages. For example, phase 306 can include, for each of lines 106*a* and 106*b*, several (e.g., 3-10) cycles in which suction is applied for about 5-15 seconds, and is followed by a pressure release period of about 5-10 seconds.

Figure 6A:
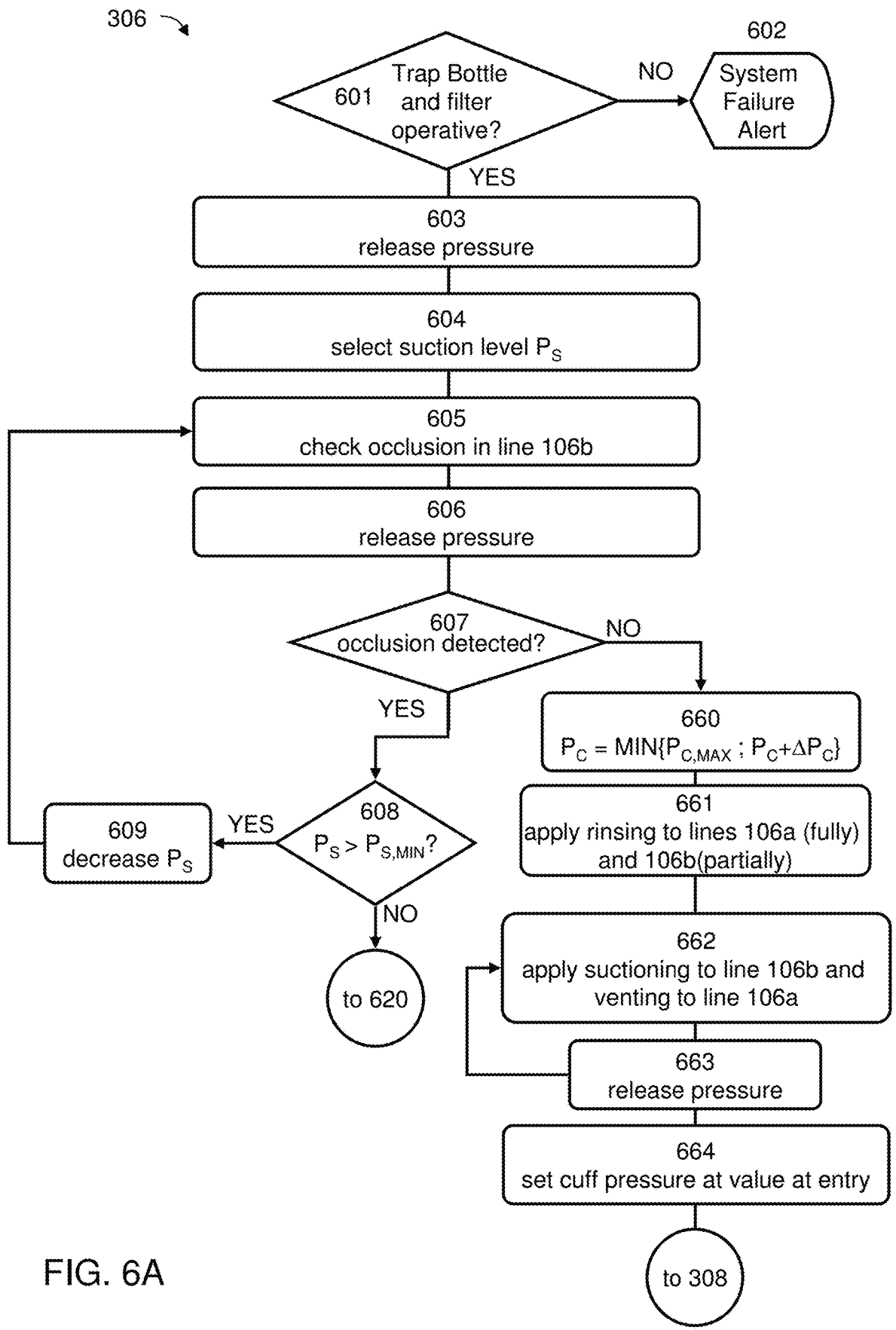
FIGS. 6A and 6B are flowchart diagrams describing a more detailed procedure suitable to be executed, at least in part, during the primary draining phase, according to some embodiments of the present invention.
Figure 6B:
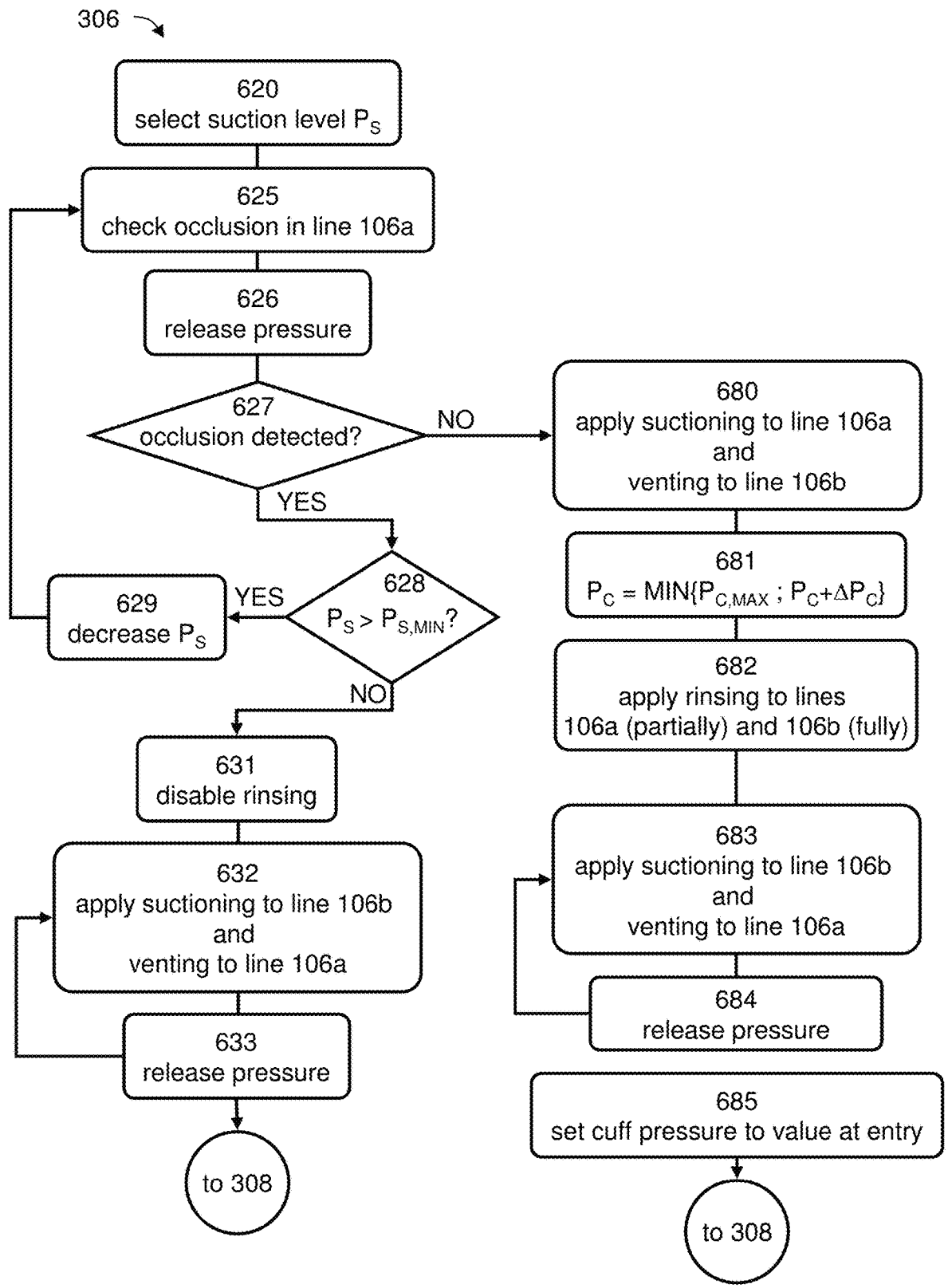

A more detailed description of a primary draining phase suitable for the present embodiments is provided in the Examples section that follows (see FIGS. 6A-6B).

The primary cuff sealing phase 308 serves for ensuring that the cuff provides adequate sealing with minimal or close to minimal pressure. A general description of phase 308 is illustrated in FIG. 4C. Broadly speaking, the primary cuff sealing phase 308 can begin with a procedure 422 in which suction is applied to one line and venting is applied, preferably synchronously, to the other line.

Phase 308 can also include an occlusion detection procedure 424.

Phase 308 preferably proceeds to 426 at which existence of leakage or lack thereof is detected. Thereafter, the cuff pressure is adjusted. Typically, the cuff pressure is increased when a leakage is identified and decreased otherwise. Optionally and preferably the rate characterizing the intra cuff pressure increment is higher than the rate characterizing the intra cuff pressure decrement.

The increment of cuff pressure can be performed using iterative process, wherein the level of leakage is reassessed at each iteration step. In some embodiments of the present invention the rate of increment is selected based on the level of leakage. For example, for relatively low leakage, the cuff pressure can be increased linearly as a function of the iteration index (fixed step size), and for higher leakage the cuff pressure can be increased non-linearly as a function of the iteration index (variable step size). When non-linear increment is employed, the step size is preferably a function of the cuff pressure. Optionally, the non-linear increment is characterized by a concave function of the iteration index.

The decrement of cuff pressure can also performed using iterative process, wherein the level of leakage is reassessed at each iteration step. A reduced rate of decrement is optionally and preferably achieved by decreasing the cuff pressure selectively with respect to the iteration index, wherein for at least some iteration steps, the cuff pressure is not decreased at all. Thus, for example, for the ith iteration step of the decrement process, the cuff pressure can be decreased if and only if the result of the modulo operation i mod m equals 0, where m is a positive integer greater than 1 (e.g., m=2 or m=3). The rate of decrement at each of the selected iteration steps can also be controlled. Typically, for higher cuff pressures a higher decrement step size in cuff pressure is employed. In these embodiments, unit 116 employs a thresholding procedure. For example, when the cuff pressure is above a predetermined cuff pressure threshold P1, a first pressure step size $\Delta P_{C1}$ is selected, and when the cuff pressure is not above P1, a second pressure step size $\Delta P_{C2}$ is selected.

A typical value for P1 is from about 15 mmHg to about 20 mmHg, e.g., about 18 mmHg, a typical value for $\Delta P_{C1}$ is from about 0.5 mmHg to about 1.5 mmHg, e.g., about 1 mmHg, and a typical value for $\Delta P_{C2}$ is from about 0.3 mmHg to about 0.7 mmHg, e.g., about 0.5 mmHg.

A more detailed description of a primary cuff sealing phase suitable for the present embodiments is provided in the Examples section that follows (FIGS. 7A-7E).

In some embodiments of the present invention processing unit 116 is configured for determining cuff rupture, and issuing an alert signal if cuff rupture is determined. In these embodiments unit 116 receives from controller 120 cuff pressure data and analyzes variations in cuff pressure to identify cuff rupture. Typically, cuff rupture event is accompanied by low cuff pressure and/or an abrupt drop in cuff pressure. Thus, in some embodiments of the present invention processing unit 116 determines cuff rupture existence if the cuff pressure persists generally without responding to induced inflated volumes of air (e.g., 2-3 mmHg). When cuff rupture is identified, unit 116 preferably issues an alert signal, e.g., via display device 124 and/or electroacoustic device 130 and/or panel 126.

The cuff pressure data from controller 120 can also be used for identifying cuff puncture. In these embodiments unit 116 searches for a statistically significant frequency of pressure spikes, and determines cuff puncture existence if such statistically significant frequency is found. Unit 116 can analyze the data using any type of signal processing suitable for identifying patterns in a signal. For example, unit 116 can apply a mathematical transform to the frequency domain and perform the analysis at the frequency domain, as known in the art.

One such analysis is Fast Fourier transform (FFT) analysis, which is a well-understood and well-utilized analysis tool. Many efficient hardware and software algorithms have been developed and implemented which can perform FFT analysis on a time-domain signal segment. Generally, an FFT algorithm approximates a time domain signal segment with a series of sinusoidal functions. Each function in the series has a certain amplitude, frequency and phase. If these functions are summed in the series point-for-point over time, the resultant time-varying signal resembles the original time domain signal segment analyzed. Other algorithms suitable for extracting respiratory features from the data including, without limitation, Goertzel algorithm, Z-transform algorithm, discrete Fourier transform, Laplace transform, and the like.

Processing unit 116 can search for predetermined frequency range over the data. For example, the data can be divided into epochs of predetermined duration (e.g., 25-35 second epochs), wherein the characteristic frequency of each epoch is extracted. Unit 116 can then count the percentage $Y_F$ of epoch whose characteristic frequency $F_e$ satisfies $F_e \geq F_p$, where $F_p$ is a predetermined frequency threshold. If $Y_F > Y_p$, where $Y_p$ is a predetermined percentage threshold, unit 116 can determine that the cuff pressure unstable and issue an alert signal, e.g., via display device 124 and/or electroacoustic device 130 and/or panel 126. It was found by the present inventors that an unstable cuff pressure is indicative of cuff puncture, rupture, coughing, and weaning events. Thus, in some embodiments of the present invention when $Y_F > Y_p$ unit 116 issues an alert signal that the cuff is punctured.

Processing unit 116 can also receive from controller 120 cuff pressure data, identify peaks in the frequency dependence of a representative quantity of the cuff pressure (e.g., amplitude, amplitude square, power), and determine cuff puncture responsively to the identified peaks. One type of frequency dependence analysis is power spectrum density. The power spectrum density can be calculated as the ratio $A_e^2/F_e$, where $A_e$ and $F_e$ are the characteristic amplitude and frequency of the eth epoch. In some embodiments of the present invention unit 116 determines that there is a cuff puncture when the power spectrum density is below a predetermined threshold. Representative of such threshold is from about 0.001 mmHg$^2$/Hz to about 0.1 mmHg$^2$/Hz.

A representative example demonstrating the detection of cuff puncture is provided in the Examples section that follows.

In some embodiments of the present invention processing unit 116 is configured for extracting respiratory features from cuff pressure data provided by controller 120. Unit 116 analyzes the data using any type of signal processing suitable for identifying patterns in a signal. Typically, the analysis includes transforming the signal from controller 120, which is in the time domain, into the frequency domain to determine its frequency content. Any technique for transforming a signal to the frequency domain can be employed, including, without limitation, FFT, Goertzel algorithm, Z-transform algorithm, discrete Fourier transform, Laplace transform, and the like.

Once a breathing pattern is identified in the signal, unit 116 uses the pattern for extracting respiratory features, such as exhale and inhale periods, breathing amplitude (which may be expressed, for example, in units of pressure), and the like. Respiratory features can also be predicted, based on previous respiratory features extracted from the data. In some embodiments, an identified pattern is processed to extract repetitive features present within the pattern, and an estimated prediction is generated based on the extracted repetitive features. For example, when a repetitive feature corresponds to an inhale or exhale event, unit 116 can predict the occurrence of the next inhale or exhale event or the next series of inhale or exhale events, based on the repetition rate of the extracted repetitive feature. Similarly, when the repetitive feature corresponds to the subject's pulmonary power, unit 116 can predict the pulmonary power as a function of the time based on the repetition rate of the extracted repetitive feature.

The cuff pressure data from controller 120 can additionally or alternatively be analyzed, e.g., via FFT, PSD or any other data analysis technique for the purpose of calculating blood pulse wave characteristics. It was undependably found by the present inventors that due to the proximity of the arterial vasculature to the tracheal tissue, the blood pulse wave induces pressure variations on the cuff. The present inventors demonstrated that the frequency content of the cuff pressure data includes frequencies which are characteristic to the blood pulse wave. Thus, in various exemplary embodiments of the invention the processing unit 116 analyzes the cuff pressure data to determine the frequency content of the data. From the frequency content, processing unit 116 extracts frequencies which are within a predetermined range of frequencies, and estimates, based on the extracted frequencies, one or more blood pulse wave characteristics. Unit 116 can transmit the estimated blood pulse wave characteristics to display device 124 or communication panel 126.

For example, processing unit 116 can identify peaks in the frequency dependence of a representative quantity of the cuff pressure (e.g., amplitude, amplitude square, power). The frequency or frequencies at the identified peaks can then be compared to predetermined frequency range, to determine which of the identified peaks is at a frequency that is characteristic to the blood pulse wave. Typically, the predetermined frequency range is characterized by a lower frequency bound of from about 1 Hz to about 1.2 Hz and a higher frequency bound of from about 1.5 Hz to about 2 Hz.

The peak or peaks at the frequencies within the predetermined range can be analyzed for estimating the blood pulse wave characteristics. In some embodiments of the present invention the blood pulse rate is determined from the frequency itself, and the blood pressure is estimated determined from the area of the peak. For example, when the analysis comprises PSD in units of squared pressure per unit frequency, the square root of the peak's area can be used as an estimate of the blood pressure. The analysis can also be performed both in the frequency domain and in the time domain, thus allowing estimating both the systolic and diastolic blood pressure. In various exemplary embodiments of the invention a correlating function is employed for estimating the blood pressure based on the pressure obtained from the peak analysis. Such correlating function can be an analytical function or a lookup table.

A correlation function suitable for the present embodiments can be of the form:

$$P_{cuff} = P_{base} + K_1 * P_{tr} + K_2 + K_3 * (\text{Blood Pressure}),$$

where $K_1$, $K_2$ and $K_3$ are experimentally derived constants, $P_{base}$ is the baseline pressure of the cuff and $P_{tr}$ is the tracheal pressure.

In some embodiments of the present invention the Blood Pressure is normalized by the Systolic Blood Pressure, and the correlation function has the form:

$$P_{cuff} = P_{base} + K_1 * P_{tr} + K_2 + K_3 * (\text{Blood Pressure})/(\text{Systolic Blood Pressure}).$$

A representative example of cuff pressure analysis for the purpose of estimating blood pulse wave characteristics is provided in the examples section that follows.

The cuff pressure data from controller 120 can also be used for identifying coughing events. In these embodiments, unit 116 preferably used the extracted respiratory pattern, wherein a deviation in the data from the respiratory pattern over a sufficiently long time period (e.g., above 120 seconds) is identified by unit 116 as a coughing event. Unit 116 can then record the event for further use. A representative example of a procedure for identifying coughing events is provided in the Examples section that follows.

The cuff pressure data from controller 120 can additionally or alternatively be analyzed, e.g., via FFT, PSD or any other data analysis technique for identifying other events. Generally, any event which is characterized by a frequency which is sufficiently above from the breathing frequency (0.066 HZ-1 Hz). Representative examples of such additional events, include, without limitation, cuff puncture, cuff rupture, weaning, freedom of sedation periods, and treatment disturbances that evoke patient restlessness replicated as noisy cuff, contrarily lack of the breathing signal.

The present inventors also contemplate embodiments in which the closed loop control over the cuff pressure is temporarily ceased. In these embodiments, processing unit 116 monitors variations in the cuff pressure, and particular the baseline pressure of these variations. If unit 116 identifies an abrupt increase in the baseline pressure, controller 120 preferably ceases the control over the cuff pressure for a predetermined period (e.g., from about 2 to about 10 seconds, e.g., about 5 seconds) thereby allowing a settling time. Thereafter, controller 120 decreases the cuff pressure to a predetermined pressure. During the cessation of control, unit 116 optionally and preferably continues to monitor the cuff pressure. If unit 116 identifies an abrupt decrease in the baseline pressure, controller 120 preferably increases the pressure to a predetermined level, with minimal or no delay (e.g., within 1 second or less).

In some embodiments of the present invention processing unit 116 is configured for assessing the tracheal pressure of the subject. Optionally, the tracheal pressure is assessed as a function of the time (continuously or repeatedly). Unit 116 can transmit the tracheal pressure to display device 124 or communication panel 126. For example, in some embodiments, the assessed tracheal pressure is displayed as a graph which is updated during the ventilation of the subject.

The inventors found that when the inflation of the cuff is dynamically adjusted to ensure cuff sealing, the cuff pressure within the cuff is correlated to the tracheal pressure of the intubated subject.

The assessment of tracheal pressure can be done in more than one way, e.g., as described in International Publication No. WO2010/046874, assigned to the same assignee as the present application and being incorporated by reference as if fully set forth herein. Some preferred processing techniques suitable for assessing the tracheal pressure will now be explained.

In some embodiments of the present invention the ventilation pressure $P_V$ of the breathing gas is varied, so as to change the flow value F of the breathing gas within the main lumen of the endotracheal tube device. This can be done by controlling the ventilator machine (not shown) which supplies the breathing gas to the endotracheal tube. The variations of $P_V$ are preferably small, e.g., less than 20 mmHg, more preferably less than 15 mmHg, more preferably less than 10 mmHg. A response pressure $P_C$ within the cuff can then be monitored by controller 120 responsively to the variation of $P_V$. In various exemplary embodiments of the invention the variations in the pressure pulse above the baseline pressure $P_{baseline}$ within the cuff are monitored. Preferably, but not necessarily, the peak of the pressure pulse is monitored. It was found by the present inventors that variations in $P_V$ cause variations in the pressure peak within the cuff, and that the tracheal pressure correlates to these variations. Thus, in various exemplary embodiments of the invention $P_C$ is the peak of the pressure pulse above the baseline inflation pressure.

Unit 116 can then calculate the tracheal pressure using the variations of $P_V$, $P_C$ and F. In various exemplary embodiments of the calculation is executed repeatedly throughout the ventilation period (e.g., every 2 to 30 minutes).

The calculation of the tracheal pressure $P_{tr}$ can be according to the equation:

$$P_{tr} = P_V - KF^2,$$

where K is a coefficient given by:

$$K = (1 - \delta P_C/\delta P_V)/(2F\delta F/\delta P_V),$$

and the symbol $\delta$ represents a variation.

The second equation is derived from the first equation by differentiating both side of the equation with respect to $P_V$ and replacing $\delta P_{tr}/\delta P_V$ with $\delta P_C/\delta P_V$. It was found by the present inventors that $\delta P_{tr}/\delta P_V$ and $\delta P_C/\delta P_V$ are equivalent derivatives with high degree of accuracy.

An additional technique for assessing the tracheal pressure is based on the obstruction level of the main lumen of the endotracheal tube device. In these embodiments unit 116 estimates the obstruction level OL using the variations of $P_V$ and $P_C$. The obstruction level can be estimated using any formalism known in the art, including, without limitation, the techniques disclosed in Kawati et al., Anesthesia and analgesia, Vol. 103, No. 3, pp 650-657 (2006); Guttmann et al., Intensive Care Med 24, 1163-1172 (1998); and Schumann et al., Respiratory Physiology & Neurobiology 155, pp. 227-233 (2007). The obstruction level can also be estimated from a predetermined predicting function which depends solely on the derivative of $P_C$ with respect to $P_V$. Such function can be determined by experimentation. For example, several tubes with different obstruction levels can be subjected to the variation procedure described above such as to associate a derivative for each value of obstruction level. Subsequently a fitting procedure can be employed, and the output of fitting procedure can be used as a predicting function.

In some embodiments of the present invention the predicting function is a polynomial function, e.g., $OL = \Sigma_n c_n (\delta P_C/\delta P_V)^n$, where n=0, 1, . . . and $c_n$ are the coefficients of the polynomial function. Typical values for the first three coefficients are, without limitation, $c_0 = -142.81$, $c_1 = 672.5$ and $c_2 = -553$.

These values were obtained by experimentations performed by the inventors of the present invention, and yielded a Pearson's r of about 0.95, as described in International Publication No. WO2010/046874 supra.

It is to be understood, however, that the predicting function can also have a different form, e.g., a polynomial function of higher degree (third degree or higher) or a non-polynomial function, e.g., $\Sigma_n c_n (\delta P_C/\delta P_V)^{Xn}$, where Xn is a real number (not necessarily positive and not necessarily integer). Other forms, such as exponential and logarithmic or any combination of different forms are also contemplated and can be obtained by non-linear fitting procedure.

Once OL is known, unit 116 estimates the effective internal radius $r_{eff}$ of the endotracheal tube based on the value of OL and the internal radius r of the non-occluded endotracheal tube. For example, when OL is expressed in terms of percentage, $r_{eff}$ can be calculated according to the expression:

$$r_{eff} = \sqrt{1 - OL/100}.$$

Once $r_{eff}$ is known unit 116 preferably estimate a pressure drop $P_R$ (tube resistance), for example, using conventional fluid mechanics techniques. The pressure drop across the endotracheal tube depends upon the amount of flow through the tube. For example, for high Reynolds numbers (e.g., above 2000) $P_R$ can be calculated using the expression $P_R = FL\rho/(4\pi r_{eff}^z)$ where z is a real number satisfying 5>z>4 and F is the flow level of the breathing gas; and for low Reynolds numbers (e.g., under 2000), $P_R$ can be calculated using the expression $P_R = 8FL\eta/(\pi r_{eff}^4)$, where L is the length of the endotracheal tube, $\rho$ is the mass density of the breathing gas (typically about 1.299 Kg/m$^3$), and $\eta$ is the dynamic viscosity of the breathing gas (typically about 1.7894×10$^5$ N·s/m$^2$ at a temperature of about 20° C.). The Reynolds number Re can be calculated using the expression Re=2$\rho$v$r_{eff}/\eta$, where v is the average velocity of the breathing gas in the endotracheal tube. Both the velocity v and flow level F can be determined from the volume of breathing gas supplied by the ventilator. Thus, unit 116 preferably receive volumetric and flow rate data from the ventilator, e.g., via panel 126.

Generally, the flow level F is the derivative of the gas volume with respect to the time, and the velocity is the calculated flow level divided by the effective cross-sectional area $\pi r_{eff}^2$.

Once the pressure drop is estimated, unit 116 estimates the tracheal pressure, for example, by subtracting the pressure drop $P_R$ from the ventilation pressure $P_V$. In some embodiments of the present invention, unit 116 also takes into account a muscular contribution $P_M$ to the pressure in the estimation of the tracheal pressure.

In these embodiments, the tracheal pressure can be given by:

$$P_{tr} = P_V + P_M - P_R.$$

The muscular contribution can be estimated based on input from an external source, such as, but not limited to, a pressure sensor placed at an esophageal cuffed tube (see, e.g., U.S. Pat. Nos. 6,723,053 and 5,050,297), or a pressure transducer placed in the main lumen of the endotracheal tube. When unit 116 receives the input from a sensor in the esophageal tube, the received pressure can be used as the muscular contribution without further processing. When unit 116 receives the input from a sensor in the endotracheal tube, $P_M$ is preferably calculated using the expression:

$$P_M = P^0_{tr} + P_R - P_V,$$

where $P^0_{tr}$ is an initial tracheal pressure measured in the main lumen of the endotracheal tube.

Once $P^0_{TR}$ is measured, the pressure transducer can be pulled out to allow and the ventilation to continue without the transducer.

After several calculations of $P_{tr}$ (using any technique) unit 116 optionally and preferably calculates a direct relationship between $P_{tr}$ and $P_C$. For example, several (e.g., at least 3, more preferably at least 4, more preferably at least 5) values of $P_C$ and corresponding values of $P_{tr}$ can be recorded, and a fitting procedure can be employed to establish the direct relationship.

It was found by the inventors of the present invention that a direct relationship between $P_{tr}$ and $P_C$ which is based on pre-calculated values of $P_{tr}$ as described above can be used as a universal function for estimating the value of $P_{tr}$, during a prolonged period of time. In particular, the direct relationship can be used as a universal function when $P_C$ is the peak of the pressure pulse above the baseline inflation pressure, because when the pressure within the cuff reaches its maximum, there is no flow.

The direct relationship can be any type of function. It was found by the inventors of the present invention that a linear function is suitable to predict the value of $P_{tr}$ for a given value of $P_C$ at sufficient level of accuracy. Thus, in various exemplary embodiments of the invention the direct relationship is a linear relationship $P_{tr} = k_0 + k_1 P_C$, where $k_0$ and $k_1$ are two fitted coefficients characterizing the direct relationship. In this embodiment, the method can execute a linear regression algorithm for determining the values of the coefficients $k_0$ and $k_1$. Preferably, the direct linear relationship is calculated and employed for estimating the value of $P_{tr}$, while ensuring sealing of the trachea by the cuff at a cuff baseline pressure $P_{baseline}$ which is lower than or equals 15 mmHg. Yet, a higher value of baseline pressure is also contemplated. For example, in some embodiments, the cuff inflation is preferably such that the baseline pressure $P_{baseline}$ within the cuff is lower than or equals 25 mmHg.

In some embodiments of the present invention the direct linear relationship is calculated and employed for estimating the value of $P_{tr}$ for response pressure $P_C$ which is above a predetermined threshold, $P_{C,min}$. For example, $P_{C,min}$ can be $P_{baseline} + \Delta$, where $\Delta$ is from about 2 mmHg to about 10 mmHg, more preferably from about 5 mmHg to about 7 mmHg, e.g., about 6 mmHg.

In some embodiments of the present invention the relationship can be calculated for the specific endotracheal tube being used, particularly to the performable parameters characterizing the cuff (material, thickness, elasticity, permeability, etc.). In these embodiments, unit 116 stores in its memory several relationship schemes for several types of endotracheal tube. Via interface 128, the operator selects from an existing list (e.g., a list of brand names) the endotracheal tube being used for the particular subject, and unit 116 selects the appropriate relationship based on this input.

Typical values for $k_0$ and $k_1$ are, without limitation, $k_0 = 2.3915$ and $k_1 = 0.992$. These values were obtained by experimentations performed by the inventors of the present invention, and yielded a Pearson's $r^2$ of above 0.99. Further details are provided in the Examples section that follows.

Once the direct relationship is calculated, unit 116 can estimate the tracheal pressure using the direct relationship over a predetermined time-period. The time period during which the direct relationship is used to estimate the tracheal pressure can be relatively long and is preferably extended over many (e.g., at least 10, more preferably at least 50, more preferably at least 100) breathing cycles of the subject. In some embodiments of the present invention the predetermined time-period extends over several (e.g., from 2 to 4) hours.

The direct relationship can be recalculated, e.g., when the predetermined time-period is over or when the conditions justify such recalculation. For example, the direct relationship can be recalculated following adjustment of $P_{baseline}$ (e.g., when the method identifies a sealing failure, or when the method determines that sealing can be achieved with a lower baseline inflation pressure).

The tracheal pressure as estimated from the direct relationship can be outputted by the method in a form of a report, or it can be displayed using the display device, or transmitted to ventilator in order to exploit it by the ventilator control system. Preferably, the estimated tracheal pressure is displayed continuously during the ventilation of the subject. In some embodiments of the present invention the direct relationship and/or the coefficients characterizing this relationship are also displayed and/or outputted.

Between consecutive processes of suctioning tracheal secretions from the subglottal region in the trachea (above the cuff) there is optionally and preferably a period in which no such processes are performed. This is advantageous since it reduces the burden caused by frequent procedures such as rinsing, suction and venting. The present embodiments contemplate many other operations during these periods. For example, during these periods, the processing unit the preferably signals control unit to detect leakage (e.g., by measuring $CO_2$), a procedure which generally does not effect the intubated patient. During these periods, the processing unit can also signal the control unit to measure the Intra Cuff Pressure (ICP) for the purpose of identifying occlusion in the cuff inflation line as further detailed hereinabove. During these periods, the processing unit can also signal the control unit to assess the tracheal pressure, the obstruction level of the main lumen, as further detailed hereinabove. Another procedure which is contemplated during these periods is the aforementioned procedure of suctioning below the cuff. Additionally, these periods can be used for the patient's pulmonary reflexes as well as the pattern of reflected breathing on cuff to synchronize the ventilator.

Exemplary Operation Modes

System 100 may have several operation modes, which are optionally and preferably selectable by the operator via user interface unit 128.

In a first operation mode, referred to herein as "clinical mode," system 100 is connected to an endotracheal tube which is placed in the trachea of the subject and preferably performs at least some of the operations described in FIG. 3.

A second operation mode, referred to as "disinfection mode", is preferably selected while the system is not connected to an endotracheal tube placed in vivo. In this operation mode, a disinfection fluid is preferably introduced to all fluid conveying elements of system 100. Thereafter the disinfection fluid can be drained.

When pneumatic module 132 comprises disposable pipes, the disposable pipes can be replaced, and the disinfection mode can be skipped.

A third operation mode, referred to as "weaning mode", is preferably selected for subjects who are about to be disconnected from the ventilation machine. In this mode, system 100 monitors a predetermined cuff pressure. Preferably, in this mode the procedures that relate to one or more of: rinsing, venting, leak detection, and rupture/puncture detection are disabled. Suctioning can be disabled or optionally configured to mild suction (low vacuum levels).

A forth operation mode referred to as "Hold On", is preferably selected on disconnection from system or for subjects that are treated for cleaning, deep suctioning or other clinical operations that may excite an alert due to aborts created by moving patient.

The system of the present embodiments is optionally and preferably also configured for receiving, e.g., via user interface 128, user instructions to alter one or more particular procedures, or to force one or more particular procedures, or to repeat one or more particular procedures, or to cease one or more particular procedures, or to disable one or more particular procedures. For example, the operator can change, e.g, during the automatic operation of system 100, and force immediate rinsing, or immediate suction, or immediate venting, or immediate leak detection procedure via any of lines 106a and 106b. The operator can also request for a history report regarding any of the quantities measured and/or calculated by system 100. The operator can request the history to be presented as raw data or analyzed data. The operator can also indicate the type of presentation (e.g., graphical, numerical, as a function of the time, as a function of the frequency, etc.).

Exemplary Method

According to some embodiments of the present invention there is provided a method suitable for ventilating a subject. The method comprises, intubating the subject with a cuffed endotracheal tube device having at least a main tube, a cuff inflation line, a first fluid line and a second fluid line, connecting the main tube to a ventilation machine; and connecting the a cuff inflation line, the first fluid line and the second fluid line to a system, such as system 100 described above. The intubation can be via oral, nasal endotracheal intubation or tracheotomy. Optionally, the endotracheal tube device has at least one additional fluid line, in which case the method also includes connecting the additional fluid line(s) to the system.

According to some embodiments of the present invention there is provided a method suitable for determining cuff rupture in a cuffed endotracheal tube device introduced into the trachea of a subject. The method comprises monitoring cuff pressure in the cuff, searching for a statistically significant frequency of pressure spikes in the monitored cuff pressure, and determining that the cuff is ruptured if statistically significant frequency is found.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Exemplary Main Phase

Figure 5A:
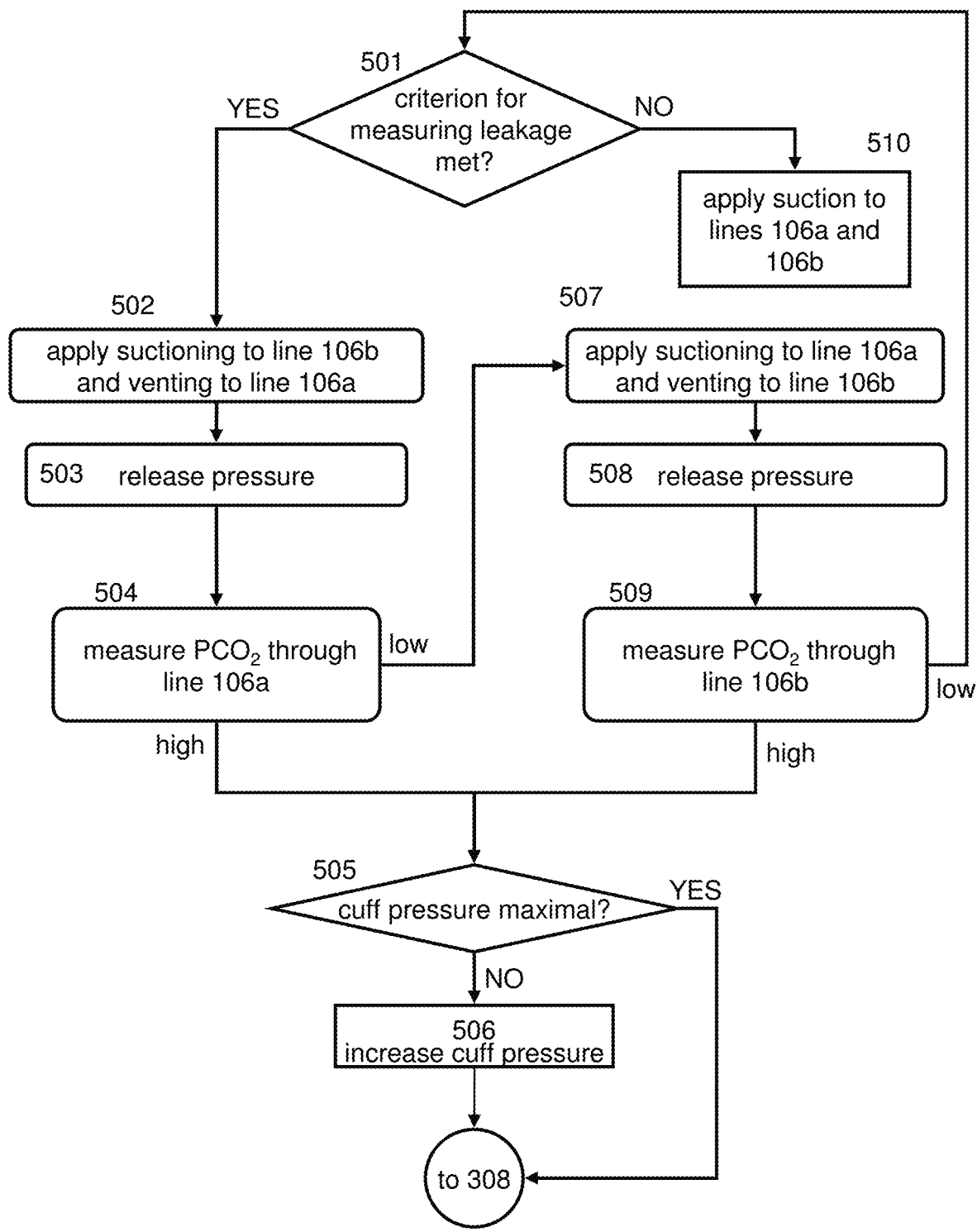
FIGS. 5A and 5B are flowchart diagrams describing a more detailed procedure suitable to be executed, at least in part, during the main phase, according to some embodiments of the present invention.
Figure 5B:
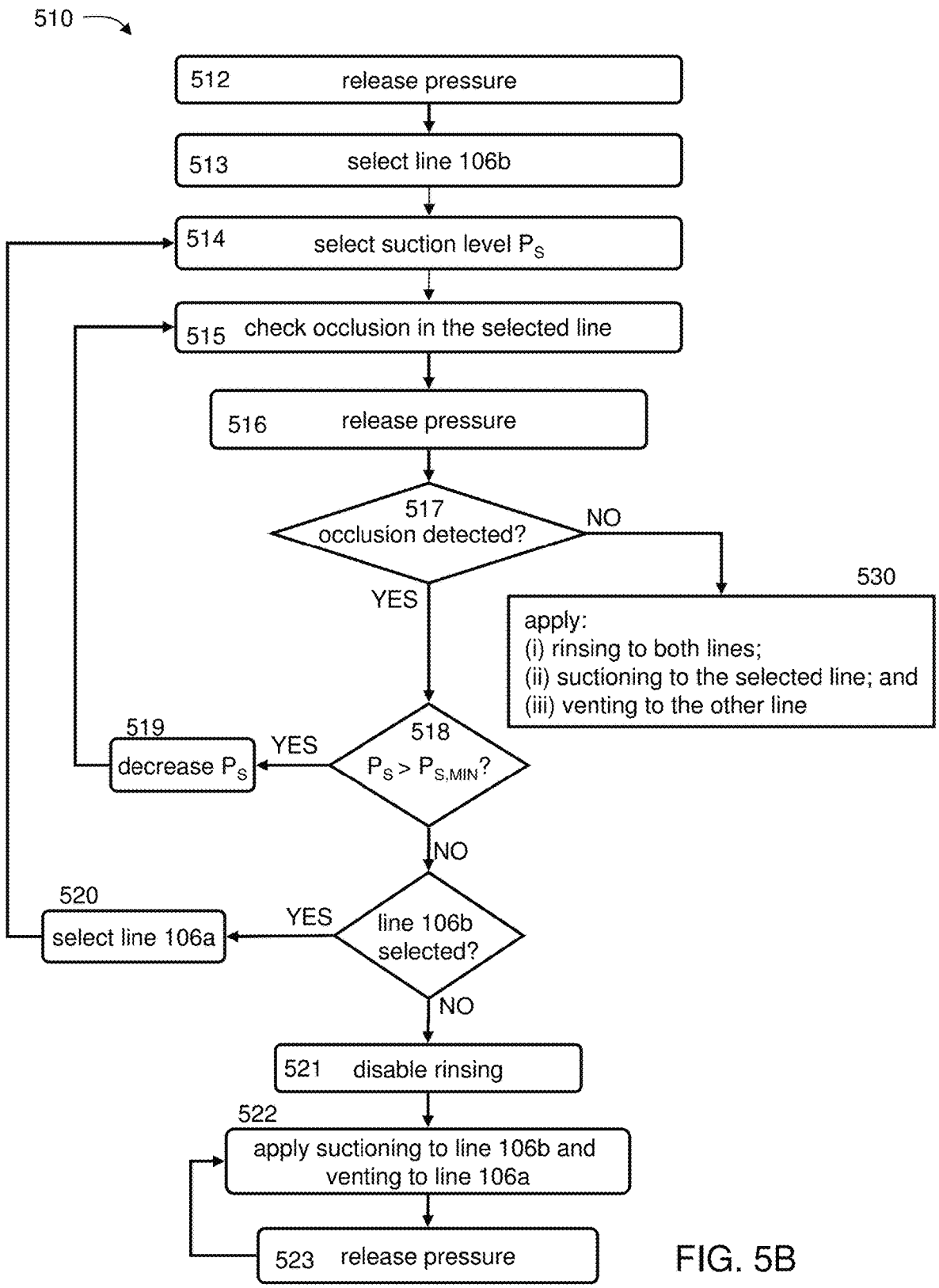

FIGS. 5A and 5B are flowchart diagrams describing a procedure suitable to be executed, at least in part, during main phase 304.

The procedure preferably executes decision 501 every 1-3 minutes (e.g., every 2 minutes). At decision 501 the procedure checks whether the current cycle of phase 304 includes measurement of secretion leakage past the cuff. This can be done by applying a predetermined criterion. For example, in some embodiments of the present invention, leakage measurement is executed prior to any nth suctioning operation, where n is a positive integer (e.g., n=1, 2, 3, . . . ). If the criterion is not met, the procedure continues to 510, otherwise the procedure continues to 502. At 510, suction is applied to lines 106a and 106b. A preferred procedure for operation 510 is described below with reference to FIG. 5B. Alternatively, instead of 510 the procedure can continue to primary draining phase 306.

At 502 the procedure performs a suctioning operation through line 106b and a venting operation through line 106a. Operation 502 is preferably performed for a predetermined time period which is typically from about 15 seconds to about 25 seconds, e.g., about 20 seconds. The procedure continues to 503 at which the pressure is released for a predetermined time period which is typically from about 5 seconds to about 10 seconds, e.g., about 7 seconds.

From 503 the procedure continues to 504 at which the partial pressure of carbon dioxide ($PCO_2$) or any other leakage indicative parameter is measured through line 106a. This measurement is preferably performed for a predetermined time period which is typically from about 15 seconds to about 25 seconds, e.g., about 20 seconds. If the leakage indicative parameter is above a predetermined threshold (e.g., about 2.0 mmHg, for the case of $PCO_2$) the procedure continues to decision 505, otherwise, the procedure continues to 507, at which the procedure performs a suctioning operation through line 106a and a venting operation through line 106b. Operation 507 is preferably performed for a predetermined time period which is typically from about 15 seconds to about 25 seconds, e.g., about 20 seconds. The procedure continues to 508 at which the pressure is released for a predetermined time period which is typically from about 5 seconds to about 10 seconds, e.g., about 7 seconds.

From 508 the procedure continues to 509 at which $PCO_2$ or any other leakage indicative parameter is measured through line 106b. If the leakage indicative parameter is above a predetermined threshold (preferably the same threshold used in 504) the procedure continues to decision 505, otherwise, the procedure loops back to 501. If the predetermined time for main phase 304 has passed, the procedure moves instead to primary draining phase 306 (not shown in FIG. 5A, see FIGS. 3, and 6A-B).

At decision 505, the procedure compares the intra cuff pressure $P_C$ to a predetermined maximal cuff pressure threshold $P_{C,MAX}$. If $P_C$ is below $P_{C,MAX}$, the procedure continues to 506 at which $P_C$ is increased, otherwise 506 is skipped. A typical value for the $P_{C,MAX}$ parameter is from about 35 mmHg to about 45 mmHg, e.g., 40 mmHg. A typical incremental step in $P_C$ is $0.5*(P_C+P_{C,MAX})$. From 505 or 506, the procedure exits and preferably continues to the primary cuff sealing phase 308.

FIG. 5B illustrates a preferred procedure 510 for detecting occlusion and treating the fluid lines 106a and 106b. Operation 510 is applied to lines 106a and 106b as follows. The pressure is released 512 for a predetermined time period which is typically from about 25 seconds to about 35 seconds, e.g., about 30 seconds. From 512, the procedure continues to 513 at which the procedure selects line 106b for further operations, and to 514 at which a suction level $P_S$ is selected. This can be done by setting the pressure regulator of suctioning module 154 to an appropriate vacuum (underpressure) level. Typically, the vacuum is set to a level corresponding to a pressure of from −130 mmHg to about −110 mmHg, e.g., about −120 mmHg.

From 514 the procedure continues to 515 at which the selected line is checked for occlusion, for a predetermined time period which is typically from about 15 seconds to about 25 seconds, e.g., about 20 seconds. The procedure continues to 516 at which the pressure is released for a predetermined time period which is typically from about 5 seconds to about 10 seconds, e.g., about 7 seconds. From 516 the procedure continues to decision 517 at which the procedure determines whether or not occlusion is detected in the selected line.

If occlusion is not detected, the procedure continues to 530 at which rinsing operation is applied to both lines 106a and 106b, suctioning operation is applied to the selected line, and venting operation is applied to the non-selected line.

If occlusion is detected the procedure continues to another decision 518 at which the procedure compares the suction level $P_S$ to a predetermined threshold $P_{S,MIN}$. If $P_S$ is above $P_{S,MIN}$, the procedure continues to 519 at which $P_S$ is decreased, otherwise the procedure continues to 520 at which line 106a is selected for further operations. A typical value for the $P_{S,MIN}$ parameter is from about −130 mmHg to about −110 mmHg, e.g., about −120 mmHg. A typical decrement step in $P_S$ is from about 15 mmHg to about 25 mmHg, e.g., about 20 mmHg. From 519 the procedure preferably loops back to 515. From 520 the procedure preferably loops back to 514 wherein the above operations are repeated for the now-selected line 106a.

Operations 521-523 below are preferably executed if line 106a is selected and the procedure determines, at decision 518, that $P_S$ is not above $P_{S,MIN}$.

At 521 the procedure disable rinsing module 152 for a predetermined maximal time period which is typically from about 2.5 hours to about 3.5 hours, e.g., about 3 hours. At 522 the procedure performs a suctioning operation through line 106b and a venting operation through line 106a. Operation 522 is preferably performed for a predetermined time period which is typically from about 8 seconds to about 12 seconds, e.g., about 10 seconds. At 523 the pressure is released for a predetermined time period which is typically from about 5 seconds to about 10 seconds, e.g., about 7 seconds. From 523 the procedure loops back to 522. Operations 522 and 523 are preferably performed several times, e.g., 3-8 times.

Example 2

Exemplary Primary Draining Phase

FIGS. 6A-6B are flowchart diagrams describing a procedure suitable to be executed, at least in part, during the primary draining phase 306.

With reference to FIG. 6A, the procedure optionally and preferably tests 601 the condition of the trap bottle sealing and/or existence of various filters (e.g., moisture absorbing filters and the like). If the procedure identifies malfunction in these elements, the procedure issues 602 a system failure alert and stops. The test 601 is preferably performed for a predetermined time period which is typically from about 15 seconds to about 25 seconds, e.g., about 20 seconds.

If the trap bottle and $CO_2$ filter are operative The pressure is released 603 for a predetermined time period which is typically from about 25 seconds to about 35 seconds, e.g., about 30 seconds. At 604 a suction level $P_S$ is selected. This can be done by setting the pressure regulator of suctioning module 154 to an appropriate vacuum (under-pressure) level. Typically, the vacuum is set to a level corresponding to a pressure of from −130 mmHg to about −110 mmHg, e.g., about −120 mmHg.

From 604 the procedure continues to 605 at which line 106b is checked for occlusion, for a predetermined time period which is typically from about 15 seconds to about 25 seconds, e.g., about 20 seconds. The procedure continues to 606 at which the pressure is released for a predetermined time period which is typically from about 5 seconds to about 10 seconds, e.g., about 7 seconds. From 606 the procedure continues to decision 607 at which the procedure determines whether or not there is an occlusion in line 106b. If occlusion is not detected, the procedure continues to 660 as further detailed hereinbelow.

If occlusion is detected the procedure continues to another decision 608 at which the procedure compares the suction level $P_S$ to a predetermined threshold $P_{S,MIN}$. If $P_S$ is above $P_{S,MIN}$, the procedure continues to 609 at which $P_S$ is decreased, otherwise the procedure continues to 620 as further detailed hereinbelow (FIG. 6B). A typical value for the $P_{S,MIN}$ parameter is from about −130 mmHg to about −110 mmHg, e.g., about −120 mmHg. A typical decrement step in $P_S$ is from about 15 mmHg to about 25 mmHg, e.g., about 20 mmHg. From 609 the procedure preferably loops back to 605.

At 660 the procedure increases the cuff pressure $P_C$. Preferably the increment is done so as not to exceed the value of $P_{C,MAX}$. Specifically, the procedure sets the value of $P_C$ to the minimal value of the pair $\{P_{C,MAX} \text{ and } P_C + \Delta P_C\}$, where $\Delta P_C$ is a predetermined increment threshold. A typical value for $\Delta P_C$ is from about 1 mmHg to about 10 mmHg, e.g., about 5 mmHg. From 660 the procedure continues to 661 at which the procedure applies staggered rinsing operation fully to line 106a and partially to line 106b as explained above. Preferably, at least part of the rinsing operation is performed in a staggered manner. A representative procedure for staggered delivery suitable for the present embodiment is detailed hereinafter (FIG. 8). The procedure continues to 662 at which the procedure performs a suctioning operation through line 106b and a venting operation through line 106a. Operation 662 is preferably performed for a predetermined time period which is typically from about 8 seconds to about 12 seconds, e.g., about 10 seconds. The procedure continues to 663 at which the pressure is released for a predetermined time period which is typically from about 5 seconds to about 10 seconds, e.g., about 7 seconds. The sequence of operations 662 and 663 can be repeated 3 to 8 times preferably 5 times. The procedure can then continue to 664 at which the cuff pressure value is set back to the entry value when entering 306. Thereafter, the procedure can exit, preferably to primary cuff sealing phase 308.

With reference to FIG. 6B, at 620 a suction level $P_S$ is selected, for example, as done at 604 above (e.g., −120 mmHg). From 620 the procedure continues to 625 at which line 106a is checked for occlusion, for a predetermined time period which is typically from about 15 seconds to about 25 seconds, e.g., about 20 seconds. The procedure continues to 626 at which the pressure is released for a predetermined time period which is typically from about 5 seconds to about 10 seconds, e.g., about 7 seconds. From 626 the procedure continues to decision 627 at which the procedure determines whether or not there is an occlusion in line 106a. If occlusion is not detected, the procedure continues to 680 as further detailed hereinafter.

If occlusion is detected the procedure continues to another decision 628 at which the procedure compares the suction level $P_S$ to $P_{S,MIN}$. If $P_S$ is above $P_{S,MIN}$, the procedure continues to 629 at which $P_S$ is decreased, otherwise the procedure continues to 631 (FIG. 6B) as further detailed hereinafter. A typical value for the $P_{S,MIN}$ parameter is from about −130 mmHg to about −110 mmHg, e.g., about −120 mmHg. A typical decrement step in $P_S$ is from about 15 mmHg to about 25 mmHg, e.g., about 20 mmHg.

If occlusion is detected the procedure continues to 631 at which the procedure disables rinsing module 152 for a predetermined maximal time period which is typically from about 2.5 hours to about 3.5 hours, e.g., about 3 hours. At 632 the procedure performs a suctioning operation through line 106a and a venting operation through line 106b. Operation 632 is preferably performed for a predetermined time period which is typically from about 8 seconds to about 12 seconds, e.g., about 10 seconds. At 633 the pressure is released for a predetermined time period which is typically from about 5 seconds to about 10 seconds, e.g., about 7 seconds. From 633 the procedure loops back to 632. Operations 632 and 633 are preferably performed several times, e.g., 3-8 times. Thereafter, the procedure exits, preferably to the primary cuff sealing phase 308.

At 680 the procedure performs a suctioning operation through line 106a and a venting operation through line 106b. Operation 680 is preferably performed for a predetermined time period which is typically from about 8 seconds to about 12 seconds, e.g., about 10 seconds. The pressure regulator of suctioning module 154 is preferably set to the entry value when entering 620. The procedure continues to 681 at which the procedure increases the cuff pressure $P_C$, preferably as done in 660. From 681 the procedure continues to 682 at which the procedure applies staggered rinsing operation fully to line 106b and partially to line 106a as explained above. Preferably, at least part of the rinsing operation is performed in a staggered manner. A representative procedure for staggered delivery suitable for the present embodiment is detailed hereinafter (FIG. 8).

The procedure continues to 683 at which the procedure performs a suctioning operation through line 106a and a venting operation through line 106b. Operation 683 is preferably performed for a predetermined time period which is typically from about 8 seconds to about 12 seconds, e.g., about 10 seconds. The procedure continues to 684 at which the pressure is released for a predetermined time period which is typically from about 5 seconds to about 10 seconds, e.g., about 7 seconds. From 684 the procedure loops back to 683. Operations 683 and 684 are preferably performed several times, e.g., 3-8 times. Thereafter, the procedure can continue to 685 at which at which the cuff pressure value is set back to the entry value when entering 306. The procedure can then exit, preferably to primary cuff sealing phase 308.

Example 3

Exemplary Primary Cuff Sealing Phase

FIGS. 7A-7D are flowchart diagrams describing a procedure suitable to be executed, at least in part, during the primary cuff sealing phase 308.

At 700 the procedure performs a suctioning operation through line 106a and a venting operation through line 106b. The procedure continues to 701 at which the trap line 137 is cleared and the vacuum in the trap bottle 138 is released. Operation 701 is preferably performed for a predetermined time period which is typically from about 10 seconds to about 20 seconds, e.g., about 15 seconds. The procedure continues to 702 at which $PCO_2$ or any other leakage indicative parameter is measured through line 106a. This measurement is preferably performed for a predetermined time period which is typically from about 35 seconds to about 45 seconds, e.g., about 40 seconds.

If the leakage indicative parameter is above a predetermined threshold (e.g., about 2 mmHg, for the case of $PCO_2$) the procedure continues to 740 as further detailed hereinbelow (FIG. 7C), otherwise the procedure continues to 703.

Figure 7A:
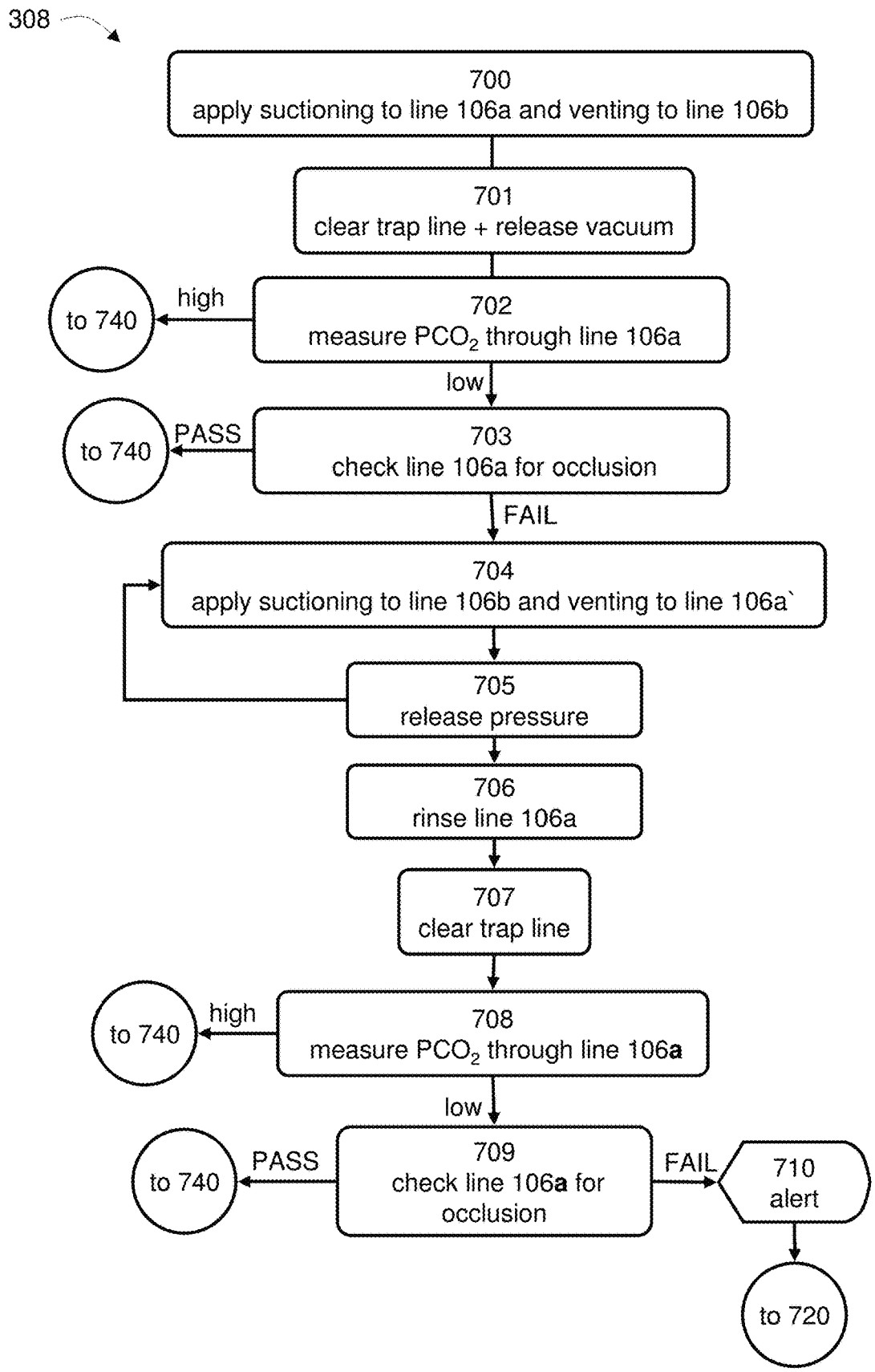
FIGS. 7A-7D are flowchart diagrams describing a more detailed procedure suitable to be executed, at least in part, during the primary cuff sealing phase, according to some embodiments of the present invention.

At 703 line 106a is checked for occlusion, for a predetermined time period which is typically from about 35 seconds to about 45 seconds, e.g., about 40 seconds. If there is no occlusion or the occlusion level is below a predetermined occlusion level threshold the procedure continues to 740 as further detailed hereinbelow (FIG. 7C), otherwise the procedure continues to 704. Typical value for the predetermined occlusion level threshold is from about 60% to about 80%, e.g., about 70%. In FIG. 7A, the transition from 703 to 740 is designated PASS and transition from 703 to 704 is designated FAIL.

At 704 the procedure performs a suctioning operation through line 106b and a venting operation through line 106a, for a predetermined time period which is typically from about 8 seconds to about 12 seconds, e.g., about 10 seconds. The procedure continues to 705 at which the pressure is released for a predetermined time period which is typically from about 5 seconds to about 10 seconds, e.g., about 7 seconds. Operations 704 and 705 are preferably performed several times, e.g., 3-8 times. Thereafter, the procedure optionally continues to 706 at which a rinsing operation is applied to line 106a. A preferred procedure suitable for operation 706 is provided hereinbelow (FIG. 7E).

The procedure continues to 707 at which at which the trap line 137 is cleared. Operation 707 is preferably performed for a predetermined time period which is typically from about 10 seconds to about 20 seconds, e.g., about 15 seconds.

The procedure continues to 708 at which $PCO_2$ or any other leakage indicative parameter is measured through line 106a. If the leakage indicative parameter is above a predetermined threshold, which can be the same as the threshold applied at 702 the procedure continues to 740 as further detailed hereinbelow (FIG. 7C), otherwise the procedure continues to 709.

At 709, line 106a is checked for occlusion, for a predetermined time period which is typically from about 35 seconds to about 45 seconds, e.g., about 40 seconds. If there is no occlusion or the occlusion level is below a predetermined occlusion level threshold the procedure continues to 740 as further detailed hereinbelow (FIG. 7C), otherwise the procedure continues to 710, at which the procedure issues an alert signal. Typical value for the predetermined occlusion level threshold is from about 60% to about 80%, e.g., about 70%. In FIG. 7A, the transition from 709 to 740 is designated PASS and transition from 709 to 710 is designated FAIL. From 710 the procedure continues to 720 as further detailed hereinbelow (FIG. 7B).

Figure 7B:
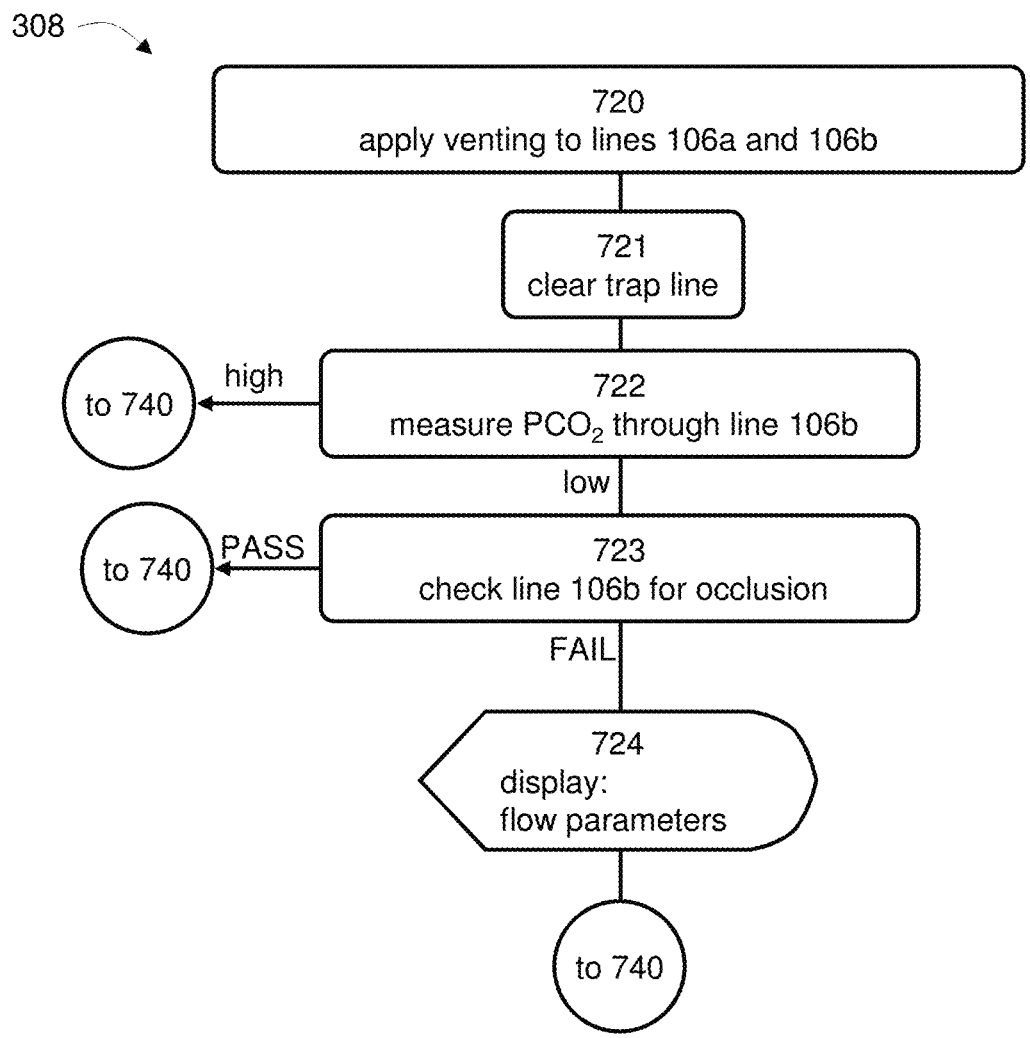

With reference to FIG. 7B, at 720 the procedure applies a venting operation to both lines 106a and 106b, preferably for a relatively short time period which is typically from about 150 ms to about 250 ms, e.g., about 200 ms. The procedure continues to 721 at which at which trap line 137 is cleared. Operation 721 is preferably performed for a predetermined time period which is typically from about 10 seconds to about 20 seconds, e.g., about 15 seconds.

The procedure continues to 722 at which $PCO_2$ or any other leakage indicative parameter is measured through line 106b. This measurement is preferably performed for a predetermined time period which is typically from about 35 seconds to about 45 seconds, e.g., about 40 seconds.

If the leakage indicative parameter is above a predetermined threshold (e.g., about 2 mmHg, for the case of $PCO_2$) the procedure continues to 740 as further detailed hereinbelow (FIG. 7C), otherwise the procedure continues to 723.

At 723 line 106b is checked for occlusion, for a predetermined time period which is typically from about 35 seconds to about 45 seconds, e.g., about 40 seconds. If there is no occlusion or the occlusion level is below a predetermined occlusion level threshold the procedure continues to 740 as further detailed hereinbelow (FIG. 7C), otherwise the procedure continues to 724. Typical value for the predetermined occlusion level threshold is at least 80% preferably about 100%. In FIG. 7B, the transition from 723 to 740 is designated PASS and transition from 723 to 724 is designated FAIL.

At 724 the procedure optionally and preferably displays flow parameters describing the flow or lack thereof in lines 106a and 106b. From 724 the procedure can exit, preferably to main phase 304.

Figure 7C:
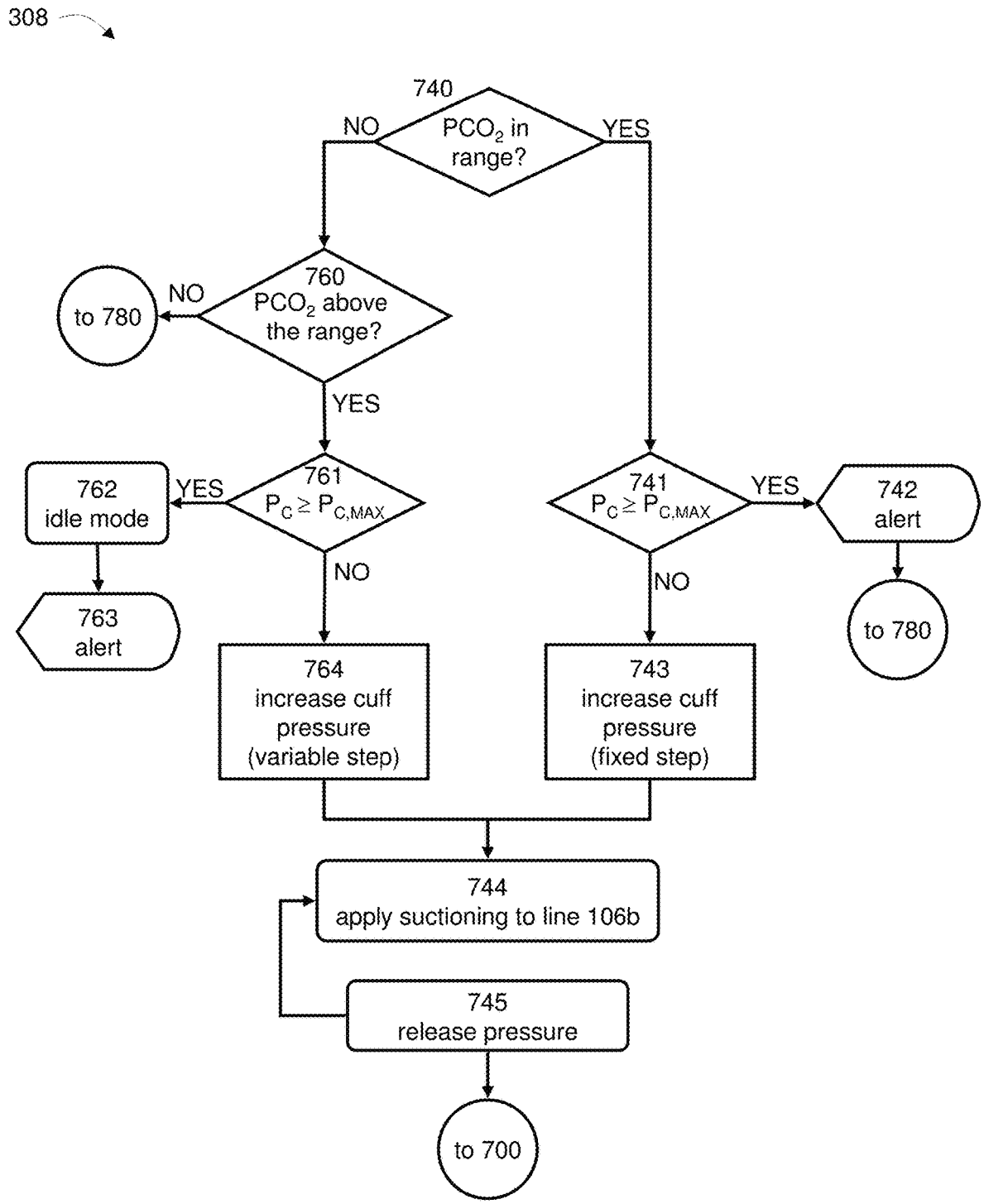

With reference to FIG. 7C, at decision 740 the procedure determines whether the leakage indicative parameter is within a predetermined range (e.g., between 2 mmHg and 3 mmHg, for the case of $PCO_2$).

If the leakage indicative parameter is not within the predetermined range, the procedure continues from 740 to 760, as further detailed hereinbelow. If the parameter is within the range, the procedure continues to decision 741 at which the procedures determine whether $P_C$ has reached the value of $P_{C,MAX}$.

Figure 7D:
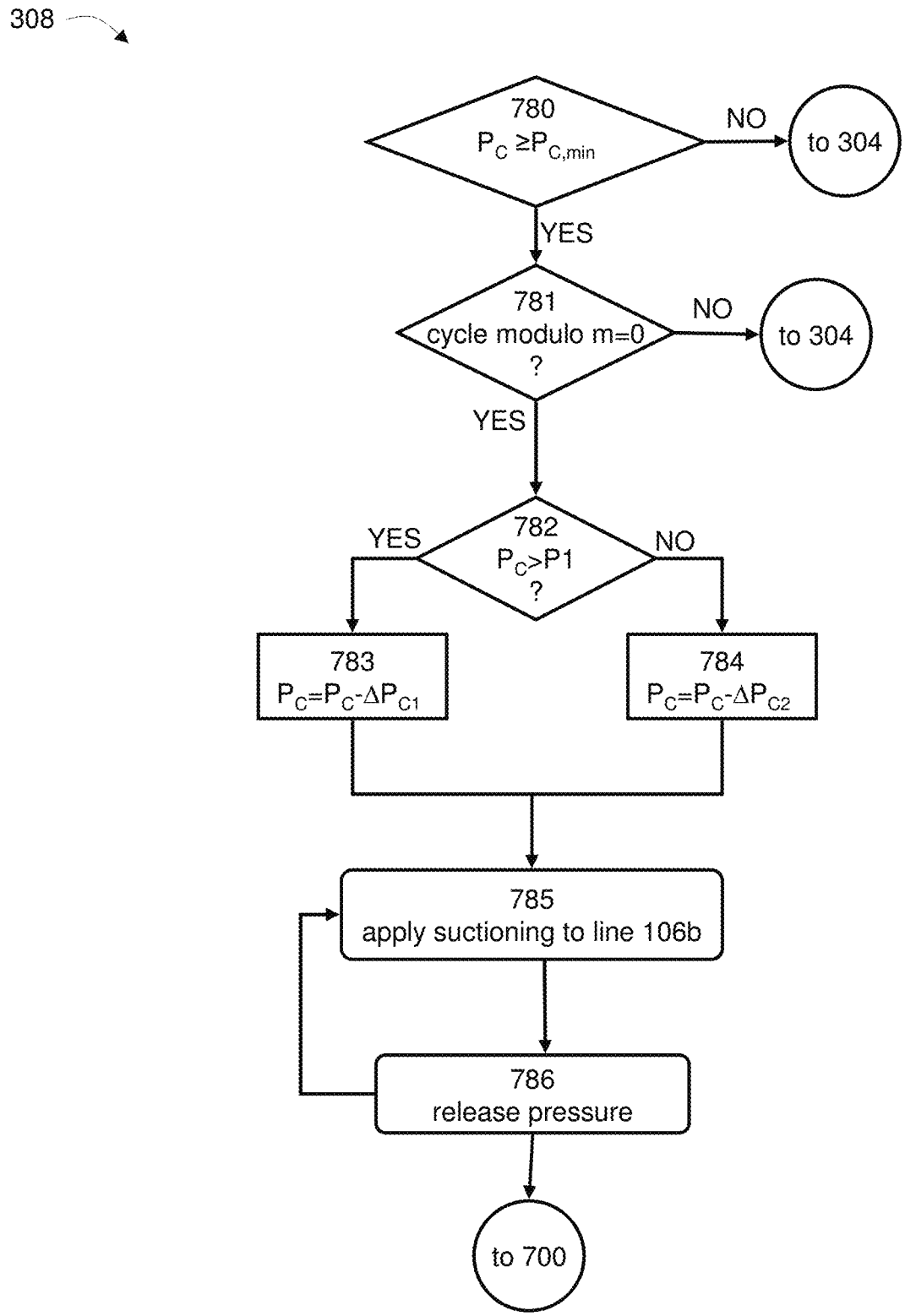
Figure 7E:
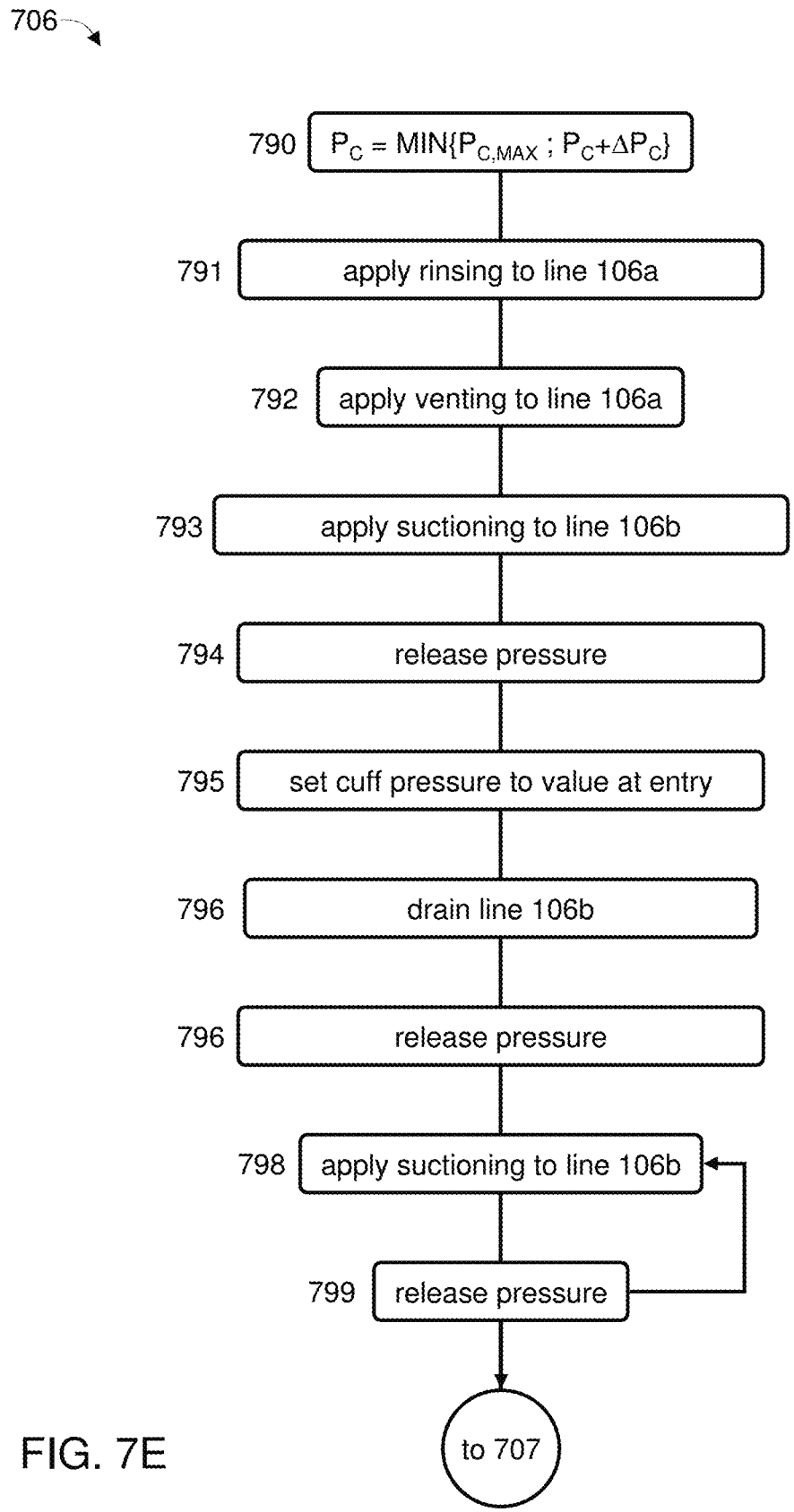
FIG. 7E is a flowchart diagram illustrating a procedure suitable for rinsing a fluid line when the fluid line is occluded or partially occluded, according to some embodiments of the present invention.

If $P_C \geq P_{C,MAX}$, the procedure continues to 742 at which the procedure issues an alert, that leakage is detected although the cuff pressure is maximal. It was found by the present inventors that such situation has a high likelihood of being indicative of incorrect positioning of the endotracheal tube with the trachea. The alert can therefore also include a message that endotracheal tube is incorrectly positioned. From 742 the procedure continues to 780 as further detailed hereinbelow (FIG. 7D).

If $P_C < P_{C,MAX}$, the procedure continues to 743 at which the cuff pressure $P_C$ is increased, optionally and preferably at a fixed step size. A typical incremental step in $P_C$ at 743 is about 1 mmHg. From 743 the procedure continues to 744 at which a suctioning operation is applied to line 106b. the procedure continues to 745 at which the pressure is released for a predetermined time period which is typically from about 5 seconds to about 10 seconds, e.g., about 7 seconds. From 745 the procedure loops back to 744. Operations 744 and 745 are preferably performed several times, e.g., 3-8 times. Thereafter, the procedure can loop back to 700.

At 760, the procedures determine whether the leakage indicative parameter is above the predetermined range (e.g., above 3 mmHg, for the case of $PCO_2$). If the parameter is not above the range, the procedure continues to 780 as further detailed hereinbelow (FIG. 7D). If the parameter is above the range, the procedure continues to decision 761 at which the procedures determine whether $P_C$ has reached the value of $P_{C,MAX}$.

If $P_C \geq P_{C,MAX}$, the procedure continues to 762 at which the system enters an idle mode and awaits for user instructions. For example, the operator can instruct the system to perform the safety procedure 302. Optionally, the procedure also displays an alert 763, which may be similar to alert 742 but may also include a message indicating that the system is idle and awaiting input due to high measured $CO_2$ level while at maximal cuff pressure.

If $P_C < P_{C,MAX}$, the procedure continues to 764 at which the cuff pressure $P_C$ is increased, optionally and preferably at a step size that varies as a function of $P_C$. A typical incremental step in $P_C$ at 764 is about $0.5*(P_C+P_{C,MAX})$. From 764 the procedure continues to 744 as further detailed hereinabove.

With reference to FIG. 7D, at decision 780 the procedure determines whether the cuff pressure $P_C$ is above a predetermined minimal cuff pressure threshold $P_{C,min}$. If $P_C$ is above $P_{C,min}$, the procedure continues to decision 781, otherwise the procedure exits, preferably to main phase 304. A typical value for $P_{C,min}$ is from about 10 mmHg to about 20 mmHg, e.g., about 15 mmHg.

At 781 the procedure determines whether the cycle number modulo m is 0, where m is a positive integer greater than 1. In some embodiments m=2. The cycle number is an integer that counts the number times the procedure enters decision 781. If the cycle number modulo m is not 0, the procedure exits, preferably to main phase 304, otherwise the procedure continues to decision 782. For example, for m=2, the procedure continues to decision 782 every other entry to 781. Another example, is m=1 wherein the procedure continues to decision 781 every entry to 781.

At 782 the procedure compares the value of $P_C$ to a predetermined threshold P1. If $P_C > P1$, the procedure continues to 783, otherwise the procedure continues to 784. A typical value for P1 is from about 15 mmHg to about 20 mmHg, e.g., about 18 mmHg.

At 783 the value of $P_C$ is reduced by $\Delta P_{C1}$ and at 784 the value of $P_C$ is reduced by $\Delta P_{C2}$, where $\Delta P_{C1}$ and $\Delta P_{C2}$ are two predetermined and different step parameters ($\Delta P_{C1} > \Delta P_{C2}$). A typical value for $\Delta P_{C1}$ is from about 0.5 mmHg to about 1.5 mmHg, e.g., about 1 mmHg, and a typical value for $\Delta P_{C2}$ is from about 0.3 mmHg to about 0.7 mmHg, e.g., about 0.5 mmHg.

From any of 783 and 784 the procedure continues to 785 at which a suctioning operation is applied to line 106b. The procedure continues to 786 at which the pressure is released for a predetermined time period which is typically from about 5 seconds to about 10 seconds, e.g., about 7 seconds. From 786 the procedure loops back to 785. Operations 785 and 786 are preferably performed several times, e.g., 3-8 times. Thereafter, the procedure can loop back to 700, or exit.

FIG. 7E is a flowchart diagram illustrating a procedure suitable for rinsing a fluid line when the fluid line is occluded or partially occluded. The procedure can be applied for any of the fluid lines. The procedure is useful particularly, but not exclusively, for operation 706 above, in which line 106a is rinsed. The embodiments below are therefore explained in terms of line 106a, but the skilled person, provided with the details described herein would know how to adjust the process for other fluid lines, for example, by interchanging 106a and 106b.

At 790 the procedure increases the cuff pressure $P_C$. Preferably the increment is done so as not to exceed the value of $P_{C,MAX}$. Specifically, the procedure sets the value of $P_C$ to the minimal value of the pair $\{P_{C,MAX}$ and $P_C+\Delta P_C\}$, where $\Delta P_C$ is a predetermined increment threshold. A typical value for $\Delta P_C$ is from about 1 mmHg to about 10 mmHg, e.g., about 5 mmHg. The procedure continues to 791 at which a rinsing operation is applied to the respective line (line 106a in the present example). The rinsing operation 791 is preferably performed for a predetermined time period which is typically from about 2 second to about 4 seconds, e.g., about 3 seconds. The procedure continues to 792 at which venting is applied to the respective line, for a predetermined time period which is typically from about 2 seconds to about 4 seconds, e.g., about 3 seconds. The procedure continues to 793 at which suctioning is applied to a complementary line (line 106b in the present example), for a predetermined time period which is typically from about 2 seconds to about 4 seconds, e.g., about 3 seconds. From 793 the procedure continues to 794 at which the pressure is released for a predetermined time period which is typically from about 5 seconds to about 10 seconds, e.g., about 7 seconds. The procedure then continues to 795 at which the cuff pressure is preset back to entry value when entering 790.

Thereafter, the procedure continues to 796 at which the complementary 106b line is drained without applying a venting operation through line 106a. Operation 796 is preferably performed for a predetermined time period which is typically from about 8 seconds to about 12 seconds, e.g., about 10 seconds. From 796 the procedure continues to 797 at which the pressure is released for a predetermined time period which is typically from about 5 seconds to about 10 seconds, e.g., about 7 seconds.

The procedure then continues to 798 at which a suctioning operation is applied to line 106b, for a predetermined time period which is typically from about 8 seconds to about 12 seconds, e.g., about 10 seconds. From 798 the procedure continues to 799 at which the pressure is released for a predetermined time period which is typically from about 5 seconds to about 10 seconds, e.g., about 7 seconds. From 799 the procedure loops back to 798. Operations 798 and 799 are preferably performed several times, e.g., 3-8 times. Thereafter, the procedure exits. For example, when the procedure is executed to perform operation 706 it can exit to 707.

Example 4

Exemplary Procedure for Staggered Delivery

FIG. 8 is a flowchart diagram describing a staggered rinsing procedure, according to some embodiments of the present invention.

At 800 the fluid line 106b is checked for occlusion, for a predetermined time period which is typically from about 15 seconds to about 25 seconds, e.g., about 20 seconds. The procedure continues to 801 at which the pressure is released for a predetermined time period which is typically from about 5 seconds to about 10 seconds, e.g., about 7 seconds. From 801 the procedure continues to decision 802 at which the procedure determines whether or not there is an occlusion in the respective line. If occlusion is detected, the procedure exits 803 without continuing the staggered rinsing procedure.

If occlusion is not detected the procedure continues to 804 at a continuous rinsing operation is applied to line 106b for a controlled and predetermined rinsing time period $t_r$. Thereafter, the procedure continues to 805 at which the rinsing in line 106b is ceased for a controlled and predetermined gap time period $t_g$. From 805 the procedure loops back to 804. Operations 804 and 805 are preferably performed until line 106b is filled by its entirety. Thus, denoting the volume of line 106b by $V_b$ and the volume of liquid delivered during operation 804 by $\Delta V$, Operations 804 and 805 are preferably performed $\Delta b/\Delta V$ times.

At 806 a continuous rinsing operation is applied to line 106a for a controlled and predetermined rinsing time period $t_r$. Thereafter, the procedure continues to 807 at which the rinsing in line 106b is ceased for a controlled and predetermined gap time period $t_g$. From 807 the procedure loops back to 806. Operations 806 and 807 are preferably performed several times until the amount of liquid which is required for rinsing the trachea is delivered. Thus, denoting the required volume of liquid by $V_r$ and the volume of liquid delivered during operation 806 by $\Delta V$, Operations 806 and 807 are preferably performed $V_r/\Delta V$ times.

At 808 a continuous venting operation is applied to line 106a for a controlled and predetermined venting time period $t_v$. Thereafter, the procedure continues to 809 at which the venting in line 106b is ceased for a controlled and predetermined gap time period $t_g$.

Following 809, the procedure exits 810.

Typically, but not necessarily, the value of the ratio $t_g/t_r$ is from about 0.1 to about 10, more preferably from about 1 to about 5, more preferably from about 2 to about 4, e.g., about 3.

Typical values for $t_r$ and $t_v$ are from about 0.5 seconds to about 1.5 seconds, e.g., 1 second, and a typical value for $t_g$ is from about 2 seconds to about 4 seconds, e.g., 3 second.

In some embodiments of the present invention, $t_r=t_v=1$ second, $t_g=3$ seconds, operations 804 and 805 are repeated 9 times each, and operations 804 and 805 are repeated 3 times each.

Example 5

Cuff Pressure History

It was found by the present inventors that making records of the cuff pressure during the ventilation of the subject is beneficial from the standpoint of reducing risk of developing clinical complications during intubation. Thus, in some embodiments of the present invention the cuff pressure, as monitored by main controller 120, is recoded over a predetermined period of time, which is typically from several hours to several days, e.g., 6, 12, 18 or 24 hours.

The data collected can be presented both at bedside or it can be transmitted to a remote location. In some embodiments of the present invention the data is presented while being collected, in which case the presented data is updated during the presentation. The data can be presented graphically, as a function of the time and/or frequency.

Aside for raw cuff pressure data, the present Inventors also contemplate recordable of analyzed data, such as, but not limited to, data pertaining to secretion leak history, data pertaining to obstruction history of the main lumen or other lumens of the endotracheal tube device, data pertaining to lung compliance and data pertaining to tracheal pressure.

Figure 9:
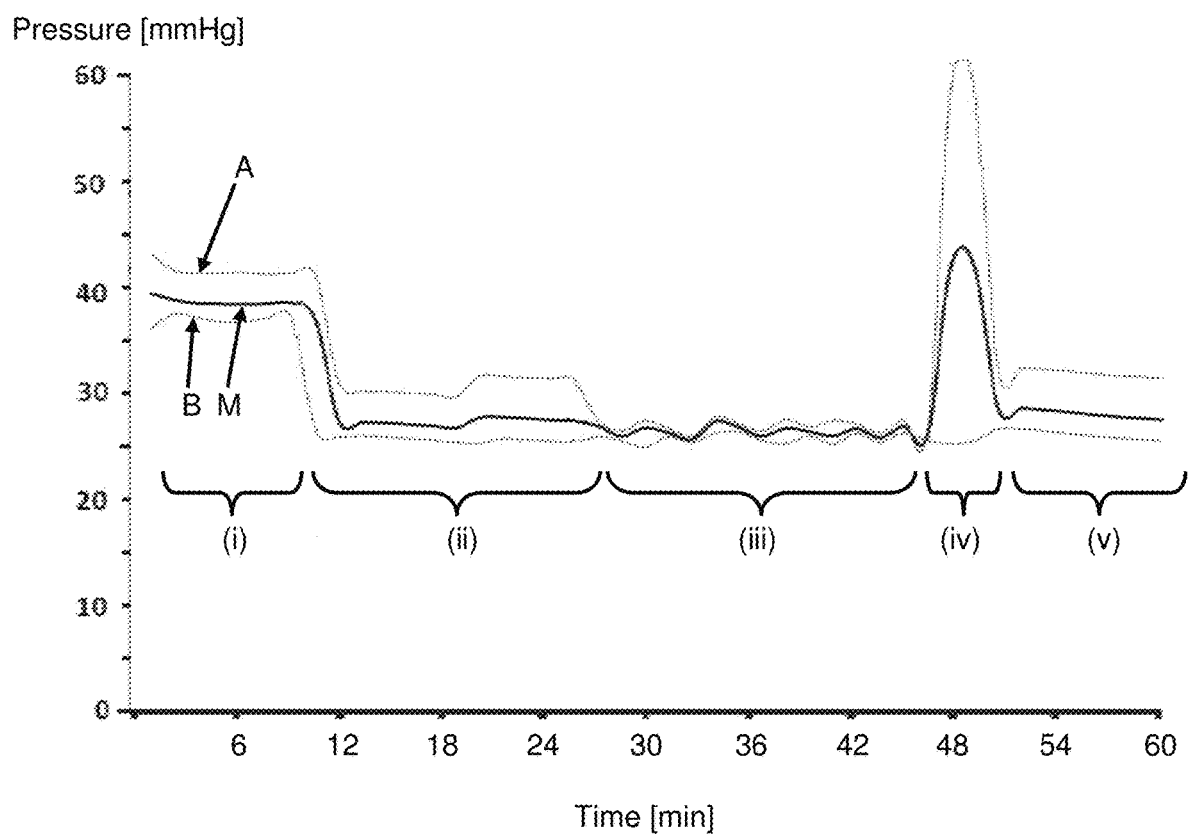
FIG. 9 shows intra cuff pressure in mmHg as a function of the time in minutes, as recorded in experiments performed according to some embodiments of the present invention.

FIG. 9 shows the intra cuff pressure (ICP) in mmHg as a function of the time in minutes, as recorded in the laboratory using tracheal and lungs simulator and ventilator, as further detailed in Example 8 hereinbelow. The cuff pressure data were recorded for many hours, and FIG. 9 shows a 60 minute section of typical data. Three curves are derived from the ICP data. Curve A is the maximal value of ICP as measured at a given period of 1 minute. It reflects the maximal induced ventilator pressure (Ppeak) on the cuff in the inhalation phase. Curve B is the minimal ICP as measured at a given period of 1 minute and reflects ventilator pressure at a point in time immediately after the exhalation phase. This point in time is referred to as Positive End-Expiratory Pressure (PEEP). Curve M is the measured median value between curves A and B.

During safety procedure 302, the ICP was set to 40 mmHg. This level was maintained for about 12 minutes, as shown in region (i) of FIG. 9. During the main phase 304, the ICP was reduced to about 25 mmHg. Until approximately minute 30, the difference between the maximal and minimal values (curves A and B) was about 5 mmHg, as shown in region (ii). This was interpreted by the present inventors as corresponding to normal behavior of cuff under inhale pressures exerted by the lungs.

The time-interval from approximately minute 30 to approximately minute 46 is marked as region (iii). Over this time-interval the difference between curves A and B dropped to less than 1 mmHg. It was found by the present inventors that such a drop is indicative of occlusion in the cuff inflation line. In various exemplary embodiments of the invention this difference is detected automatically by data analysis techniques. A representative example of such analysis by means of Fourier Transform is provided herein below.

The embedded cuff inflation lumen and its external tube leading to pilot balloon and check valve are of relatively low diameter. A droplet of fluid in this tubing may obstruct the readings of pressure from the cuff. Additionally, when the cuff inflation line is obstructed, capillary effects prevent the system from controlling the pressure in the cuff, so that only the volume up to obstruction is controlled.

The mechanism of forming the droplets of fluid in the cuff inflation line is as follows. At each inhale phase, ambient air at about 20° C. is pumped into lungs via the main lumen, keeping walls of the tube at a low temperature relatively to the temperature of the exhaled gas and tracheal tissue (about 36° C. with high humidity). The exhaled vaporized gases at higher pressure than cuff are infiltrating the permeable downstream walls and accumulated within the spatial volume around the pillaring low temperature tube. As result the humid gas condensates on tube and once infiltrating into the embedded lumen the droplets created are oscillatory driven toward the pilot balloon.

Approximately at minute 46, the system of the present embodiments began a clearing operation in which the maximal ICP value was gradually increased to about 60 mmHg, such that the median value is about 40 mmHg. In accordance with some embodiments of the present invention, the pressure was kept high for a period which is at most 2 minutes. This procedure is indicated as region (iv) in FIG. 9.

Thereafter, at approximately minute 50, the difference between the maximal and minimal values returned to its normal value (about 5 mmHg) indicating that the system successfully cleared the cuff inflation line [region (v)]. In the event that the difference between the maximal and minimal values of the ICP does not return to the normal value, the system preferable issues an alert signal as further detailed hereinabove.

FIG. 9 demonstrates the usefulness of the presentation of history data. Such presentation allows the physician to observe events during the patient intubation. In various exemplary embodiments of the invention the presentation is such that allows to physician to zoom into a segment of the data.

Example 6

Cuff Pressure Disturbances

The present inventors found that it is beneficial to enter a reduced mode of operation (e.g., a mode in which the rinsing operation is disabled), when an event such as coughing and weaning is detected. The present inventors found that such events can be identified by analyzing the variations in cuff pressure.

FIGS. 10A-10H show experimental data derived from data logger file of a 92 year old ventilated male patient hospitalized in the Rambam Medical Center (RMC), Israel. The ventilation was controlled for 7 days using the system of the present embodiments. The data were recorded at a sampling frequency of 20 Hz, with each record including many parameters and events.

Figure 10A:
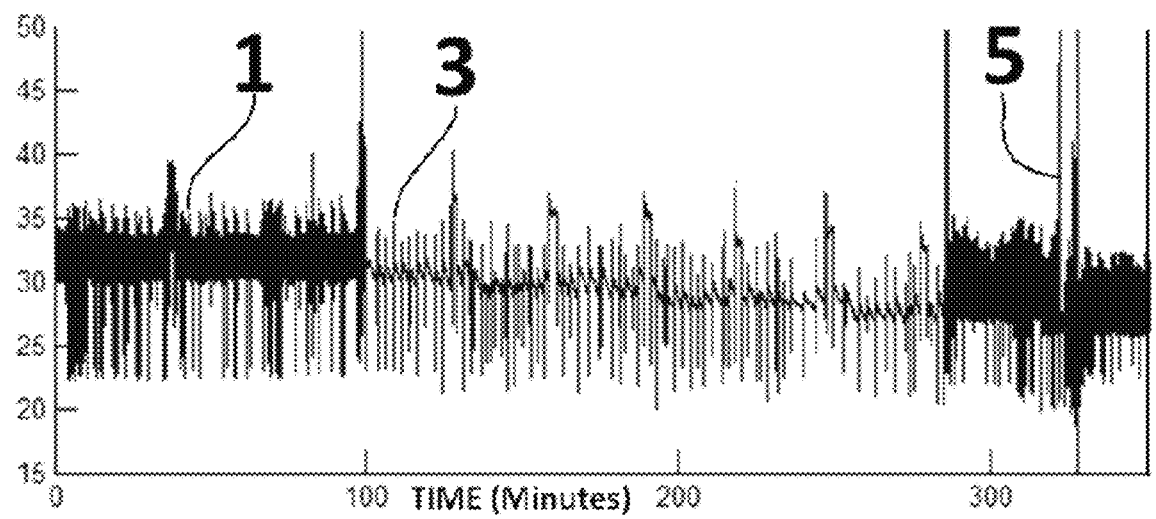
FIGS. 10A-10H show experimental data recorded according to some embodiments of the present invention from a 92 year old ventilated patient.
Figure 10B:
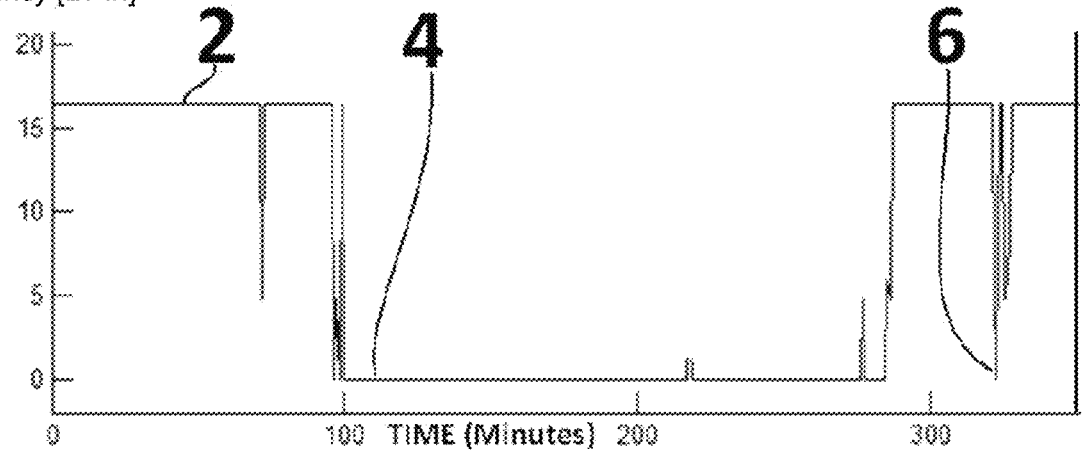
Figure 10C:
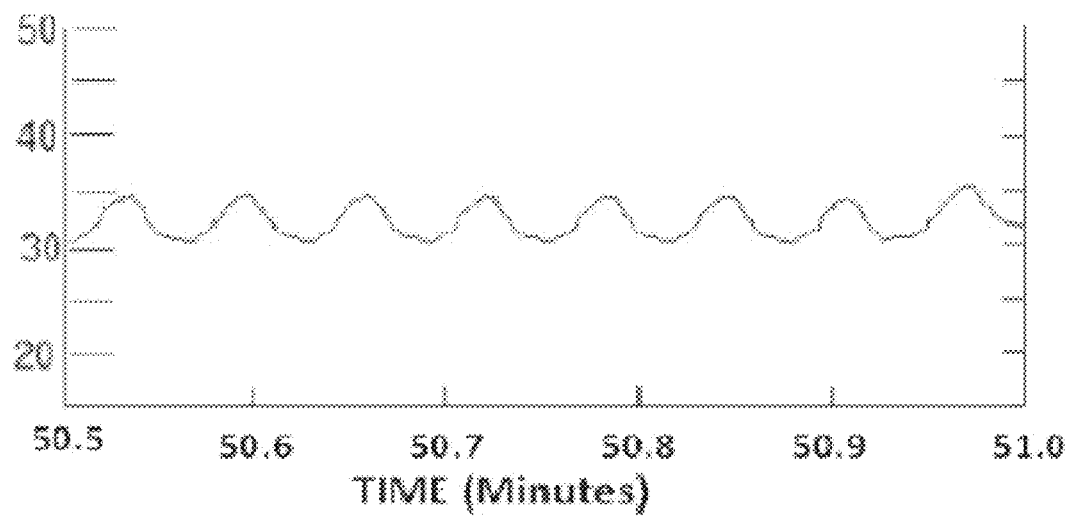
Figure 10D:
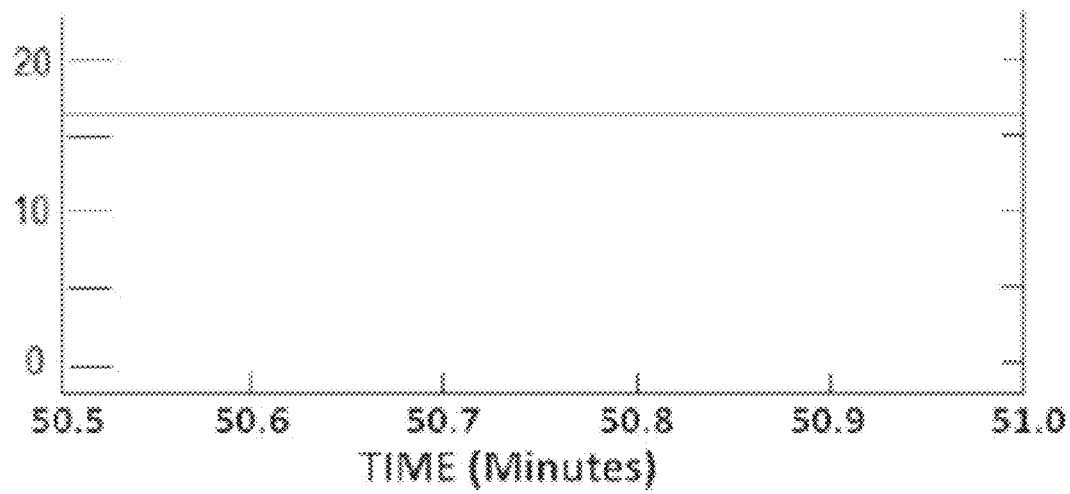
Figure 10E:
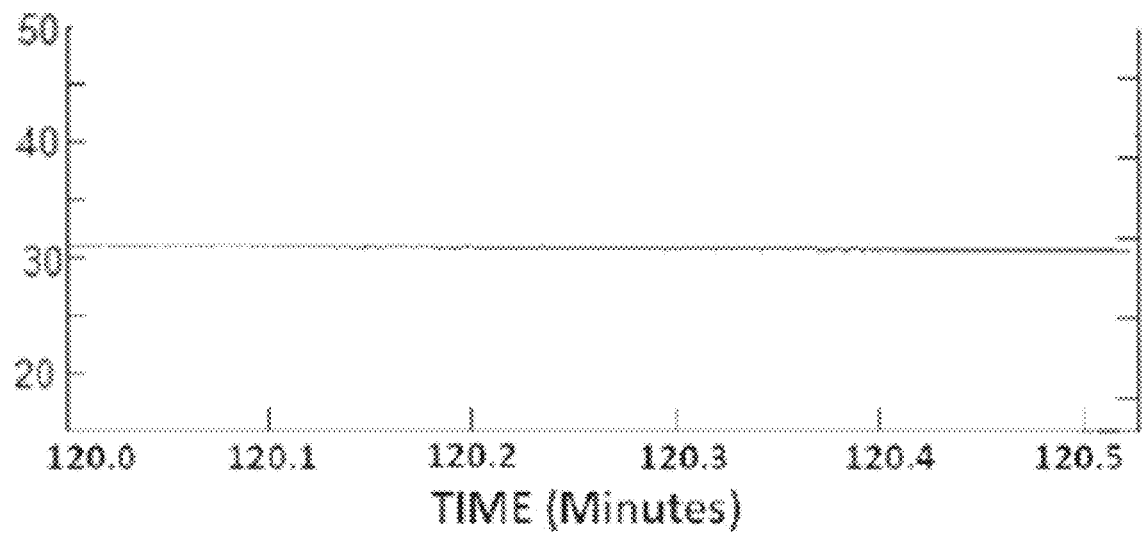
Figure 10F:
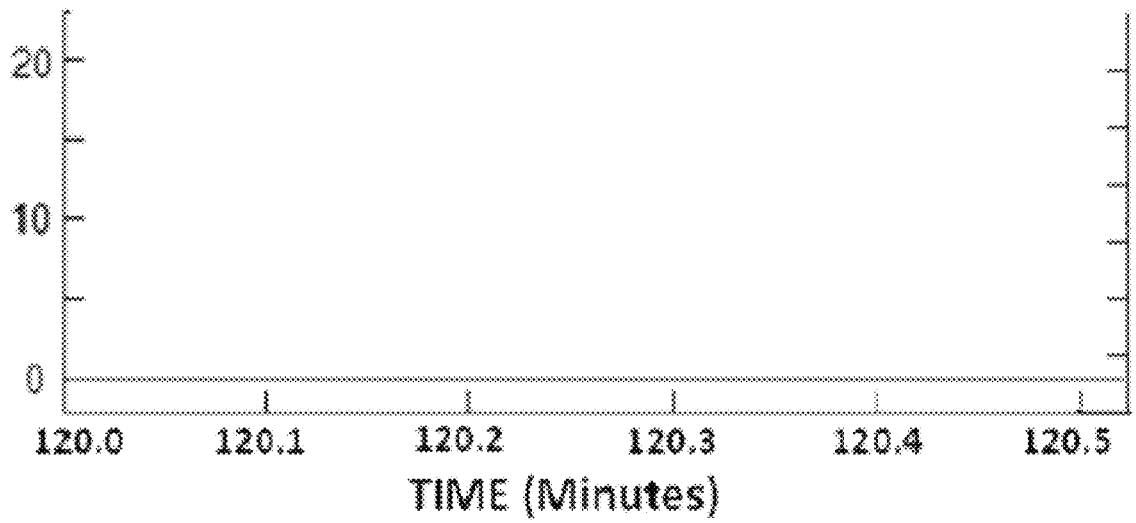
Figure 10G:
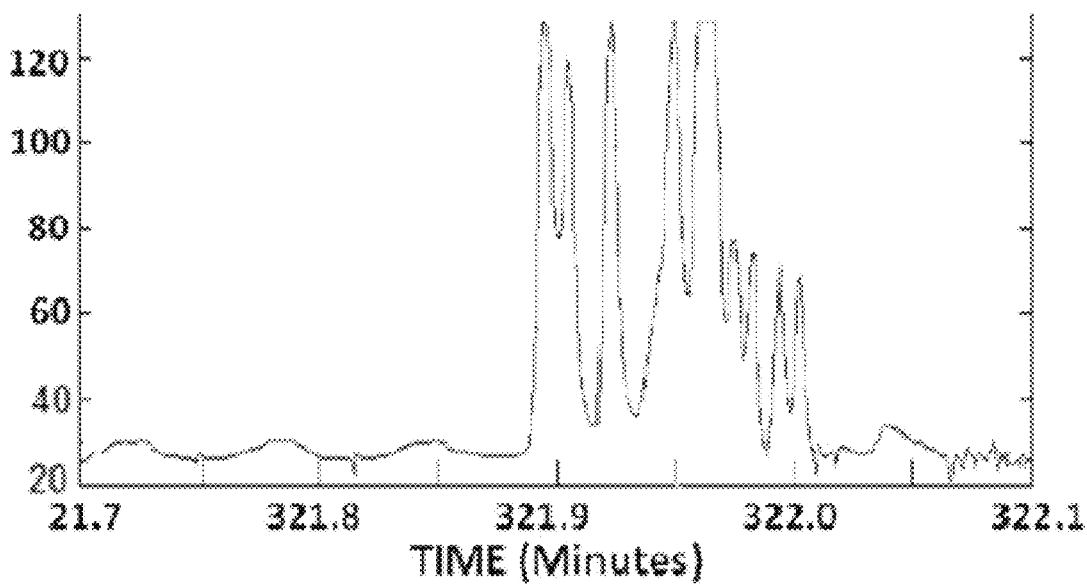
Figure 10H:
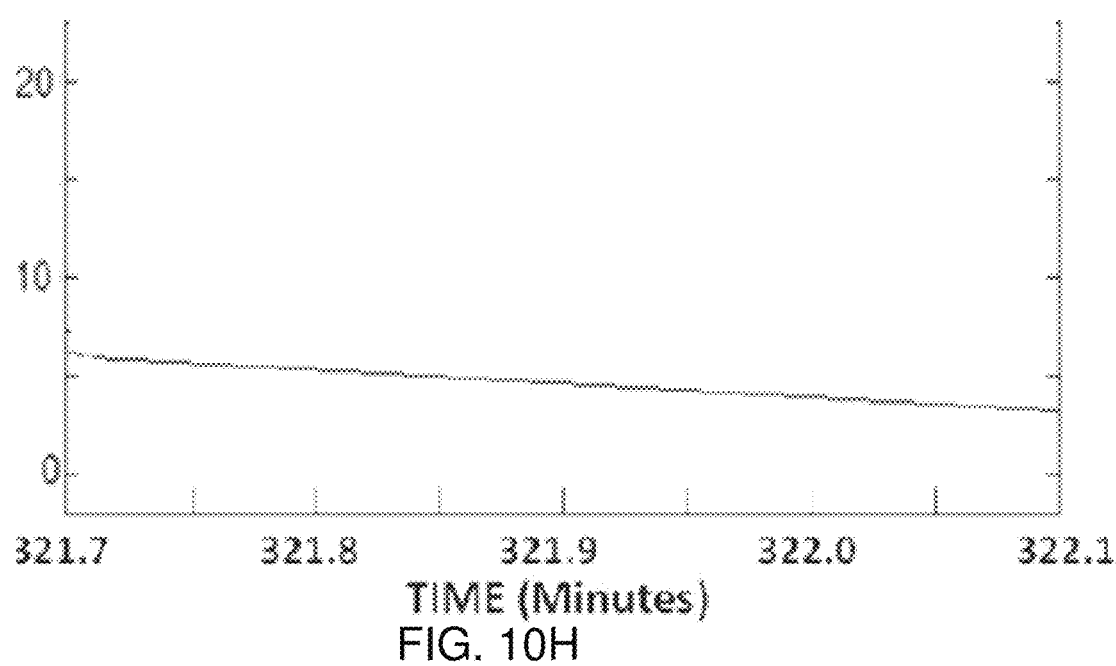

The data presented in FIGS. 10A and 10B relate to 6 hours of recordings. FIG. 10A shows the ICP in mmHg, and FIG. 10B shows the corresponding dominated frequency in breaths per minute (BPM) as a function of the time in minutes. In each of FIGS. 10A and 10B, three regions are marked by numerals 1, 3 and 5 (FIG. 10A) and 2, 4 and 6 (FIG. 10B). FIGS. 10C-10H show 30 second segments of the recorded data, respectively corresponding to regions 1-6 of FIGS. 10A and 10B, where FIGS. 10C, 10E and 10G show the ICP, and FIGS. 10D, 10F and 10H show the frequency as a function of the time.

FIGS. 10C and 10D (regions 1 and 2, respectively) show data characteristic to normal cuff reflection of induced ventilation pressures. As shown, the ICP has a generally periodic sine-wave like dependence on the time (FIG. 10C), with a generally flat frequency dependence of about 16 BPM (FIG. 10D).

FIGS. 10E and 10F (regions 3 and 4, respectively) show data characteristic to an obstruction event in the cuff inflation line. As shown, the ICP has a generally flat shape at a fixed pressure value of about 30 mmHg (FIG. 10E), and is generally devoid of frequency content (FIG. 10F).

FIGS. 10G and 10H (regions 5 and 6, respectively) show data characteristic to a disturbance. A coughing event was observed at an approximate time of 322 minutes (FIG. 10G). The cuff pressure became noisy for about 7 seconds and reached amplitudes above 120 mmHg. Note that in FIG. 10C the normal amplitude was generally between 30 mm Hg and 35 mmHg and (occasionally raised to 40 mmHg during rinsing sessions). The frequency content (FIG. 10H) show a decrease of frequency to less than 5 Hz compared to 16 Hz at normal cuff pressures (FIG. 10D).

Returning again to the 6 hour plots (FIGS. 10A-10B), the observed coughing events occurred sporadically and the system interpreted it as is without changing control algorithms.

In some embodiments of the present invention when the noise is persistent, the system turns switches to a reduced mode, e.g., a mode in which the cuff pressure is controlled without executing rinsing procedures at mild suction volumes.

Example 7

Detection of Cuff Puncture or Rupture

Figure 11A:
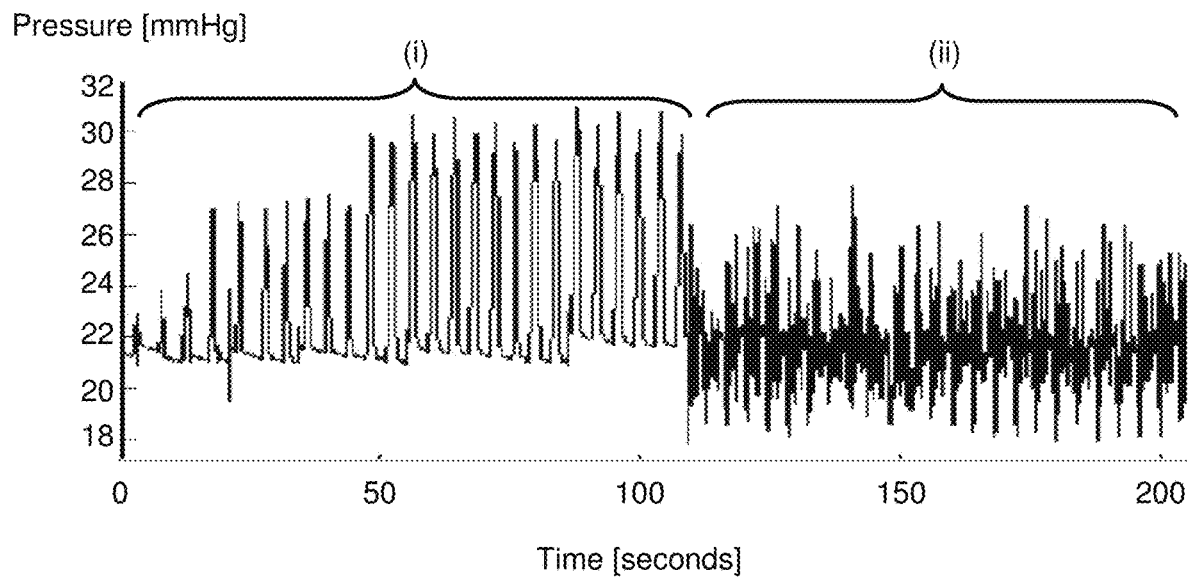
FIGS. 11A-11C show experimental data pertaining to punctured cuff, as obtained during experiments performed according to some embodiments of the present invention.
Figure 11B:
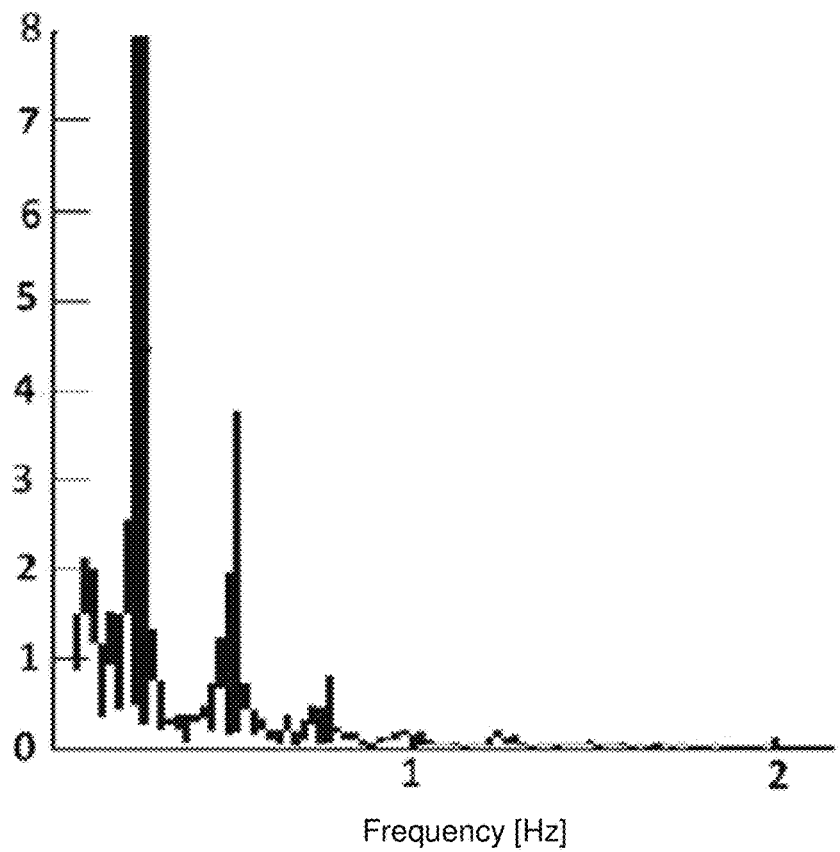
Figure 11C:
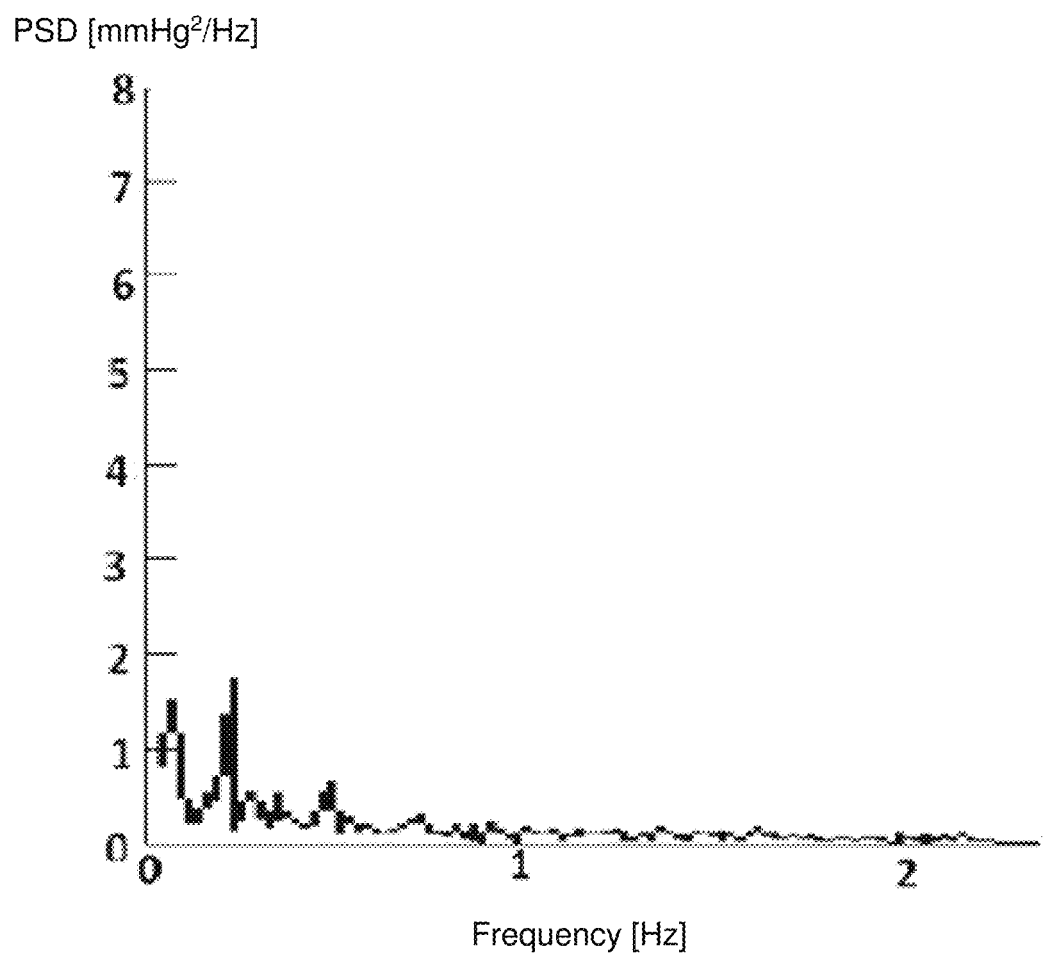

FIGS. 11A-11C show experimental data recorded from laboratory simulation performed using a model trachea and a lung simulator as further detailed in Example 8 hereinbelow. In the present Example, the cuff was punctured during the simulation.

FIG. 11A shows the ICP in mmHg as a function of the time in seconds over a period of 200 seconds. Two regions (i) and (ii) are marked on FIG. 11A, where the transition from (i) to (ii) occurs approximately at second 110. The calculated PSD corresponding to region (i) is shown in FIG. 11B and the calculated PSD corresponding to region (ii) is shown in FIG. 11B. In the present example, the PSD was calculated as the square of the pressure divided by the frequency, and FIGS. 11B and 11C therefore show the respective PSD in $mmHg^2/Hz$ as a function of the frequency in Hz.

Region (i) is characteristic to a situation in which the cuff is not punctured, and region (ii) is characteristic to a situation in which the cuff is punctured but still remains in contact with the tissue.

In region (i), the ICP oscillated between about 21 mmHg and about 30 mmHg. The corresponding PSD (FIG. 11B) had a main component of about 8 $mmHg^2/Hz$ at a frequency of about 0.25 Hz (15 BPM). In region (ii), the system of the present embodiments maintained a base pressure of approximately 22 mmHg, but the ICP, which was influenced by the cyclic inhale/exhale ventilating pressures and the constant air leaking through the puncture of the cuff, oscillated between about 19 mmHg and about 24 mmHg. The corresponding PSD (FIG. 11C) changed significantly. For example, the 8 mmHg$^2$/Hz dominant component of breathing was reduced by a factor of 4. The energy concentrated at the breathing frequency (15 BPM), in FIG. 11B, is reduced due to cuff puncture that prevent the absorption of breathing pressure and its reflection in energy dispersed at very low power levels at higher frequencies.

Thus, by analyzing the PSD the event that triggered the abrupt decrease in cuff pressure can be determined. For example, an abrupt decrease in the cuff pressure can occur when the ventilation pressure is decreased. However, for such an event, the cuff pressure typically does not oscillate around a pressure as shown in region (ii).

This Example demonstrates the ability of the system and method of the present embodiments to identify puncture in the cuff and to distinguish between different types of effects resulting in abrupt decrease of the cuff pressure.

Example 8

Measurement of Tracheal Pressure

In various exemplary embodiments of the invention the patient's reflexive reaction to start breathing at the end of the exhale phase is identified using the cuff pressure. This reaction is manifested when the PEEP is reduced by the patient's reflex system.

Due to the proximity between the cuff and the lungs, the reflexive reaction can be detected and provide the necessary triggering for assisted ventilation to prevent the patient excess WOB and other complications such as Acute Lung Injury (ALI), Ventilator Associated Lung Injury (VALI), and Acute Respiratory Distress Syndrome (ARDS).

Figure 12A:
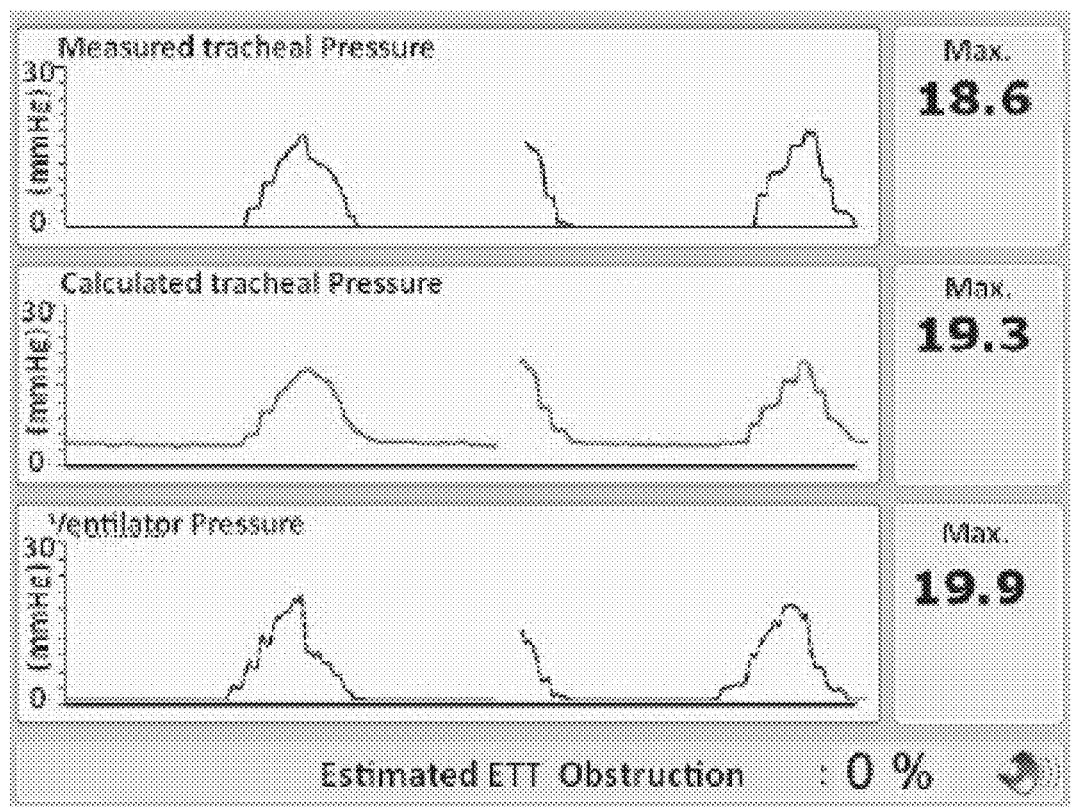
FIGS. 12A and 12B are snapshots of a display of a prototype system prepared and configured according to some embodiments of the present invention.
Figure 12B:
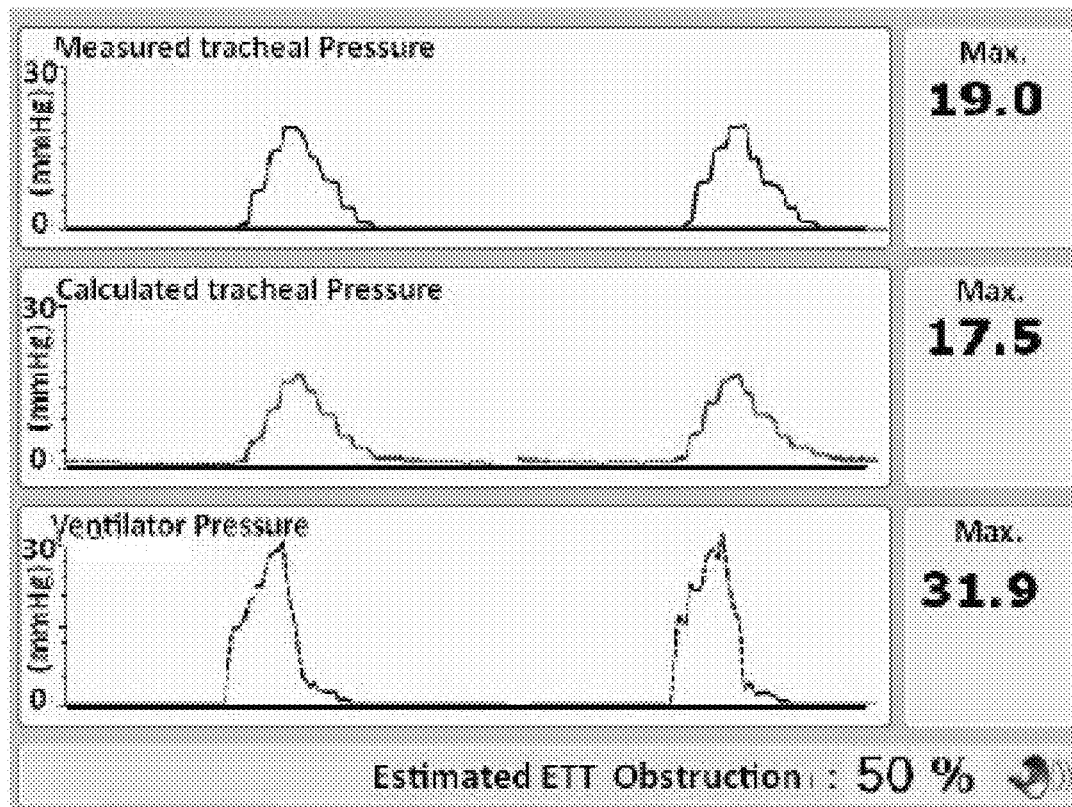

FIGS. 12A and 12B are snapshots of a display of a prototype system prepared and configured according to some embodiments of the present invention. The snapshots show data obtained while operating the system while connecting the proximal ends of the fluid lines of the endotracheal tube device illustrated in FIG. 2A to the connector panel of the system, and introducing the endotracheal tube into a model trachea, shaped as tube, about 20 mm in internal diameter.

The model trachea was connected to a lung simulator (LS-2000A, BC Biomedical of BC group international Inc. St. Louis, USA). The proximal end of the main lumen of the endotracheal tube was connected to a ventilator.

The pressure in the model trachea was measured within the model trachea, near the distal end of the endotracheal tube. The pressure was also calculated based on the cuff pressure as further detailed hereinabove. The following equation used to calculate the tracheal pressure: $P_{tr}=k_0+k_1 P_C$.

FIGS. 12A and 12B show the measured and calculated tracheal pressures and the ventilator pressure for an unobstructed (FIG. 12A) and obstructed (12B) endotracheal tube. Also shown are the obstruction level OL of the endotracheal tube (0% in FIG. 12A and 70% in FIG. 12B).

As shown in FIG. 12A, when the obstruction level is 0, there is a high level of similarity between the presented pressures.

As shown in FIG. 12B, when the obstruction level is high (70% in the present example), the shape of calculated and measured tracheal pressures remain similar, but the ventilator pressure is substantially different from the calculated and measured tracheal pressures.

This Example demonstrates the ability of the technique of the present embodiments to accurately calculate the tracheal pressure even when the endotracheal tube is obstructed. Furthermore the accuracy of the reflected tracheal pressure as measured by cuff pressure enables clear distinction and detection of assisted patient's pulmonary reflexes. This feature can be used to synchronize the ventilator with patient's pulmonary reflexes to decrease work of breathing (WOB) in order to prevent ventilation associated injuries and ease aspiration of secretions from the lungs using shallow or deep suction synchronized.

Example 9

Blood Pulse Wave Characteristics

The present inventors found that the cuff pressure data can be utilized for estimating blood pulse wave characteristics.

Figure 13A:
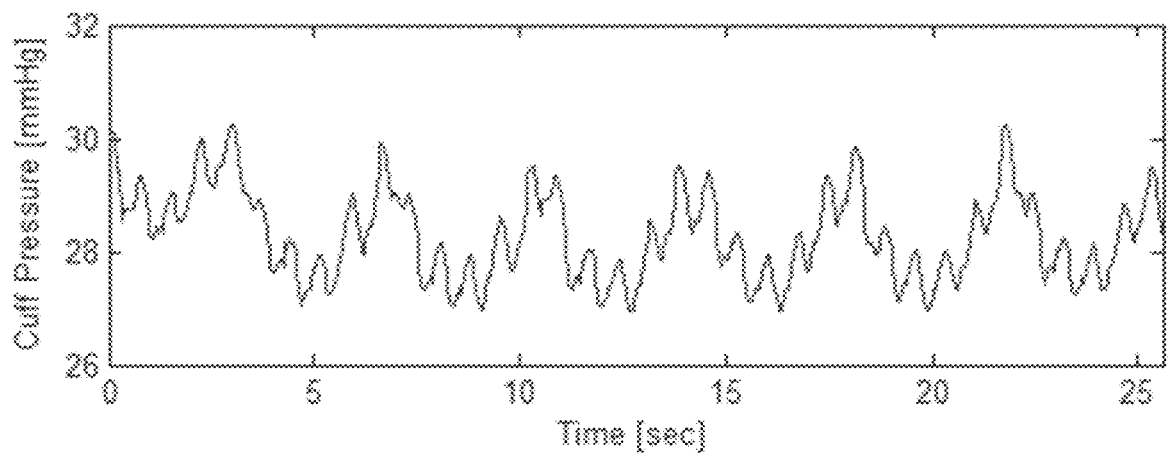
FIGS. 13A and 13B show cuff pressure data (FIG. 13A) and power spectrum analysis data (FIG. 13B) recorded according to some embodiments of the present invention during ventilation of an 87 year old male patient.
Figure 13B:
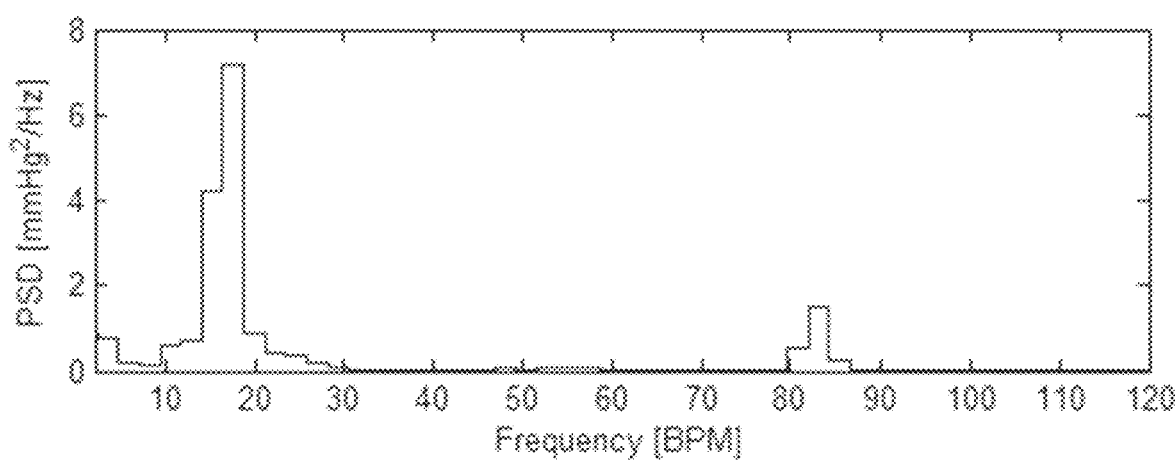

FIGS. 13A and 13B show cuff pressure data (FIG. 13A) and power spectrum analysis data (FIG. 13B) recorded during ventilation of an 87 year old male patient hospitalized in the Rambam Medical Center (RMC), Israel. The frequency in FIG. 13B is presented in units of BPM, but the ordinarily skilled person would be able to determine the frequency in other units. For example, the frequency in Hz can be obtained using the reaction 1 Hz=60 BPM.

Cuff pressure data were recorded during 5 days of oral intubation, at a sampling frequency of 20 Hz. The data presented in FIGS. 13A and 13B correspond to a time interval of 25 seconds. The patient was further connected to standard ICU blood pressure monitor. During the 25 second time-interval corresponding to the data in FIGS. 13A and 13B, the breathing rate as obtained by the ventilation machine was 18 BPM, and the pulse rate and blood pressure as obtained from the blood pressure monitor were, respectively, 83 BPM and 160 mmHg (systolic pressure).

As shown in FIG. 13A the cuff pressure varies according to a frequency which is modulated by another frequency. The PSD (FIG. 13B) shows two peaks. A first peaks is at a frequency of about 0.3 Hz and a second peak at about 1.38 Hz. The locations on the frequency axis of the first and second peaks are well correlated, respectively, to the breathing rate and blood pulse rate obtained from the ventilation machine and the blood pressure monitor.

Note that the height of the second peak is relatively small. Without wishing to be bound to any theory, it is postulated that since the transfer of pressure to the cuff due to the pulsatile blood flow is via the tissue between the arterial vasculature and the cuff, there is a damping effect that wherein some of the pressure is absorbed by the tissue without being transferred to the cuff. On the other hand, since the transfer of pressure to the cuff due to the motion of the lung is via the air column between the cuff and the lung, the damping effect for this pressure is negligible. Thus, although the area of the second peak is a proxy to the blood pressure, the value of the area is typically a damped pressure rather than the absolute blood pressure.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for controlling and monitoring flow in a cuffed endotracheal tube device, comprising:
   a connector panel having at least three connectors adapted for establishing fluid communication with proximal ends of at least a first fluid line, a second fluid line and a cuff inflation line of a cuffed endotracheal tube device;
   a processing unit configured to instruct a control unit to execute operations including at least a rinsing procedure, a suctioning procedure, a cuff inflation procedure, a leak detection procedure and a venting procedure;
   wherein said control unit comprises a cuff inflation and deflation module configured to measure a cuff pressure within said cuff inflation line, to identify cuff pressure variations, and to control said pressure responsively to said identified variations in closed loop control, wherein when amplitude of said variation is above a predetermined pressure threshold for a time period which is above a predetermined time threshold, said control unit instructs said cuff inflation and deflation module to reduce said cuff pressure;
   wherein said control unit is configured to temporarily cease said closed loop control when said cuff pressure variations are above a predetermined threshold.

2. The system according to claim 1, further comprising a user interface, wherein said control unit is configured to receive signals from said user interface and to vary or bypass at least one operation responsively to said signals.

3. The system according to claim 1, further comprising a housing and a disposable pneumatic module, wherein said housing is configured for receiving said disposable pneumatic module and said control unit is configured for operating said disposable pneumatic module.

4. The system according to claim 1, wherein said processing unit is configured for comparing said identified variations to a characteristic breathing pattern of a subject being intubated by the endotracheal tube, and wherein said cuff inflation and deflation module is configured to control said cuff pressure responsively to said comparison.

5. The system according to claim 4, wherein said cuff inflation and deflation module is configured for changing said pressure if a deviation of said identified variations from said characteristic breathing pattern is above a predetermined threshold.

6. The system according to claim 1, wherein said cuff inflation and deflation module is configured for gradually decreasing said pressure if said measured pressure is above a predetermined pressure threshold for a predetermined period of time.

7. The system according to claim 6, wherein said processing unit is configured to search for a statistically significant frequency of pressure spikes, and to determine cuff puncture existence if said statistically significant frequency is found.

8. The system according to claim 1, wherein said processing unit is configured for determining cuff rupture, and issuing an alert signal if cuff rupture is determined.

9. The system according to claim 1, wherein said processing unit is configured for identifying coughing events based on said pressure.

10. The system according to claim 9, wherein said processing unit is configured for monitoring said coughing events over time and issuing a statistical analysis report pertaining to said monitored coughing events.

11. The system according to claim 10, wherein said operations comprise a weaning phase in which at least two of said rinsing procedure, said suctioning procedure, said leak detection procedure and said venting procedure are disabled.

12. The system according to claim 1, wherein said processing unit is configured to determine cuff rupture existence if said cuff pressure is below a predetermined threshold or if an abrupt drop in said cuff pressure is identified.

13. The system according to claim 1, wherein said control unit is configured to maintain a generally constant cuff pressure, when variations are below predetermined value.

14. The system according to claim 13, wherein said control unit is configured to cease said maintenance of said generally constant cuff pressure for a predetermined time-interval, and wherein said processing unit is configured to analyze variations in cuff pressure within said cuff inflation line during said predetermined time-interval and to identify, based on said analysis, at least one event selected from the group consisting of: occlusion in said cuff inflation line, puncture in a wall of said cuff, rupture in a wall of said cuff and patient coughing.

15. The system according to claim 13, wherein said control unit is configured to cease said maintenance of said generally constant cuff pressure for a predetermined time-interval, and wherein said processing unit is configured to analyze variations in cuff pressure within said cuff inflation line during said predetermined time-interval and to calculate, based on said analysis, at least one quantity selected from the group consisting of: tracheal pressure, breathing frequency, blood pulse wave frequency, obstruction level of a main lumen of said endotracheal tube device and resistance of said main lumen to flow.

16. The system according to claim 13, wherein said control unit is configured to cease said maintenance of said generally constant cuff pressure for a predetermined time-interval, and wherein said processing unit is configured for providing an estimated prediction of the subject's spontaneous initiation of inhale and exhale and the subject's pulmonary power as function of time.

17. A ventilation system, comprising a ventilation machine and the system according to claim 1.

18. A method of ventilating a subject, comprising:
   intubating the subject with a cuffed endotracheal tube device having at least a main tube, a cuff inflation line, a first fluid line and a second fluid line;
   connecting said main tube to a ventilation machine; and
   connecting said a cuff inflation line, said first fluid line and said second fluid line to a system according to claim 1.

19. A system for controlling and monitoring flow in a cuffed endotracheal tube device, comprising:
   a connector panel having at least three connectors adapted for establishing fluid communication with proximal ends of at least a first fluid line, a second fluid line and a cuff inflation line of a cuffed endotracheal tube device;
   a processing unit configured to instruct a control unit to execute operations including at least a rinsing procedure, a suctioning procedure, a cuff inflation procedure, a leak detection procedure and a venting procedure;

wherein said control unit comprises a cuff inflation and deflation module configured to measure a cuff pressure within said cuff inflation line, to identify cuff pressure variations, and to control said pressure responsively to said identified variations in closed loop control, wherein when amplitude of said variation is above a predetermined pressure threshold for a time period which is above a predetermined time threshold, said control unit instructs said cuff inflation and deflation module to reduce said cuff pressure;

wherein said control unit is configured to maintain a generally constant cuff pressure, when variations are below predetermined value, and to cease said maintenance of said generally constant cuff pressure for a predetermined time-interval; and wherein said processing unit is configured to analyze variations in cuff pressure within said cuff inflation line during said predetermined time-interval and to identify, based on said analysis, at least one event selected from the group consisting of: occlusion in said cuff inflation line, puncture in a wall of said cuff, rupture in a wall of said cuff and patient coughing.

20. A system for controlling and monitoring flow in a cuffed endotracheal tube device, comprising:

a connector panel having at least three connectors adapted for establishing fluid communication with proximal ends of at least a first fluid line, a second fluid line and a cuff inflation line of a cuffed endotracheal tube device;

a processing unit configured to instruct a control unit to execute operations including at least a rinsing procedure, a suctioning procedure, a cuff inflation procedure, a leak detection procedure and a venting procedure;

wherein said control unit comprises a cuff inflation and deflation module configured to measure a cuff pressure within said cuff inflation line, to identify cuff pressure variations, and to control said pressure responsively to said identified variations in closed loop control, wherein when amplitude of said variation is above a predetermined pressure threshold for a time period which is above a predetermined time threshold, said control unit instructs said cuff inflation and deflation module to reduce said cuff pressure;

wherein said control unit is configured to maintain a generally constant cuff pressure, when variations are below predetermined value, and to cease said maintenance of said generally constant cuff pressure for a predetermined time-interval; and wherein said processing unit is configured to analyze variations in cuff pressure within said cuff inflation line during said predetermined time-interval and to calculate, based on said analysis, at least one quantity selected from the group consisting of: tracheal pressure, breathing frequency, blood pulse wave frequency, obstruction level of a main lumen of said endotracheal tube device and resistance of said main lumen to flow.

* * * * *